United States Patent
Udyavar et al.

(10) Patent No.: US 11,881,286 B2
(45) Date of Patent: Jan. 23, 2024

(54) CD8+ T CELL BASED IMMUNOSUPPRESSIVE TUMOR MICROENVIRONMENT DETECTION METHOD

(71) Applicant: GENENTECH, INC., South San Francisco, CA (US)

(72) Inventors: Akshata Ramrao Udyavar, Foster City, CA (US); Yulei Wang, Foster City, CA (US); Cleopatra Kozlowski, Woodside, CA (US)

(73) Assignee: GENENTECH, INC., South San Francisco, CA (US)

( * ) Notice: Subject to any disclaimer, the term of this patent is extended or adjusted under 35 U.S.C. 154(b) by 531 days.

(21) Appl. No.: 17/033,161

(22) Filed: Sep. 25, 2020

(65) Prior Publication Data
US 2021/0098082 A1   Apr. 1, 2021

Related U.S. Application Data

(60) Provisional application No. 62/907,062, filed on Sep. 27, 2019.

(51) Int. Cl.
| | |
|---|---|
| *G16B 40/00* | (2019.01) |
| *A61P 35/00* | (2006.01) |
| *C07K 16/22* | (2006.01) |
| *C07K 16/28* | (2006.01) |
| *A61K 39/00* | (2006.01) |
| *A61K 38/21* | (2006.01) |

(52) U.S. Cl.
CPC ............ *G16B 40/00* (2019.02); *A61K 38/217* (2013.01); *A61P 35/00* (2018.01); *C07K 16/22* (2013.01); *C07K 16/2827* (2013.01); *A61K 2039/507* (2013.01); *C07K 2317/76* (2013.01)

(58) Field of Classification Search
CPC ..... G16B 40/00; C07K 16/22; C07K 2317/76
See application file for complete search history.

(56) References Cited

PUBLICATIONS

Steiner et al. Impact of Deep Learning Assistance on the Histopathologic Review of Lymph Nodes for Metastatic Breast Cancer. Am J Surg Pathol 42, 1636-1646, 2018. (Year: 2018).*
Kobie et al. Transforming Growth Factor ß Inhibits the Antigen-Presenting Functions and Antitumor Activity of Dendritic Cell Vaccines. Cancer Res. 63, 1860-1864, 2003. (Year: 2003).*
Ungefroren H., Blockade of TGF-ß signaling: a potential target for cancer immunotherapy?, Expert Opinion on Therapeutic Targets, 23, 679-693, 2019. (Year: 2019).*
Batlle et al., Transforming Growth Factor-b Signaling in Immunity and Cancer. Immunity, 50, 924-940, 2019. (Year: 2019).*
Alexandrov, L. B., et. al., "Signatures of Mutational Processes in Human Cancer", Nature 500, 415-421, doi:10.1038/nature12477 (2013).
Aran, D., Hu, Z. & Butte, A. J. xCell, "Digitally Portraying the Tissue Cellular Heterogeneity Landscape", Genome Biol 18, 220, doi:10.1186/s13059-017-1349-1 (2017).
Aryee, M. J., et. al., "Minfi: a Flexible and Comprehensive Bioconductor Package for the Analysis of Infinium DNA Methylation Microarrays", Bioinformatics 30, 1363-1369, doi:10.1093/bioinformatics/btu049 (2014).
Bibikova, M., et. al., "High Density DNA Methylation Array with Single CpG Site Resolution", Genomics 98, 288-295, doi:10.1016/j.ygeno.2011.07.007 (2011).
Brahmer, J. R. et. al., The Society for Immunotherapy of Cancer Consensus Statement on Immunotherapy for the Treatment of Non-small Cell Lung Cancer (NSCLC). J Immunother Cancer 6, 75, doi:10.1186/s40425-018-0382-2 (2018).
Cancer Genome Atlas Research, "N. Integrated Genomic Analyses of Ovarian Carcinoma", Nature 474, 609-615, doi:10.1038/nature10166 (2011).
Cardenas, H., et. al."TGF-Beta Induces Global Changes in DNA Methylation During the Epithelial-to-mesenchymal Transition in Ovarian Cancer Cells", Epigenetics 9, 1461-1472, doi:10.4161/15592294.2014.971608 (2014).
Carlo, M. I., Voss, M. H. & Motzer, R. J., "Checkpoint Inhibitors and Other Novel Immunotherapies for Advanced Renal Cell Carcinoma", Nat Rev Urol 13, 420-431, doi: 10.1038/nrurol.2016.103 (2016).
Chang, C. C., et. al., "Multiple Structural and Epigenetic Defects in the Human Leukocyte Antigen Class I Antigen Presentation Pathway in a Recurrent Metastatic Melanoma Following Immunotherapy", J Biol Chem 290, 26562-26575, doi:10.1074/jbc.M115.676130 (2015).
Chen, D. S. & Mellman, I., "Elements of Cancer Immunity and the Cancer-immune Set Point", Nature 541, 321-330, doi:10.1038/nature21349 (2017).
Choi, H., Lee, R. H., Bazhanov, N., Oh, J. Y. & Prockop, D. J., "Anti-inflammatory Protein TSG-6 Secreted by Activated MSCs Attenuates Zymosan-induced Mouse Peritonitis by Decreasing TLR2/NF-kappaB Signaling in Resident Macrophages", Blood 118, 330-338, doi:10.1182/blood-2010-12-327353 (2011).
Czarniecki, C. W., Chiu, H. H., Wong, G. H., McCabe, S. M. & Palladino, M. A., "Transforming Growth Factor-beta 1 Modulates the Expression of Class II Histocompatibility Antigens on Human Cells", J Immunol 140, 4217-4223 (1988).
Dudley, J. C., Lin, M. T., Le, D. T. & Eshleman, J. R., "Microsatellite Instability as a Biomarker for PD-1 Blockade", Clin Cancer Res 22, 813-820, doi:10.1158/1078-0432.CCR-15-1678 (2016).
Fortin, J. P., et. al., "Functional Normalization of 450k Methylation Array Data Improves Replication in Large Cancer Studies", Genome Biol 15, 503, doi:10.1186/s13059-014-0503-2 (2014).

(Continued)

*Primary Examiner* — Elly-Gerald Stoica
(74) *Attorney, Agent, or Firm* — Kilpatrick Townsend & Stockton LLP

(57) ABSTRACT

A machine-learning model (e.g., a clustering model) may be used to predict a phenotype of a tumor based on expression levels of a set of genes. The set of genes may have been identified using a same or different machine-learning model. The phenotype may include an immune-excluded, immune-desert or an inflamed/infiltrated phenotype. A treatment strategy and/or treatment recommendation may be identified based on the predicted phenotype.

14 Claims, 17 Drawing Sheets
(13 of 17 Drawing Sheet(s) Filed in Color)

(56) References Cited

PUBLICATIONS

Geiser, A. G., et.al. "Transforming Growth Factor Beta 1 (TGF-beta 1) Controls Expression of Major Histocompatibility Genes in the Postnatal Mouse: Aberrant Histocompatibility Antigen Expression in the Pathogenesis of the TGF-beta 1 Null Mouse Phenotype". Proc Natl Acad Sci U S A 90, 9944-9948 (1993).

Germano, G., Amirouchene-Angelozzi, N., Rospo, G. & Bardelli, A., "The Clinical Impact of the Genomic Landscape of Mismatch Repair-Deficient Cancers", Cancer Discov 8, 1518-1528, doi:10.1158/2159-8290.CD-18-0150 (2018).

Hamanishi, J., Mandai, M. & Konishi, I., "Immune Checkpoint Inhibition in Ovarian Cancer", Int Immunol 28, 339-348, doi:10.1093/intimm/dxw020 (2016).

Hegde, P. S., Karanikas, V. & Evers, S., "The Where, the When, and the How of Immune Monitoring for Cancer Immunotherapies in the Era of Checkpoint Inhibition", Clin Cancer Res 22, 1865-1874, doi:10.1158/1078-0432.CCR-15-1507 (2016).

Herbst, R. S. et. al., "Predictive Correlates of Response to the Anti-PD-L1 Antibody MPDL3280A in Cancer Patients", Nature 515, 563-567, doi:10.1038/nature14011 (2014).

Januario, T., et. al., "PRC2-Mediated Repression of SMARCA2 Predicts EZH2 Inhibitor Activity in SWI/SNF Mutant Tumors", Proc Natl Acad Sci U S A 114, 12249-12254,doi:10.1073/pnas.1703966114 (2017).

Jiang, P., et. al., "Signatures of T Cell Dysfunction and Exclusion Predict Cancer Immunotherapy Response", Nat Med 24, 1550-1558, doi:10.1038/41591-018-0136-1 (2018).

Joyce, J. A. & Fearon, D. T. T, "Cell Exclusion, Immune Privilege, and the Tumor Microenvironment", Science 348, 74-80, doi:10.1126/science.aaa6204 (2015).

Kamat, A. M. et. al., "Society for Immunotherapy of Cancer Consensus Statement on Immunotherapy for the Treatment of Bladder Carcinoma", J Immunother Cancer 5, 68, doi:10.1186/s40425-017-0271-0 (2017).

Lawrence, M., et. al. "Software for Computing and Annotating Genomic Ranges", PLoS Comput Biol 9, e1003118, doi:10.1371/journal.pcbi.1003118 (2013).

Le, D. T., et. al., "Mismatch Repair Deficiency Predicts Response of Solid Tumors to PD-1 Blockade", Science 357, 409-413, doi:10.1126/science.aan6733 (2017).

Leone, P., et. al., "MHC Class I Antigen Processing and Presenting Machinery: Organization, Function, and Defects in Tumor Cells", J Natl Cancer Inst 105, 1172-1187, doi:10.1093/jnci/djt184 (2013).

Ma, D. & Niederkorn, J. Y., "Transforming Growth Factor-beta Down-regulates Major Histocompatibility Complex Class I Antigen Expression and Increases the Susceptibility of Uveal Melanoma Cells to Natural Killer Cell-Mediated Cytolysis". Immunology 86, 263-269 (1995).

Mariathasan, S. et. al. "TGFbeta Attenuates Tumour Response to PD-L1 Blockade by Contributing to Exclusion of T Cells", Nature 554, 544-548, doi:10.1038/nature25501 (2018).

McGranahan, N., et. al., "Clonal Neoantigens Elicit T Cell Immunoreactivity and Sensitivity to Immune Checkpoint Blockade",Science 351, 1463-1469, doi:10.1126/science.aaf1490 (2016).

Mellman, I., Coukos, G. & Dranoff, G., "Cancer Immunotherapy Comes of Age. Nature", 480, 480-489, doi:10.1038/nature10673 (2011).

Milner, C. M. & Day, A. J. TSG-6: "A Multifunctional Protein Associated with Inflammation", J Cell Sci 116, 1863-1873, doi:10.1242/jcs.00407 (2003).

Mittal, M., et. al., "TNFalpha-stimulated Gene-6 (TSG6) Activates Macrophage Phenotype Transition to Prevent Inflammatory Lung Injury", Proc Natl Acad Sci U S A 113, E8151-E8158, doi:10.1073/pnas.1614935113 (2016).

Oza, A. M., et. al., "Standard Chemotherapy With or Without Bevacizumab for Women with Newly Diagnosed Ovarian Cancer", (ICON7): overall survival results of a phase 3 randomised trial. Lancet Oncol 16, 928-936, doi:10.1016/S1470-2045(15)00086-8 (2015).

Paulson, K. G., et. al., "Acquired Cancer Resistance to Combination Immunotherapy from Transcriptional Loss of Class I HLA", Nat Commun 9, 3868, doi:10.1038/s41467-018-06300-3 (2018).

Pennington, K. P., et. al., "Germline and Somatic Mutations in Homologous Recombination Genes Predict Platinum Response and Survival in Ovarian, Fallopian Tube, and Peritoneal Carcinomas", Clin Cancer Res 20, 764-775, doi:10.1158/1078-0432.CCR-13-2287 (2014).

Perea, F., et. al., "HLA Class I Loss and PD-L1 Expression in Lung Cancer: Impact on T-cell Infiltration and Immune Escape", Oncotarget 9, 4120-4133, doi:10.18632/oncotarget.23469 (2018).

Perren, T. J., et. al., "A Phase 3 Trial of Bevacizumab in Ovarian Cancer", N Engl J Med 365, 2484-2496, doi:10.1056/NEJMoa1103799 (2011).

Ryner, L., et. al., "Upregulation of Periostin and Reactive Stroma Is Associated with Primary Chemoresistance and Predicts Clinical Outcomes in Epithelial Ovarian Cancer", Clin Cancer Res 21, 2941-2951, doi:10.1158/1078-0432.CCR-14-3111 (2015).

Sadozai, H., Gruber, T., Hunger, R. E. & Schenk, M., "Recent Successes and Future Directions in Immunotherapy of Cutaneous Melanoma", Front Immunol 8, 1617, doi:10.3389/fimmu.2017.01617 (2017).

Schmidt, H., et. al, "Differential Regulation of HLA Class I Genes by Interferon", Immunogenetics 31, 245-252 (1990).

Shukla, S. A., et. al., "Comprehensive Analysis of Cancer-Associated Somatic Mutations in Class I HLA Genes", Nat Biotechnol 33, 1152-1158, doi:10.1038/nbt.3344 (2015).

Smith, M. L., Baggerly, K. A., Bengtsson, H., Ritchie, M. E. & Hansen, K. D. illuminaio "An Open Source IDAT Parsing Tool for Illumina Microarrays", F1000Res 2, 264, doi:10.12688/f1000research.2-264.v1 (2013).

Spranger, S., Bao, R. & Gajewski, T. F., "Melanoma-intrinsic Beta-catenin Signalling Prevents Anti-tumour Immunity", Nature 523, 231-235, doi:10.1038/nature14404 (2015).

Subramanian, A., et. al., "Gene Set Enrichment Analysis: a Knowledge-Based Approach for Interpreting Genome-wide Expression Profiles", Proc Natl Acad Sci U S A 102, 15545-15550, doi:10.1073/pnas.0506580102 (2005).

Tauriello, D. V. F., et. al., "TGFbeta Drives Immune Evasion in Genetically Reconstituted Colon Cancer Metastasis", Nature 554, 538-543, doi:10.1038/nature25492 (2018).

Thorsson, V., et. al., "The Immune Landscape of Cancer", Immunity 48, 812-830 e814, doi:10.1016/j.immuni.2018.03.023 (2018).

Tibshirani, R., Hastie, T., Narasimhan, B. & Chu, G., "Diagnosis of Multiple Cancer Types by Shrunken Centroids of Gene Expression", Proc Natl Acad Sci U S A 99, 6567-6572, doi:10.1073/pnas.082099299 (2002).

Tothill, R. W., et. al., "Novel Molecular Subtypes of Serous and Endometrioid Ovarian Cancer Linked to Clinical Outcome", Clin Cancer Res 14, 5198-5208, doi:10.1158/1078-0432.CCR-08-0196 (2008).

Triche, T. J., Jr., Weisenberger, D. J., Van Den Berg, D., Laird, P. W. & Siegmund, K. D. "Low-level Processing of Illumina Infinium DNA Methylation BeadArrays. Nucleic Acids", Res 41, e90, doi:10.1093/nar/gkt090 (2013).

Verhaak, R. G et al. "Prognostically Relevant Gene Signatures of High-grade Serous Ovarian Carcinoma", J Clin Invest 123, SI 7-S2S, (2013).

Verhaak, R. G., et. al., "Prognostically Relevant Gene Signatures of High-Grade Serous Ovarian Carcinoma", J Clin Invest 123, 517-525, doi: 10.1172/JCI65833 (2013).

Wiebke, E. A., Custer, M. C., Rosenberg, S. A. & Lotze, M. T. "Cytokines Alter Target Cell Susceptibility to Lysis: I. Evaluation of Non-major Histocompatibility Complex-Restricted Effectors Reveals Differential Effects on Natural and Lymphokine-activated Killing", J Biol Response Mod 9, 113-126 (1990).

Wu, T. D. & Nacu, S. "Fast and SNP-tolerant Detection of Complex Variants and Splicing in Short Reads", Bioinformatics 26, 873-881, doi: 10.1093/bioinformatics/btq057 (2010).

(56) References Cited

PUBLICATIONS

Wu, T. D., Reeder, J., Lawrence, M., Becker, G. & Brauer, M. J, "GMAP and GSNAP for Genomic Sequence Alignment: Enhancements to Speed, Accuracy, and Functionality", Methods Mol Biol 1418, 283-334, doi:10.1007/978-1-4939-3578-9_15 (2016).
Xing, D. & Orsulic, S., "A Mouse Model for the Molecular Characterization of brca1-associated Ovarian Carcinoma", Cancer Res 66, 8949-8953, doi:10.1158/0008-5472.CAN-06-1495 (2006).
Zaretsky, J. M., et. al., "Mutations Associated with Acquired Resistance to PD-1 Blockade in Melanoma" N Engl J Med 375, 819-829, doi:10.1056/NEJMoa1604958 (2016).

* cited by examiner

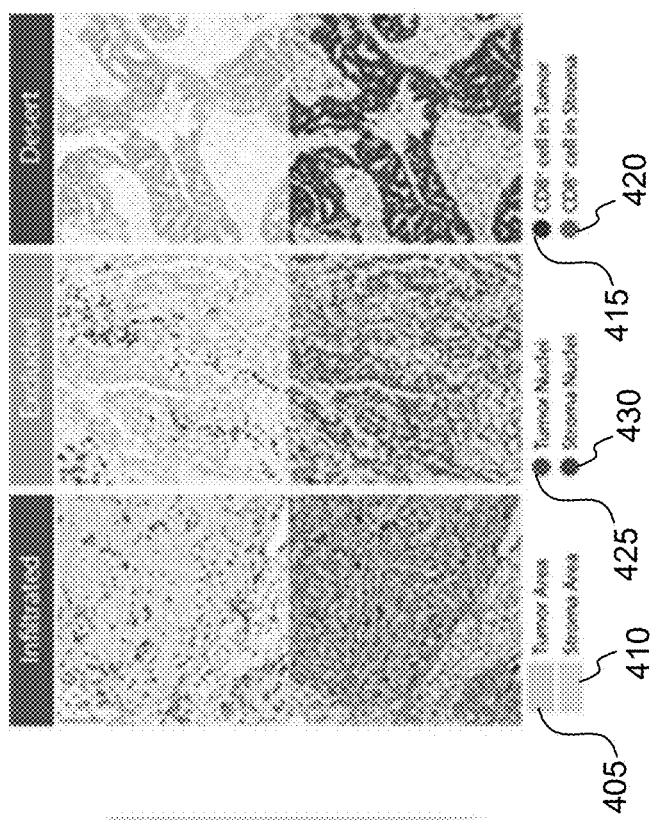
FIG. 4c
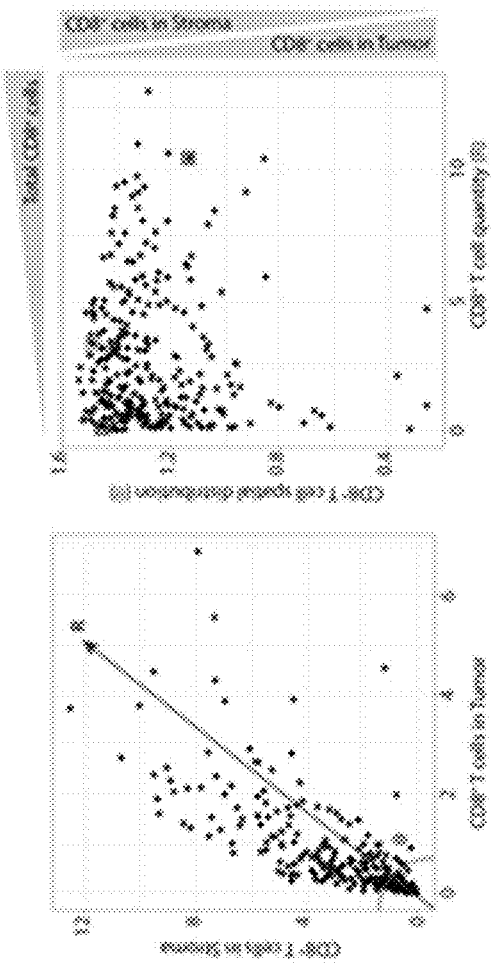
FIG. 4b
FIG. 4a

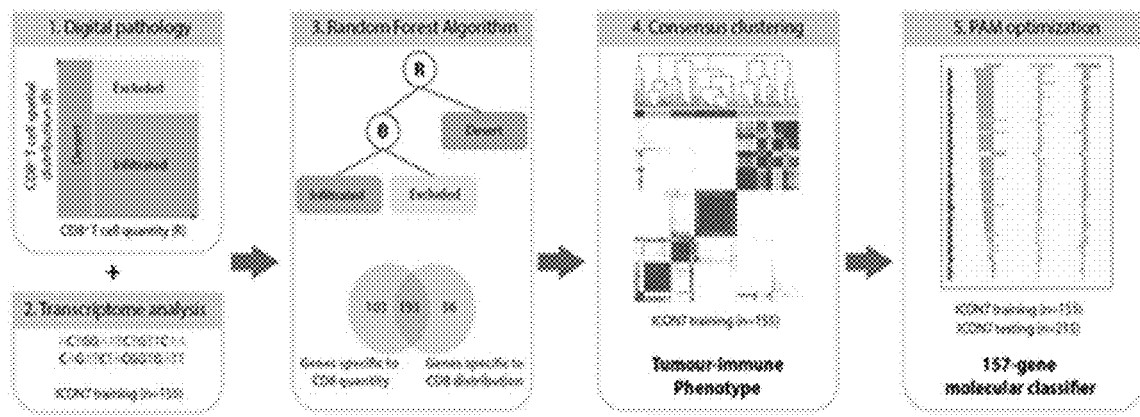
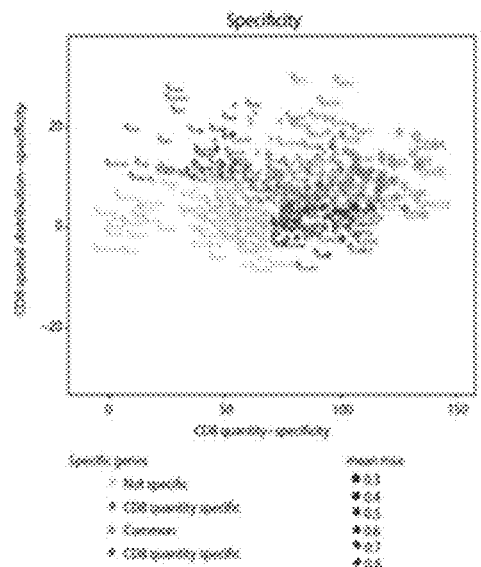
FIG. 5a
FIG. 5b
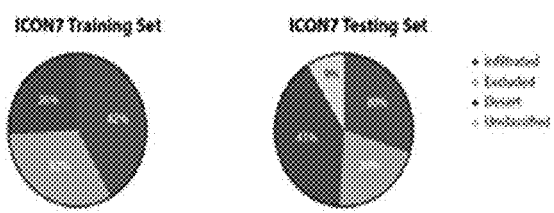
FIG. 5c
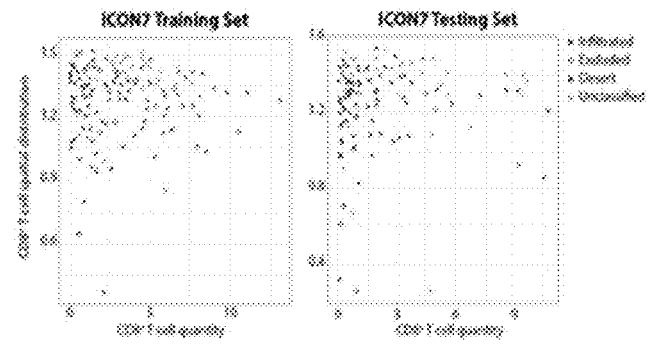
FIG. 5d
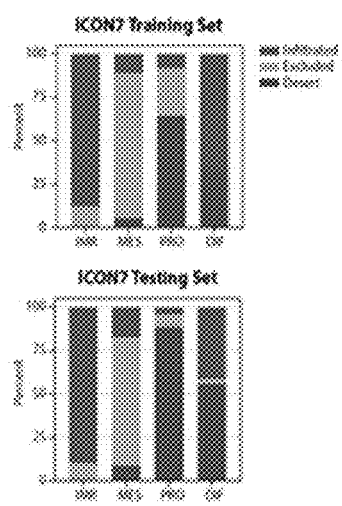
FIG. 5e
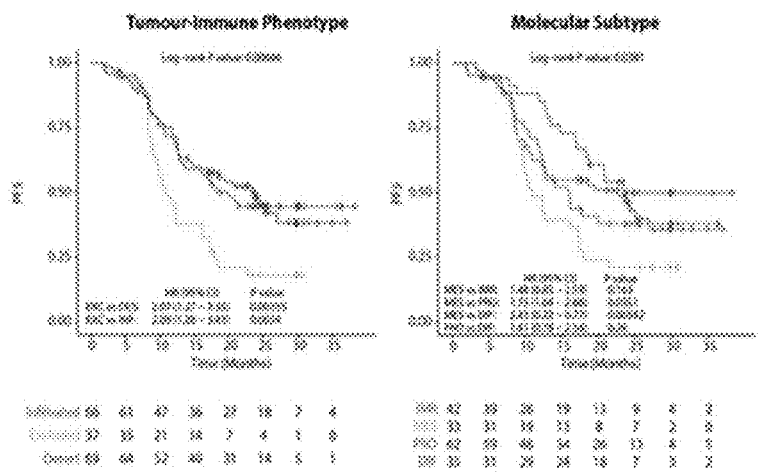
FIG. 5f

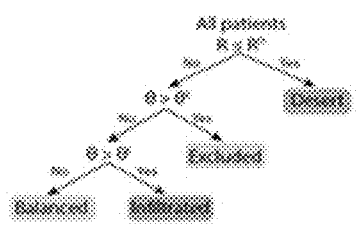
FIG. 6a     FIG. 6b
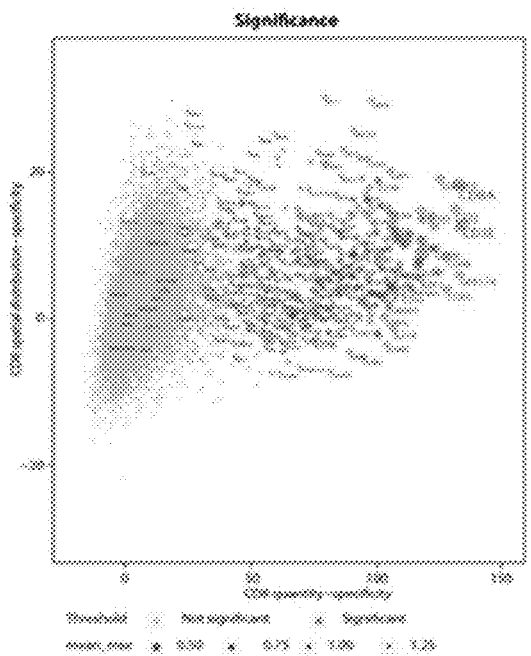
FIG. 6c
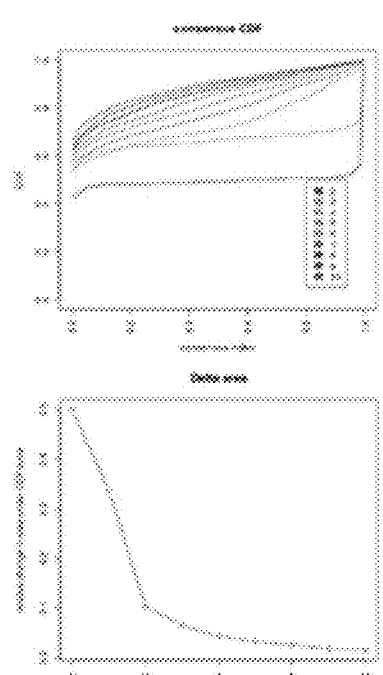
FIG. 6d
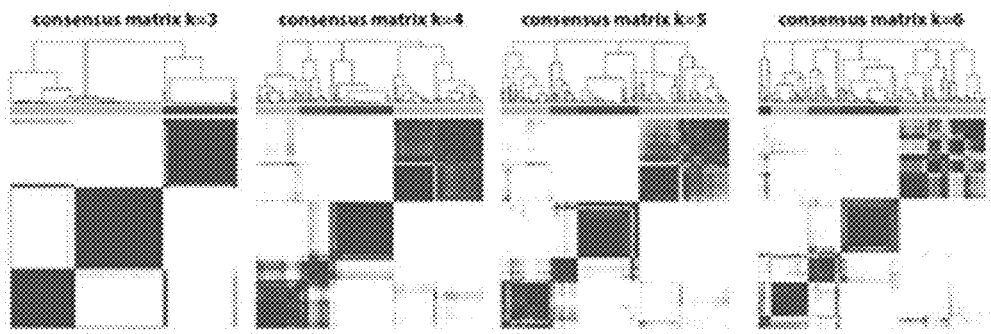
FIG. 6e
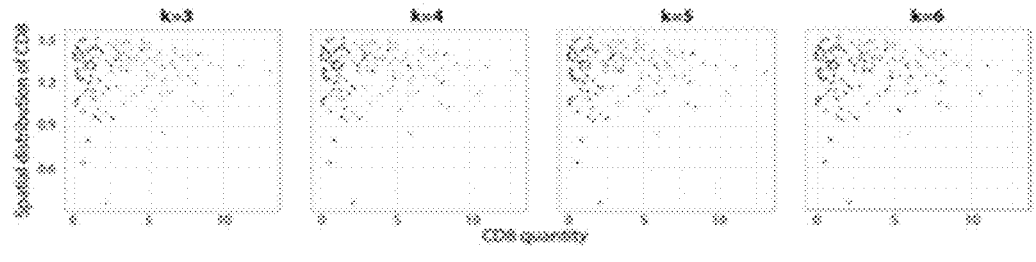
FIG. 6f

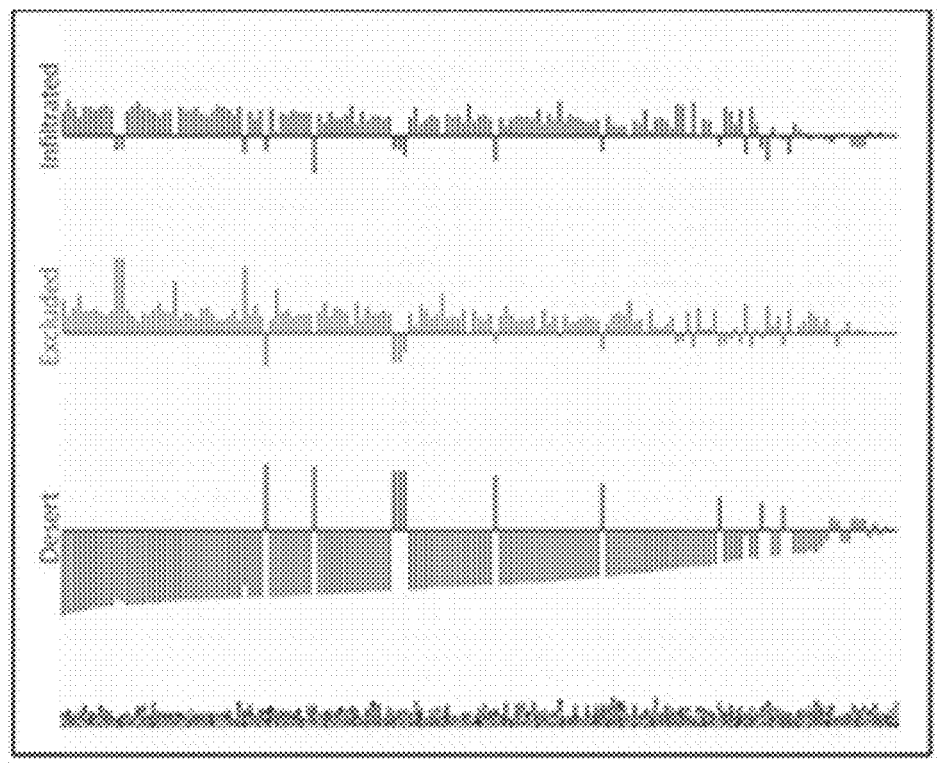
FIG. 7b
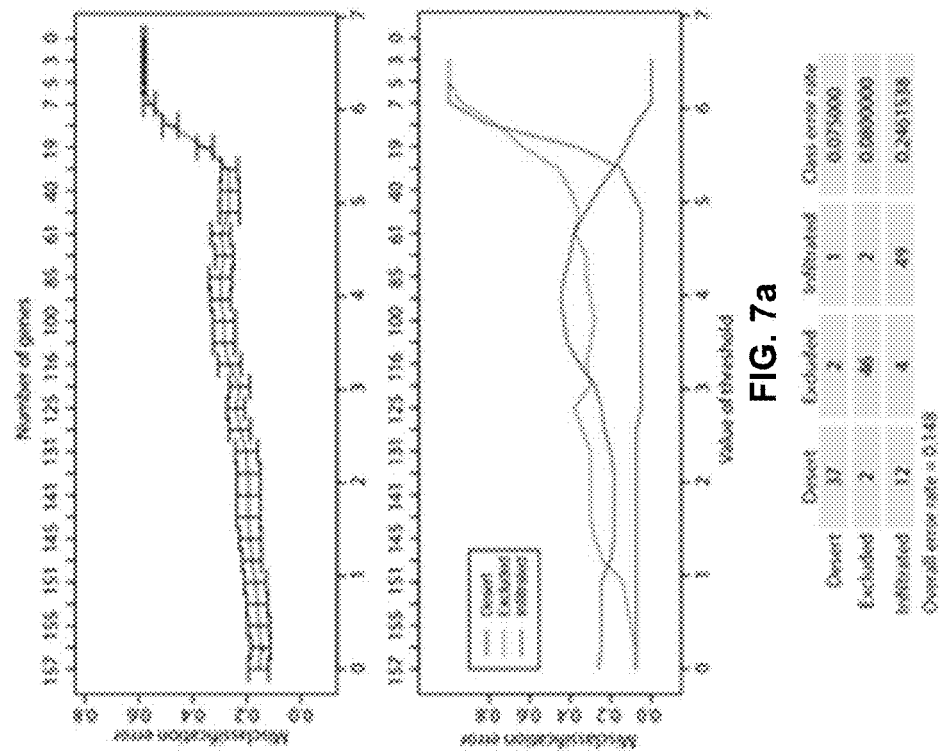
FIG. 7a
FIG. 7c
FIG. 7d

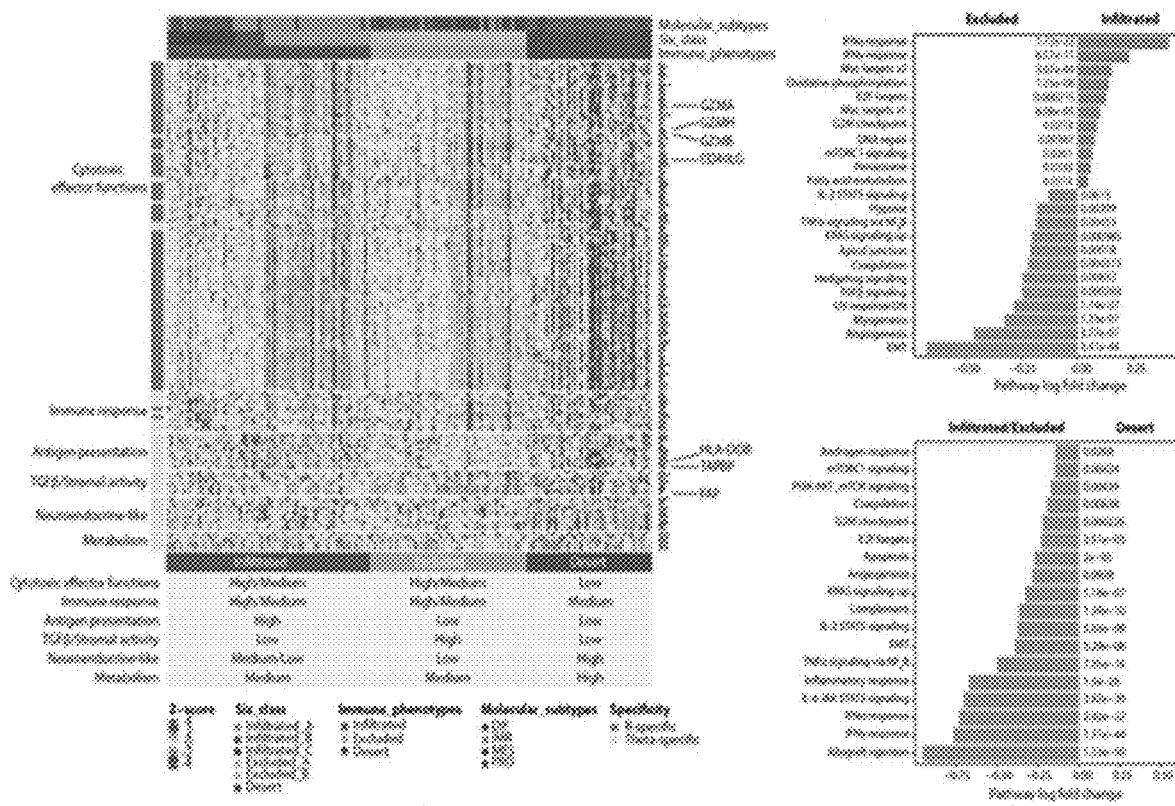
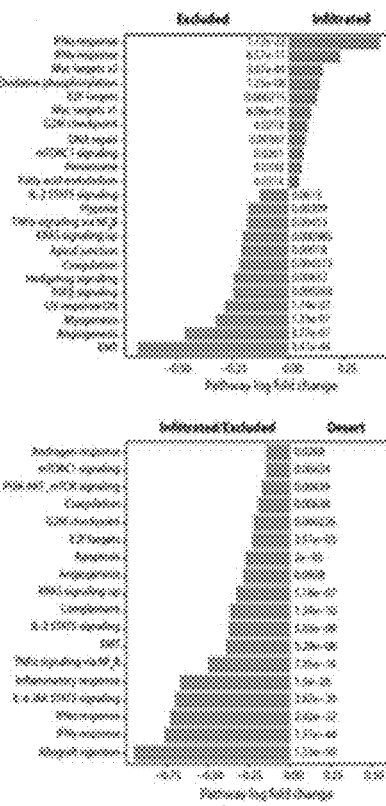
FIG. 8a  FIG. 8b
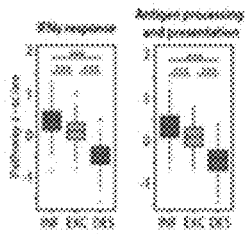
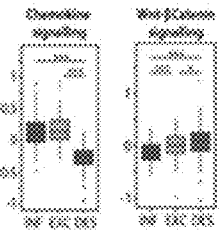
FIG. 8c  FIG. 8d
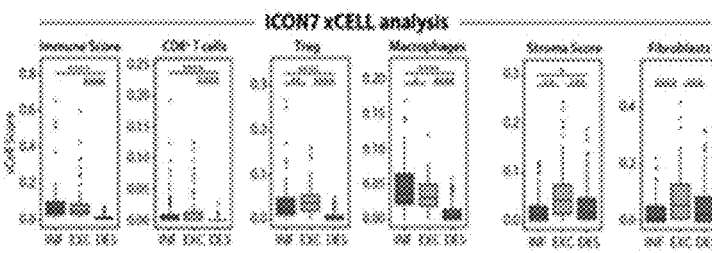
FIG. 8e
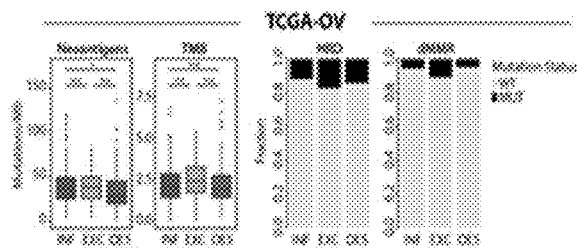
FIG. 8f

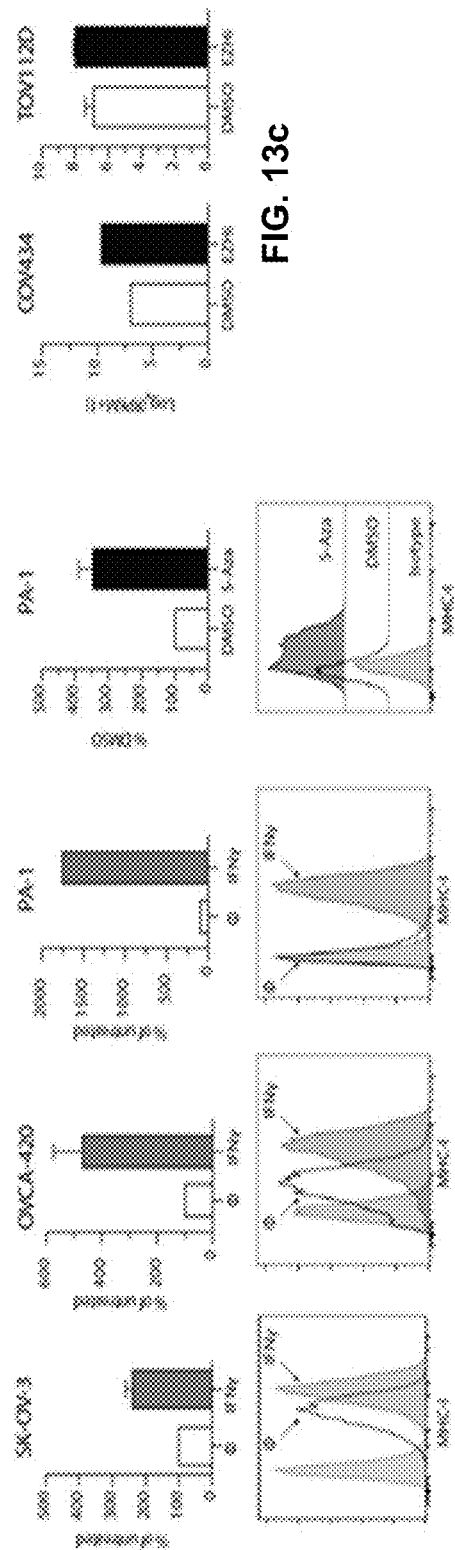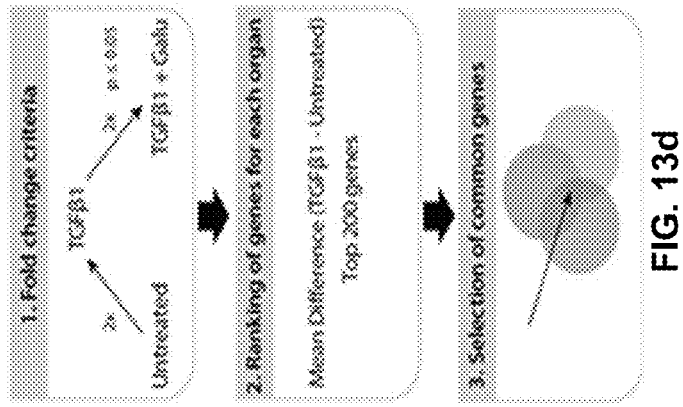

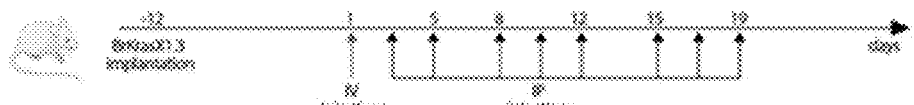
FIG. 14a
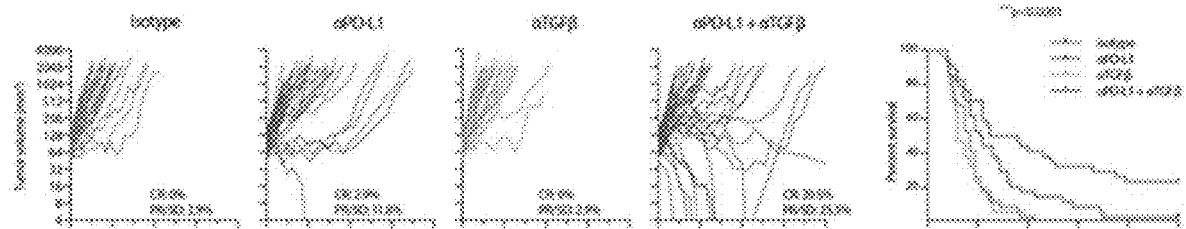
FIG. 14b  FIG. 14c
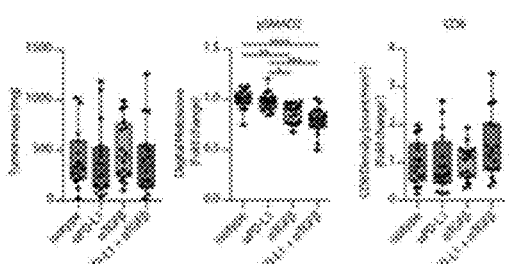
FIG. 14d  FIG. 14e
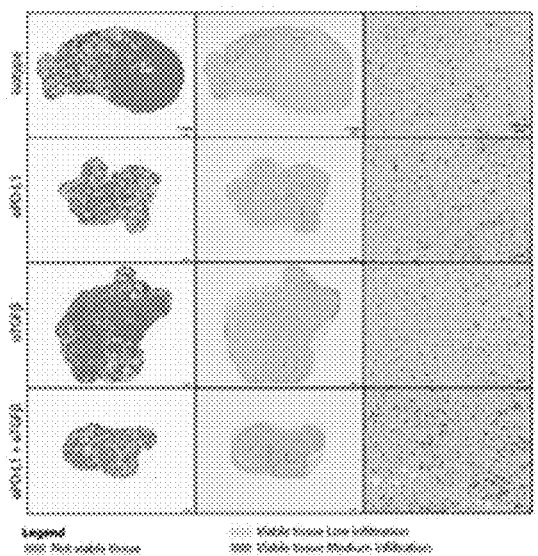
FIG. 14f
FIG. 14g
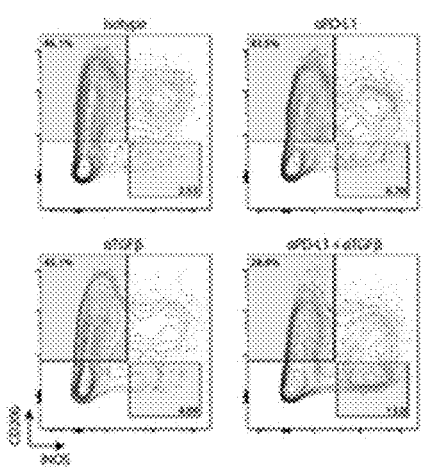
FIG. 14h
FIG. 14i
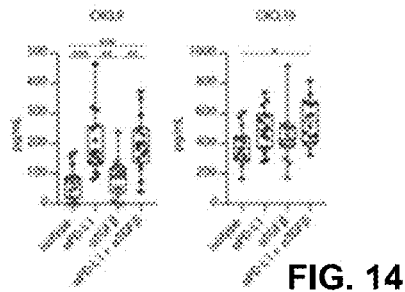
FIG. 14j

CD8+ T CELL BASED IMMUNOSUPPRESSIVE TUMOR MICROENVIRONMENT DETECTION METHOD

CROSS-REFERENCE TO RELATED APPLICATIONS

This application claims priority to and the benefit of U.S. Provisional Application No. 62/907,062, filed on Sep. 27, 2019, which is hereby incorporated by reference in its entirety for all purposes.

FIELD

Systems and methods relate to using expression levels for a set of genes in order to identify a phenotype of a tumor and to identify a treatment candidate based on the phenotype (e.g., a treatment candidate that includes an anti-TGFβ agent when the phenotype is immune-excluded). The set of genes can include genes predictive of digital-pathology characteristics of CD8+ T cells (e.g., in terms of quantity and/or spatial location).

BACKGROUND

Clinical success of cancer immunotherapies such as immune checkpoint inhibitors has revolutionized traditional cancer treatment. By targeting the immune checkpoint regulators including CTLA-4 and the PD-1/PD-L1 axis, these immunotherapies promote cytotoxic killing of cancer cells by enhancing the function of effector T cells. Despite impressive efficacy demonstrated in subsets of patients with melanoma, NSCLC, urothelial bladder cancer, and renal cell cancer, significant challenges still exist in this field. Dramatic and durable responses were mainly observed in subsets of patients with a pre-existing T cell immunity in tumors. As such, other steps in the tumor immunity cycle may influence the effectiveness of immunotherapies based on checkpoint blockade. These include antigen presentation and T cell priming, capacity of tumor infiltration by functional CD8+ T effector cells, as well as accumulation of immunoregulatory mechanisms that evolved to protect tissue integrity from exuberant immune responses. Overcoming mechanisms that impede immune activation may thus enhance the potential of cancer immunotherapy.

CD8+ T cells are the main players in eradicating cancer cells in most of the immunotherapy settings. CD8+ T cells recognize tumor-associated antigens through the MHC class I/T cell receptor complex and mediate cytotoxic killing of tumor cells. Given that effective cytotoxic killing requires direct contact between CD8+ T cells and tumor cells, it has been increasingly recognized that different CD8+ T cell distributions in the tumor microenvironment (TME) may elicit different responses to immunotherapies.

Three basic tumor-immune phenotypes have been described previously, including 1) the inflamed/infiltrated phenotype in which CD8+ T cells infiltrate the tumor epithelium; 2) the immune excluded phenotype in which infiltrating CD8+ T cells accumulate in the tumor stroma rather than the tumor epithelium, and 3) the immune desert phenotype in which CD8+ T cells are either absent or present in very low numbers. These histologically established tumor-immune phenotypes provided a useful framework to profile immune contexture in solid tumors. However, it remains challenging to systematically define the tumor-immune phenotype of most cancer patients due to the highly heterogeneous and complex nature of immune cell infiltration and distribution. Further, the molecular features and mechanisms that shape spatial distribution of tumor-infiltrating CD8+ T cells are not well understood.

SUMMARY

In some embodiments, systems and methods use a machine-learning approach to classify and molecularly characterize tumor-immune phenotypes. This approach can be used to detect previously undiscovered molecular features that are associated with distinct immune phenotypes. More specifically, a classifier can be configured to receive a data set that includes expression levels corresponding to a pre-identified set of genes and to output a label that corresponds to a tumor-immune phenotype. The classifier can use the Prediction Analysis of Microarrays. The pre-identified set of genes may include at least 1, at least 10, at least 50, at least 100 or at least 120 of the genes in Table 1. The tumor-immune phenotype can include one of: immune-desert phenotype, an immune-excluded phenotype or an inflamed/infiltrated phenotype.

The pre-identified set of genes can include and/or can contain genes for which expression levels are specific to and/or significantly related to CD8+ T-cell characteristics detectable by using pathology images. The CD8+ T-cell characteristics can include a quantity of CD8+ T cells and/or can correspond to locations of CD8+ T cells (e.g., a quantity of CD8+ T cells in the tumor epithelium, a quantity of CD8+ T cells in the stroma, a proportion of CD8+ T cells in the tumor epithelium, a proportion of CD8+ T cells in the stroma, etc.). A machine-learning model (e.g., regression and/or random-forest model) may be used to determine which gene expression levels are related to CD8+ T-cell characteristics.

The label identified by the classifier for a given data set can be used to identify a treatment candidate. For example, the treatment candidate may include anti-TGFβ (and potentially also a checkpoint inhibitor, such as anti-PD-L1) when the phenotype is identified as an immune-excluded phenotype. As another example, the treatment candidate may include a checkpoint inhibitor (and lack anti-TGFβ) when the phenotype is identified as an inflamed/infiltrated phenotype. The treatment candidate can be identified by performing a look-up process using an identifier of the phenotype. In some instances, multiple treatment candidates are identified.

An output can be generated to include an identification of the particular phenotype, the treatment candidate(s) and/or an identification of a subject associated with the new expression-level data set. The output can be presented locally and/or transmitted to another device.

In some instances, the machine-learning approach can include performing an additional clustering (e.g., consensus clustering) using some or all of the training data in order to detect molecular features of individual phenotypes. The additional clustering may include accessing a data set that includes, for each of a set of subjects, an expression level of each of multiple gene determined to be specific to a quantity or spatial distribution of CD8+ T cells. The additional clustering may be configured such that there are more clusters than there are phenotype labels. Each of the clusters may be nonetheless associated with a given phenotype label (e.g., and used to generate a molecular profile (based on expression levels associated with the cluster) for the cluster. Thus, for a given phenotype label, the additional clustering can generate one or more molecular profiles that can be used identify (for example) treatment candidates for the phenotype (e.g., which may be generally associated with the phenotype label or may be associated with a specific cluster).

In some embodiments, a method of treatment is provided that includes targeting the TGFβ pathway. It has been discovered, through implementation of the machine-learning approach, that the cytokine, TGFβ is a molecular mediator in promoting CD8+ T cell exclusion and immune suppression via a crosstalk with both tumor cells and tumor stroma (at least in some contexts, such as for ovarian cancer). Thus, targeting the TGFβ pathway may overcome T cell exclusion from tumors and improve subjects' response to cancer immunotherapy.

In some embodiments, a computer-implemented method is provided that includes accessing gene expression data for a predefined set of genes, the gene expression data corresponding to a subject. For each gene in the predefined set of genes, an expression level of the gene may have been identified as being informative of a quantity of CD8+ cells associated with a tumor of the subject and/or a spatial distribution of CD8+ cells. The method includes generating a cluster assignment using the gene expression data; determining that the cluster assignment corresponds to a particular phenotype; and outputting a result based on the particular phenotype.

The spatial distribution of CD8+ cells may be computed from a first quantity of CD8+ cells located in a tumor epithelium in the subject and a second quantity of CD8+ cells located in a tumor stroma in the subject, each of the first quantity and the second quantity having been determined based on an assessment of one or more digital pathology images. The particular phenotype may include an immune-desert phenotype, immune-excluded phenotype or an inflamed/infiltrated phenotype. The predefined set of genes may have been identified using a machine-learning model (e.g., a regression model or a random-forest regression model). The method may further include selecting one or more treatment candidates based on the particular phenotype, wherein the result identifies the one or more treatment candidates. The particular phenotype may include an immune-excluded phenotype, and the one or more treatment candidates may include anti-TGFβ. The predefined set of genes may include at least one of GZMA, GZMB, GMZH, CD40LG, TAPBP, PSMB10, HLA-DOB, FAP, TDO2, LRRTM3, ASTN1, SLC4A4, UGT1A3, UGT1A5, and UGT1A6. The predefined set of genes may include at least five genes identified in Table 1. The predefined set of genes includes at least one gene identified in rows 1-56 of Table 1, at least one gene identified in rows 57-244 of Table 1 and/or at least one gene identified in rows 245-346 of Table 1. The result may identify the particular phenotype.

In some embodiments, a method of treatment is provided that includes identifying a subject with a tumor; determining that the tumor corresponds to an immune excluded phenotype; and prompting administration of anti-TGFβ to the subject (or administering anti-TGFβ to the subject). An amount of anti-TGFβ administered may be sufficient to result in a promotion of MHC class I expression in cancer cells of the tumor. An amount of anti-TGFβ administered may be sufficient to result in suppression of extracellular matrix production by cancer-associated fibroblasts associated with the tumor. An amount of anti-TGFβ administered may be sufficient to result in suppression of production of immunosuppressive molecules by cancer-associated fibroblasts associated with the tumor. The method may further include prompting administration of (or administering) a checkpoint inhibitor to the subject, where an amount of anti-TGFβ administered and an amount of checkpoint inhibitor administered may be collectively sufficient to enhance cytotoxic activity of effector T cells in the subject. The checkpoint inhibitor includes anti-PD-L1. Determining that the tumor corresponds to the immune excluded phenotype may include: accessing one or more digital pathology images corresponding to the subject; determining, based on the one or more digital pathology images, a first quantity of CD8+ cells located in a tumor epithelium in the subject; determining, based on the one or more digital pathology images, a second quantity of CD8+ cells located in a tumor stroma in the subject; generating a distribution metric based on the first quantity and second quantity; and determining that the distribution metric exceeds a predefined threshold. Determining that the tumor corresponds to the immune excluded phenotype may include: accessing gene expression data for a predefined set of genes, the gene expression data corresponding to the subject; generating a cluster assignment using the gene expression data; and determining that the cluster assignment corresponds to the immune excluded phenotype. The predefined set of genes may include at least five genes identified in Table 1.

In some embodiments, a system is provided that includes one or more data processors and a non-transitory computer readable storage medium containing instructions which, when executed on the one or more data processors, cause the one or more data processors to perform part or all of one or more methods disclosed herein.

In some embodiments, a computer-program product is provided that is tangibly embodied in a non-transitory machine-readable storage medium and that includes instructions configured to cause one or more data processors to perform part or all of one or more methods disclosed herein.

Some embodiments of the present disclosure include a system including one or more data processors. In some embodiments, the system includes a non-transitory computer readable storage medium containing instructions which, when executed on the one or more data processors, cause the one or more data processors to perform part or all of one or more methods and/or part or all of one or more processes disclosed herein. Some embodiments of the present disclosure include a computer-program product tangibly embodied in a non-transitory machine-readable storage medium, including instructions configured to cause one or more data processors to perform part or all of one or more methods and/or part or all of one or more processes disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention as claimed has been specifically disclosed by embodiments and optional features, modification and variation of the concepts herein disclosed may be resorted to by those skilled in the art, and that such modifications and variations are considered to be within the scope of this invention as defined by the appended claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present disclosure is described in conjunction with the appended figures:

FIGS. 4a-4c illustrate a novel digital image analysis algorithm to quantify the quantity and the spatial distribution of $CD8^+$ T cells in ovarian cancer and exemplary $CD8^+$ T-cell distributions associated with distinct immune phenotypes.

FIGS. 5a-5f illustrate characteristics of a gene-expression based molecular classifier for predicting the immune phenotypes in ovarian cancer and exemplary predictions generated using the classifier.

FIGS. 6a-6f illustrate assessments performed to identify genes associated with CD8 quantity and/or CD8 spatial distribution using Random Forest and consensus clustering analysis and exemplary resulting phenotype predictions.

FIGS. 7a-7d show exemplary results of Using a PAMR classifier analysis to derive a classifier for the prediction of the three immune phenotypes.

FIGS. 8a-8f illustrate molecular features characterizing distinct tumor-immune phenotypes.

FIGS. 13a-13d show exemplary results and predictions relating MHC class I expression and epigenetic regulation and characterizing a multi-faceted role of TGFβ in ovarian cancer tumor microenvironment.

FIGS. 14a-14j show exemplary results indicating that anti-TGFβ improves the efficacy of anti-PD-L1 in an immunocompetent mouse ovarian cancer model and techniques performed to arrive at the results.

Figure 1:
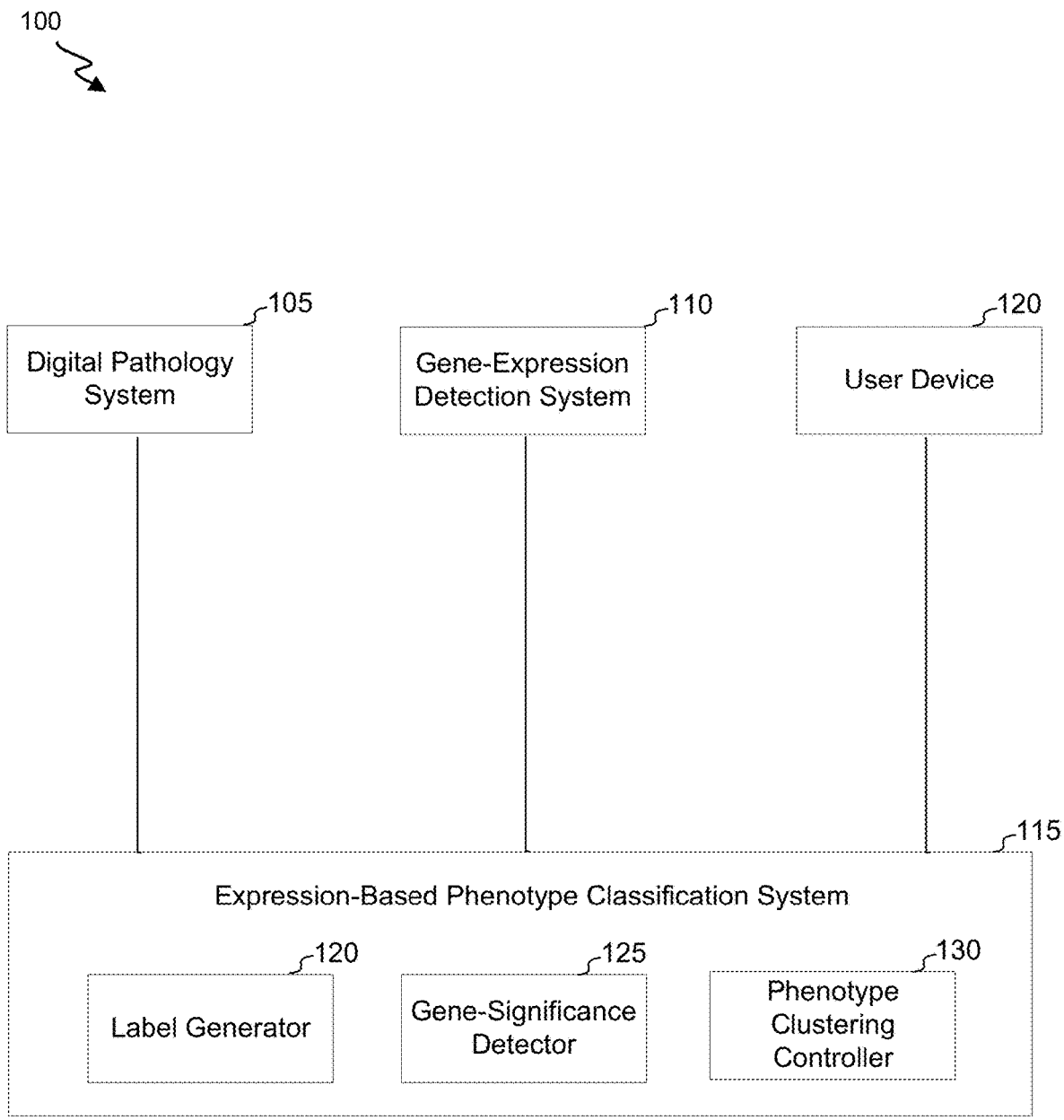
FIG. 1 shows an exemplary interaction system for generating and processing digital-pathology images to characterize relative spatial information of biological objects according to some embodiments.

In the appended figures, similar components and/or features can have the same reference label. Further, various components of the same type can be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

I. Overview

Systems and methods disclosed herein can generate and use quantitative metrics for characterizing immune phenotypes. The metrics can characterize a quantity and spatial distribution of a given cell type as determined by processing immunohistochemistry images. A particular use case is to generate and use these metrics to characterize ovarian cancer.

In some embodiments, gene-expression data are accessed (e.g., received from a computing system associated with a laboratory or care-provider office) and used to predict a tumor-immune phenotype. The prediction may be generated using a computing system that is co-located with and/or includes the computing system associated with the laboratory or care-provider office and/or using a computing system that is remote from the computing system associated with the laboratory or computing system. For example, the prediction may be generated using a cloud computing system (e.g., that includes one or more servers, one or more processors and/or one or more memories).

The phenotype prediction can be generated using a machine-learning model, such as a classifier. The gene-expression data can identify expression levels of one or more genes in Table 1 (e.g., at least 1, at least 10, at least 50, at least 100 or at least 120 of the genes in Table 1) and/or one or more genes for which expression levels correlate with and/or are predictive of a quantity, spatial distribution and/or locations of $CD8^+$ T cells. The gene-expression data can identify expression levels for a set of genes. The set of genes may include one or more genes (e.g., or 5 or more, 10 or more, 20 or more or 50 or more) for which expression levels are correlated with, predictive of, and/or informative as to CD8+ T cell spatial distribution. The set of genes may include one or more genes (e.g., or 5 or more, 10 or more, 20 or more or 50 or more) for which expression levels are correlated with, predictive of, and/or informative as to CD8+ T cell quantity. The set of genes can include at least 1 gene, at least 10 genes, at least 20 genes or at least 50 genes of genes identified in Rows 1-56 of Table 1; at least 1 gene, at least 10 genes, at least 20 genes or at least 50 genes of genes identified in Rows 57-244 of Table 1 and/or at least 1 gene, at least 10 genes, at least 20 genes or at least 50 genes of genes identified in Rows 245-346 of Table 1.

TABLE 1

| Row # | Gene Symbol | Specific for CD8+ T Cell Quantity? | Specific for CD8+ T Cell Spatial Distribution? | Common for CD8+ T Cell Quantity and Distribution? |
|---|---|---|---|---|
| 1 | CXCR6 | No | Yes | No |
| 2 | UNC80 | No | Yes | No |
| 3 | FXN | No | Yes | No |
| 4 | ARMCX6 | No | Yes | No |
| 5 | FAP | No | Yes | No |
| 6 | AKNA | No | Yes | No |
| 7 | TRIM14 | No | Yes | No |
| 8 | PARP12 | No | Yes | No |
| 9 | SAMD9 | No | Yes | No |
| 10 | KLRC2 | No | Yes | No |

TABLE 1-continued

| Row # | Gene Symbol | Specific for CD8+ T Cell Quantity? | Specific for CD8+ T Cell Spatial Distribution? | Common for CD8+ T Cell Quantity and Distribution? |
|---|---|---|---|---|
| 11 | ZSWIM5 | No | Yes | No |
| 12 | TNFRSF8 | No | Yes | No |
| 13 | LRRTM3 | No | Yes | No |
| 14 | P2RY13 | No | Yes | No |
| 15 | LRRC18 | No | Yes | No |
| 16 | IL15RA | No | Yes | No |
| 17 | BMP2K | No | Yes | No |
| 18 | JAK3 | No | Yes | No |
| 19 | RCN3 | No | Yes | No |
| 20 | NOD2 | No | Yes | No |
| 21 | UGT1A6 | No | Yes | No |
| 22 | RIPK1 | No | Yes | No |
| 23 | TDO2 | No | Yes | No |
| 24 | CECR1 | No | Yes | No |
| 25 | ASTN1 | No | Yes | No |
| 26 | JAKMIP1 | No | Yes | No |
| 27 | AGAP2 | No | Yes | No |
| 28 | HLA-DOB | No | Yes | No |
| 29 | PTCH2 | No | Yes | No |
| 30 | PSMB10 | No | Yes | No |
| 31 | EAF2 | No | Yes | No |
| 32 | PLXNC1 | No | Yes | No |
| 33 | VSTM4 | No | Yes | No |
| 34 | ZCCHC24 | No | Yes | No |
| 35 | TAPBP | No | Yes | No |
| 36 | NME9 | No | Yes | No |
| 37 | NLRC3 | No | Yes | No |
| 38 | EFNA4 | No | Yes | No |
| 39 | C16orf71 | No | Yes | No |
| 40 | MX1 | No | Yes | No |
| 41 | UGT1A5 | No | Yes | No |
| 42 | DTX3L | No | Yes | No |
| 43 | CCR7 | No | Yes | No |
| 44 | MICAL1 | No | Yes | No |
| 45 | BMP4 | No | Yes | No |
| 46 | ADGRG5 | No | Yes | No |
| 47 | PRRT1 | No | Yes | No |
| 48 | UGT1A3 | No | Yes | No |
| 49 | ICAM3 | No | Yes | No |
| 50 | SLC4A4 | No | Yes | No |
| 51 | CMIP | No | Yes | No |
| 52 | BLOC1S2 | No | Yes | No |
| 53 | INHBA | No | Yes | No |
| 54 | VNN2 | No | Yes | No |
| 55 | CYTH1 | No | Yes | No |
| 56 | NTM | No | Yes | No |
| 57 | CD8A | No | No | Yes |
| 58 | CD3E | No | No | Yes |
| 59 | CD2 | No | No | Yes |
| 60 | CD3D | No | No | Yes |
| 61 | PYHIN1 | No | No | Yes |
| 62 | ITK | No | No | Yes |
| 63 | CD96 | No | No | Yes |
| 64 | THEMIS | No | No | Yes |
| 65 | SLAMF6 | No | No | Yes |
| 66 | TRAT1 | No | No | Yes |
| 67 | GPR174 | No | No | Yes |
| 68 | CD48 | No | No | Yes |
| 69 | SLAMF7 | No | No | Yes |
| 70 | CXCL9 | No | No | Yes |
| 71 | ICOS | No | No | Yes |
| 72 | ZNF831 | No | No | Yes |
| 73 | ITGAL | No | No | Yes |
| 74 | IKZF1 | No | No | Yes |
| 75 | SLAMF1 | No | No | Yes |
| 76 | ARRDC5 | No | No | Yes |
| 77 | TRAF3IP3 | No | No | Yes |
| 78 | GRAP2 | No | No | Yes |
| 79 | CD247 | No | No | Yes |
| 80 | GZMK | No | No | Yes |
| 81 | BIN2 | No | No | Yes |
| 82 | PRF1 | No | No | Yes |
| 83 | LY9 | No | No | Yes |
| 84 | SLFN12L | No | No | Yes |
| 85 | IL10RA | No | No | Yes |
| 86 | P2RY10 | No | No | Yes |
| 87 | PARP15 | No | No | Yes |
| 88 | DOCK2 | No | No | Yes |
| 89 | UBASH3A | No | No | Yes |
| 90 | GBP5 | No | No | Yes |
| 91 | CD3G | No | No | Yes |
| 92 | CTLA4 | No | No | Yes |
| 93 | RASAL3 | No | No | Yes |
| 94 | SH2D1A | No | No | Yes |
| 95 | TBX21 | No | No | Yes |
| 96 | ZAP70 | No | No | Yes |
| 97 | IL2RB | No | No | Yes |
| 98 | PIK3CG | No | No | Yes |
| 99 | GBP1 | No | No | Yes |
| 100 | ARHGAP9 | No | No | Yes |
| 101 | ARHGAP15 | No | No | Yes |
| 102 | CD38 | No | No | Yes |
| 103 | SP140 | No | No | Yes |
| 104 | BTK | No | No | Yes |
| 105 | IL2RG | No | No | Yes |
| 106 | SPN | No | No | Yes |
| 107 | TAGAP | No | No | Yes |
| 108 | CXCL13 | No | No | Yes |
| 109 | KLRC4 | No | No | Yes |
| 110 | TMEM156 | No | No | Yes |
| 111 | FCRL3 | No | No | Yes |
| 112 | TMC8 | No | No | Yes |
| 113 | FASLG | No | No | Yes |
| 114 | PTPN22 | No | No | Yes |
| 115 | IL7R | No | No | Yes |
| 116 | LSP1 | No | No | Yes |
| 117 | CYBB | No | No | Yes |
| 118 | CCL5 | No | No | Yes |
| 119 | CD84 | No | No | Yes |
| 120 | IRF4 | No | No | Yes |
| 121 | CXCL10 | No | No | Yes |
| 122 | SAMSN1 | No | No | Yes |
| 123 | IFNG | No | No | Yes |
| 124 | LPXN | No | No | Yes |
| 125 | CCR2 | No | No | Yes |
| 126 | CCR4 | No | No | Yes |
| 127 | TNIP3 | No | No | Yes |
| 128 | GBP4 | No | No | Yes |
| 129 | MNDA | No | No | Yes |
| 130 | CD6 | No | No | Yes |
| 131 | CD180 | No | No | Yes |
| 132 | TNFSF13B | No | No | Yes |
| 133 | HLA-F | No | No | Yes |
| 134 | AOAH | No | No | Yes |
| 135 | LAP3 | No | No | Yes |
| 136 | APOL3 | No | No | Yes |
| 137 | KLRK1 | No | No | Yes |
| 138 | KLRK1 | No | No | Yes |
| 139 | AIF1 | No | No | Yes |
| 140 | CD274 | No | No | Yes |
| 141 | ABCD2 | No | No | Yes |
| 142 | PTPN7 | No | No | Yes |
| 143 | B2M | No | No | Yes |
| 144 | STAT4 | No | No | Yes |
| 145 | NKG7 | No | No | Yes |
| 146 | FCER1G | No | No | Yes |
| 147 | TNFRSF9 | No | No | Yes |
| 148 | ITGAE | No | No | Yes |
| 149 | TAP1 | No | No | Yes |
| 150 | GIMAP5 | No | No | Yes |
| 151 | CD226 | No | No | Yes |
| 152 | CLEC7A | No | No | Yes |
| 153 | PSMB9 | No | No | Yes |
| 154 | CXCL11 | No | No | Yes |
| 155 | FAM26F | No | No | Yes |
| 156 | IGLL5 | No | No | Yes |
| 157 | CETP | No | No | Yes |
| 158 | GIMAP1-GIMAP5 | No | No | Yes |
| 159 | IRF1 | No | No | Yes |

TABLE 1-continued

| Row # | Gene Symbol | Specific for CD8+ T Cell Quantity? | Specific for CD8+ T Cell Spatial Distribution? | Common for CD8+ T Cell Quantity and Distribution? |
|---|---|---|---|---|
| 160 | SAMD3 | No | No | Yes |
| 161 | NCF1 | No | No | Yes |
| 162 | RCSD1 | No | No | Yes |
| 163 | CASP1 | No | No | Yes |
| 164 | WDFY4 | No | No | Yes |
| 165 | ZBP1 | No | No | Yes |
| 166 | P2RX5 | No | No | Yes |
| 167 | DOK2 | No | No | Yes |
| 168 | APOBR | No | No | Yes |
| 169 | CD79A | No | No | Yes |
| 170 | SAMD9L | No | No | Yes |
| 171 | PDCD1 | No | No | Yes |
| 172 | SIGLEC10 | No | No | Yes |
| 173 | SIT1 | No | No | Yes |
| 174 | ADAMDEC1 | No | No | Yes |
| 175 | PSTPIP1 | No | No | Yes |
| 176 | KCNA3 | No | No | Yes |
| 177 | KLHL6 | No | No | Yes |
| 178 | CD244 | No | No | Yes |
| 179 | BATF | No | No | Yes |
| 180 | CYTH4 | No | No | Yes |
| 181 | APOL6 | No | No | Yes |
| 182 | CD300LF | No | No | Yes |
| 183 | ZC3H12D | No | No | Yes |
| 184 | AMICA1 | No | No | Yes |
| 185 | FGD2 | No | No | Yes |
| 186 | IL18RAP | No | No | Yes |
| 187 | JCHAIN | No | No | Yes |
| 188 | PTPRCAP | No | No | Yes |
| 189 | IL16 | No | No | Yes |
| 190 | TAP2 | No | No | Yes |
| 191 | ACAP1 | No | No | Yes |
| 192 | PATL2 | No | No | Yes |
| 193 | STAT1 | No | No | Yes |
| 194 | ETV7 | No | No | Yes |
| 195 | CTSS | No | No | Yes |
| 196 | FCMR | No | No | Yes |
| 197 | PARP14 | No | No | Yes |
| 198 | GBP2 | No | No | Yes |
| 199 | PLA2G2D | No | No | Yes |
| 200 | ATP2A3 | No | No | Yes |
| 201 | APOC1 | No | No | Yes |
| 202 | SLC31A2 | No | No | Yes |
| 203 | CD8B | No | No | Yes |
| 204 | IFIH1 | No | No | Yes |
| 205 | SRGN | No | No | Yes |
| 206 | PIK3CD | No | No | Yes |
| 207 | TNFAIP8 | No | No | Yes |
| 208 | SLC7A7 | No | No | Yes |
| 209 | CLNK | No | No | Yes |
| 210 | CLEC4A | No | No | Yes |
| 211 | TRAF1 | No | No | Yes |
| 212 | PSMB8 | No | No | Yes |
| 213 | HLA-DQA1 | No | No | Yes |
| 214 | MZB1 | No | No | Yes |
| 215 | FCRL2 | No | No | Yes |
| 216 | RASGRP3 | No | No | Yes |
| 217 | SLC15A3 | No | No | Yes |
| 218 | GCH1 | No | No | Yes |
| 219 | RASSF4 | No | No | Yes |
| 220 | NFAM1 | No | No | Yes |
| 221 | HMHA1 | No | No | Yes |
| 222 | TBXAS1 | No | No | Yes |
| 223 | HLA-DRB1 | No | No | Yes |
| 224 | SAMHD1 | No | No | Yes |
| 225 | DPYD | No | No | Yes |
| 226 | CLECL1 | No | No | Yes |
| 227 | INPP5D | No | No | Yes |
| 228 | EVI2B | No | No | Yes |
| 229 | NMI | No | No | Yes |
| 230 | CIITA | No | No | Yes |
| 231 | HLA-DMA | No | No | Yes |
| 232 | VAMP5 | No | No | Yes |
| 233 | PTGER4 | No | No | Yes |
| 234 | SFMBT2 | No | No | Yes |
| 235 | BTN3A2 | No | No | Yes |
| 236 | P2RX7 | No | No | Yes |
| 237 | HLA-A | No | No | Yes |
| 238 | EMP3 | No | No | Yes |
| 239 | GIMAP2 | No | No | Yes |
| 240 | BTN3A1 | No | No | Yes |
| 241 | MARCH1 | No | No | Yes |
| 242 | BTN3A3 | No | No | Yes |
| 243 | PIK3AP1 | No | No | Yes |
| 244 | FLI1 | No | No | Yes |
| 245 | CCR5 | Yes | No | No |
| 246 | SIRPG | Yes | No | No |
| 247 | IL21R | Yes | No | No |
| 248 | ZNF683 | Yes | No | No |
| 249 | CD53 | Yes | No | No |
| 250 | GZMH | Yes | No | No |
| 251 | PTPRC | Yes | No | No |
| 252 | LCP2 | Yes | No | No |
| 253 | RHOH | Yes | No | No |
| 254 | SLAMF8 | Yes | No | No |
| 255 | FPR3 | Yes | No | No |
| 256 | HAVCR2 | Yes | No | No |
| 257 | TIGIT | Yes | No | No |
| 258 | GIMAP7 | Yes | No | No |
| 259 | TFEC | Yes | No | No |
| 260 | CD86 | Yes | No | No |
| 261 | FYB | Yes | No | No |
| 262 | NCKAP1L | Yes | No | No |
| 263 | LCK | Yes | No | No |
| 264 | C1orf162 | Yes | No | No |
| 265 | LAX1 | Yes | No | No |
| 266 | GIMAP4 | Yes | No | No |
| 267 | GPR65 | Yes | No | No |
| 268 | SASH3 | Yes | No | No |
| 269 | SLA2 | Yes | No | No |
| 270 | CD4 | Yes | No | No |
| 271 | PLEK | Yes | No | No |
| 272 | CD52 | Yes | No | No |
| 273 | TRGC1 | Yes | No | No |
| 274 | MYO1G | Yes | No | No |
| 275 | ITGA4 | Yes | No | No |
| 276 | EOMES | Yes | No | No |
| 277 | LAIR1 | Yes | No | No |
| 278 | CD80 | Yes | No | No |
| 279 | LAPTM5 | Yes | No | No |
| 280 | SCML4 | Yes | No | No |
| 281 | GZMA | Yes | No | No |
| 282 | CTSW | Yes | No | No |
| 283 | AIM2 | Yes | No | No |
| 284 | GMFG | Yes | No | No |
| 285 | IL12RB1 | Yes | No | No |
| 286 | GZMB | Yes | No | No |
| 287 | CORO1A | Yes | No | No |
| 288 | ARHGAP30 | Yes | No | No |
| 289 | C1QB | Yes | No | No |
| 290 | TYROBP | Yes | No | No |
| 291 | CST7 | Yes | No | No |
| 292 | LST1 | Yes | No | No |
| 293 | LILRB4 | Yes | No | No |
| 294 | MS4A6A | Yes | No | No |
| 295 | SELPLG | Yes | No | No |
| 296 | PIK3R5 | Yes | No | No |
| 297 | MPEG1 | Yes | No | No |
| 298 | CSF2RB | Yes | No | No |
| 299 | LILRB1 | Yes | No | No |
| 300 | SPI1 | Yes | No | No |
| 301 | CRTAM | Yes | No | No |
| 302 | FERMT3 | Yes | No | No |
| 303 | GFI1 | Yes | No | No |
| 304 | TESPA1 | Yes | No | No |
| 305 | WIPF1 | Yes | No | No |
| 306 | LYZ | Yes | No | No |
| 307 | STAP1 | Yes | No | No |
| 308 | SLA | Yes | No | No |
| 309 | GAB3 | Yes | No | No |

TABLE 1-continued

| Row # | Gene Symbol | Specific for CD8+ T Cell Quantity? | Specific for CD8+ T Cell Spatial Distribution? | Common for CD8+ T Cell Quantity and Distribution? |
|---|---|---|---|---|
| 310 | C1QC | Yes | No | No |
| 311 | CXorf21 | Yes | No | No |
| 312 | ALOX5AP | Yes | No | No |
| 313 | C1QA | Yes | No | No |
| 314 | ABI3 | Yes | No | No |
| 315 | ITGAX | Yes | No | No |
| 316 | FCRL5 | Yes | No | No |
| 317 | MS4A1 | Yes | No | No |
| 318 | CCL4 | Yes | No | No |
| 319 | CD7 | Yes | No | No |
| 320 | PLCB2 | Yes | No | No |
| 321 | PDCD1LG2 | Yes | No | No |
| 322 |  | Yes | No | No |
| 323 | ARHGDIB | Yes | No | No |
| 324 | CD40LG | Yes | No | No |
| 325 | BCL11B | Yes | No | No |
| 326 | HCST | Yes | No | No |
| 327 | KCNAB2 | Yes | No | No |
| 328 | NCF4 | Yes | No | No |
| 329 | ANKRD44 | Yes | No | No |
| 330 | FCGR3A | Yes | No | No |
| 331 | ITGAM | Yes | No | No |
| 332 | NLRC5 | Yes | No | No |
| 333 | C3AR1 | Yes | No | No |
| 334 | SELL | Yes | No | No |
| 335 | SLC37A2 | Yes | No | No |
| 336 | TLR6 | Yes | No | No |
| 337 | RNASE6 | Yes | No | No |
| 338 | ITGB2 | Yes | No | No |
| 339 | MSR1 | Yes | No | No |
| 340 | CD74 | Yes | No | No |
| 341 | GIMAP6 | Yes | No | No |
| 342 | NPL | Yes | No | No |
| 343 | SIGLEC14 | Yes | No | No |
| 344 | FAM196B | Yes | No | No |
| 345 | FCRL1 | Yes | No | No |
| 346 | POU2AF1 | Yes | No | No |

In some instances, the machine-learning model (and/or another machine-learning model) may identify one or more genes that are represented in the gene-expression data. For example, a set of parameters (e.g., weights) that are learned and/or fit by the machine-learning model may represent a degree to which expression of various genes are predictive of a quantity and/or location of CD8+ T cells, and at least one of the one or more genes may be determined based on the parameters (e.g., using an absolute or relative threshold). As another example, a pre-configured input data set may be used to interpret the model and to decipher whether and/or an extent to which expression of various genes influence phenotype predictions, and at least one of the one or more genes can be identified based on the interpretation.

A tumor-immune phenotype can correspond to a presence, density and/or location of CD8+ T cells. For example, a tumor-immune phenotype can include 1) an inflamed/infiltrated phenotype in which CD8+ T cells infiltrate the tumor epithelium; 2) an immune excluded phenotype in which infiltrating CD8+ T cells accumulate in the tumor stroma rather than the tumor epithelium, and 3) an immune desert phenotype in which CD8+ T cells are either absent or present in very low numbers. It will thus be appreciated that a tumor-immune phenotype may include one traditionally identified by analyzing one or more digital-pathology images.

Thus, in some instances, one or more genes for which expression levels are used to predict a phenotype may be determined by training a machine-learning model to learn the extent to which expression levels of individual genes are predictive of a phenotype determined (e.g., using a computer algorithm and/or manual annotation) by analyzing digital pathology images. The machine-learning model may be configured to learn the extent to which expression levels of various genes are predictive of traditional phenotypes (e.g., inflamed/infiltrated, immune excluded or immune desert phenotypes).

The machine-learning model may alternatively or additionally be configured to learn the extent to which expression levels of various genes are predictive of one or more novel and/or non-traditional phenotypes. For example, the machine-learning model may classify various gene-expression data sets into distinct clusters, and each of some or all of the clusters may be associated with a phenotype (e.g., corresponding to a potential label output of the machine-learning model). The clustering can include a consensus clustering. The phenotype associated with each phenotype may be determined based on (for example) CD8+ T cell characteristics (e.g., quantity and/or spatial distribution) associated with training data associated with the cluster.

A tumor-immune phenotype can be used to inform treatment decisions and/or generate predictions as to whether and/or a degree to which a particular subject will respond to a particular treatment. For example:

an immune checkpoint inhibitor therapy may be recommended, more likely to be recommended and/or predicted to be more effective for the inflamed/infiltrated phenotype (e.g., relative to the other phenotypes);

anti-TBFβ may be recommended, more likely to be recommended and/or predicted to be more effective for the immune-excluded phenotype (e.g., relative to other phenotypes);

definitive radiochemotherapy may be recommended, more likely to be recommended and/or predicted to be more effective for the immune desert phenotype (e.g., relative to the other phenotypes);

neoadjuvant radiochemotherapy may be recommended, more likely to be recommended and/or predicted to be more effective for the inflamed/infiltrated phenotype (e.g., relative to the other phenotypes); and/or adjuvant radiochemotherapy may be recommended, more likely to be recommended and/or predicted to be more effective for the excluded and inflamed/infiltrated phenotypes (e.g., relative to the desert phenotype).

A computer system may use one or more rules and/or a look-up table to identify a recommended treatment based on a predicted phenotype. An output of the computing system (e.g., that is locally presented and/or transmitted to another device) may include a predicted phenotype, a recommended treatment and/or expression levels of one or more genes (e.g., used to generate the predicted phenotype).

II. Exemplary Interaction System

FIG. 1 shows an interaction system 100 for training and using a machine-learning model to predict a phenotype of a tumor of a subject based on gene-expression data according to some embodiments. Interaction system 100 includes a digital pathology system 105, gene-expression detection system 110, expression-based phenotype classification system 115 and user device 120. It will be appreciated that interaction system 100 may include (for example) multiple digital pathology systems 105, multiple gene-expression detection systems 110 and/or multiple user devices 120. In general, expression-based phenotype classification system 115 may train one or more models using training data received from digital pathology system 105 and gene-expression detection system 110.

Digital pathology system 105 can be configured to generate one or more digital images corresponding to a particular sample. For example, an image can include a stained section of a biopsy sample. As another example, an image can include a slide image (e.g., a blood film) of a liquid sample.

Some types of samples (e.g., biopsies, solid samples and/or samples including tissue) can be processed by a fixation/embedding system to fix and/or embed the sample. The sample can be infiltrated with a fixating agent (e.g., liquid fixing agent, such as a formaldehyde solution) and/or embedding substance (e.g., a histological wax). For example, a fixation sub-system can fixate a sample by exposing the sample to a fixating agent for at least a threshold amount of time (e.g., at least 3 hours, at least 6 hours, or at least 12 hours). A dehydration sub-system can dehydrate the sample (e.g., by exposing the fixed sample and/or a portion of the fixed sample to one or more ethanol solutions) and potentially clear the dehydrated sample using a clearing intermediate agent (e.g., that includes ethanol and a histological wax). An embedding sub-system can infiltrate the sample (e.g., one or more times for corresponding predefined time periods) with a heated (e.g., and thus liquid) histological wax. The histological wax can include a paraffin wax and potentially one or more resins (e.g., styrene or polyethylene). The sample and wax can then be cooled, and the wax-infiltrated sample can then be blocked out.

A sample slicer can receive the fixed and embedded sample and can produce a set of sections. The sample slicer can expose the fixed and embedded sample to cool or cold temperatures. The sample slicer can then cut the chilled sample (or a trimmed version thereof) to produce a set of sections. Each section may have a thickness that is (for example) less than 100 µm, less than 50 µm, less than 10 µm or less than 5 µm. Each section may have a thickness that is (for example) greater than 0.1 µm, greater than 1 µm, greater than 2 µm or greater than 4 µm. The cutting of the chilled sample may be performed in a warm water bath (e.g., at a temperature of at least 30° C., at least 35° C. or at least 40° C.).

An automated staining system can facilitate staining one or more of the sample sections by exposing each section to one or more staining agents. Each section may be exposed to a predefined volume of staining agent for a predefined period of time. In some instances, a single section is concurrently or sequentially exposed to multiple staining agents. The multiple staining agents may include (for example) haematoxylin and a primary antibody (e.g., CD8 immunohistochemistry).

Each of one or more stained sections can be presented to an image scanner, which can capture a digital image of the section. The image scanner can include a microscope camera. The image scanner may be further configured to capture annotations and/or morphometrics identified by a human operator.

In some instances, a section is returned to the automated staining system after one or more images are captured, such that the section can be washed, exposed to one or more other stains and imaged again. When multiple stains are used, the stains may be selected to have different color profiles, such that a first region of an image corresponding to a first section portion that absorbed a large amount of a first stain can be distinguished from a second region of the image (or a different image) corresponding to a second section portion that absorbed a large amount of a second stain.

It will be appreciated that one or more components of digital pathology system 105 may, in some instances, operate in connection with human operators. For example, human operators may move the sample across various sub-systems (e.g., of a fixation embedding system or of an image-generation system) and/or initiate or terminate operation of one or more sub-systems, systems or components of digital pathology system 105.

Further, it will be appreciated that, while various described and depicted functions and components of digital pathology system 105 pertain to processing of a solid and/or biopsy sample, other embodiments can relate to a liquid sample (e.g., a blood sample). For example, digital pathology system 105 may be configured to receive a liquid-sample (e.g., blood or urine) slide, that includes a base slide, smeared liquid sample and cover. The image scanner can then capture an image of the sample slide.

The digital pathology images may be processed at digital pathology system and/or at a remote system. In some instances, image processing can include aligning multiple images corresponding to a same sample. For example, multiple images may correspond to a same section of a same sample. Each image may depict the section stained with a different stain. As another example, each of multiple images may correspond to different sections of a same sample (e.g., each corresponding to a same stain or for which different subsets of the images correspond to different stains). For example, alternating sections of a sample may have been stained with different stains. Section alignment can include determining whether and/or how each image is to be translated, rotated, magnified and/or warped such that images corresponding to a single sample and/or to a single section are aligned. An alignment may be determined using (for example) a correlation assessment (e.g., to identify an alignment that maximizes a correlation).

Image processing can further include automatically detecting depictions of objects (e.g., biological objects) of one or more particular types in each of the aligned images. Object types may include types of cells or types of biological structures. For example, a first set of objects may correspond to a particular (e.g., labeled) cell type, such as T cells or $CD8^+$ T cells, and a second set of objects may correspond to a tumor region. In some instances, at least one type of object is identified via manual annotations. For example, input from a human annotator may identify a border of a tumor region, and automated cell detection may identify locations (e.g., borders or point locations) of $CD8^+$ T cells. In some instances, all objects are detected via automated detection (e.g., where tumor epithelium are distinguished from stroma epithelium using an algorithm that distinguishes shape and size of tumor nuclei from stroma nuclei). Cells may be detected using the counterstain signals, and a primary protein of interest may be evaluated using the haematoxylin signal. A DAB intensity statistic (e.g., mean DAB intensity) may be calculated for each nucleus.

In some instances, objects of different types are detected within a same image. In some instances, objects of a first type are detected within a first image, and one or more objects of a second type are detected within a second image (associated with a same or different sample slide).

Object detection may use static rules and/or a trained model to detect and characterize objects. Rules-based object detection can include (for example) detecting one or more edges, identifying a subset of edges that are sufficiently connected and closed in shape and/or detecting one or more high-intensity regions or pixels. A portion of an image may be determined to depict an object if (for example) an area of a region within a closed edge is within a predefined range and/or if a high-intensity region has a size within a predefined range. Detecting object depictions using a trained model may include employing a neural network, such as a convolutional neural network, a deep convolutional neural network and/or a graph-based convolutional neural network. The model may have been trained using annotated images that included annotations indicating locations and/or boundaries of objects. The annotated images may have been received from a data repository (e.g., a public data store) and/or from one or more devices associated with one or more human annotators.

Rules-based object detection and trained model object detection may be used in any combination. For example, rules-based object detection may detect depictions of one type of object while a trained model is used to detect depictions of another set of object. Another example may include validating results from rules-based object detection using objects output by a trained model, or validating results of the trained model using a rules-based approach. Yet another example may include using rules-based object detection as an initial object detection, then using a trained model for more refined object analysis, or applying a rules-based object detection approach to an image after depictions of an initial set of objects are detected via a trained network.

Object detection can also include (for example) pre-processing an image to (for example) transform a resolution of the image to a target resolution, apply one or more color filters, and/or normalize the image. For example, a color filter can be applied that passes colors corresponding to a color profile of a stain used to stain a sample. Rules-based object detection or trained model object detection may be applied to a pre-processed image.

For each detected object, a single representative location of the depicted object (e.g., centroid point or midpoint), a set of pixels or voxels corresponding to an edge of the depicted object and/or a set of pixels or voxels corresponding to an area of the depicted object may be identified and stored as object data. This object data can be stored with an identifier of the object (e.g., a numeric identifier), an identifier of a corresponding image, an identifier of a corresponding subject and/or an identifier of the type of object.

Gene-expression detection system 110 can be configured to detect the expression level of each of a set of genes. Gene expression levels may represent the extent to which DNA is converted to a functional product, such as a protein. Gene-expression detection system 110 can determine gene-expression levels by measuring mRNA that corresponds to a precursor for a protein or by measuring proteins directly. Exemplary techniques that may be used by gene-expression detection system 110 include Northern blotting, Western blotting, RT-qPCR, flow cytometry, and RNA-Seq.

Northern blotting involves separating a sample of RNA on an agarose gel. The RNA sample can be radioactively labeled to generate RNA that is complementary to a target sequence. The radioactively labeled RNA can then be detected by an autoradiograph to determine size and sequence information about the mRNA. Labelling may also be performed using digoxigenin and biotin substances.

Western blotting involves a similar process as Northern blotting, but Western blotting measures protein levels instead of mRNA levels. During Western blotting, electrophoresis is performed on the protein sample to separate individual proteins into distinct bands. The proteins can then be transferred to a treated piece of paper. The paper is incubated with an antibody for the target protein so that the antibody binds to the target protein.

In RT-qPCR, a complementary DNA (cDNA) template is generated for an mRNA sample during reverse transcription. Then, during quantitative PCR, the cDNA is amplified. A labeled hybridization probe or dye with a known fluorescence may be used during the amplification. A measurement of the number of copies of original mRNA can be determined using a standard curve. RT-qPCR provides the ability to detect a single mRNA molecule, but the process can be expensive depending on the probe or dye used.

Flow cytometry involves analyzing gene expression at a single-cell level. A biological sample containing DNA is injected into a flow cytometer and cells flow one at a time through a channel. A beam of light illuminates the cells and detectors record an intensity and duration of a signal of scattered light by each cell. Fluorophore labels, dyes, and stains with a known emission signal can be attached to an antibody of a target protein to quantify protein levels in each cell of the sample. In addition to providing quantification at the single-cell level, flow cytometry allows multiple proteins to be targeted at a time, reducing time involved in analysis.

During RNA-Seq, cDNA fragments are generated from RNA molecules. The cDNA molecules are then sequenced using high-throughput techniques. The reads can be aligned to a reference genome or reference transcripts to determine gene expression levels. RNA-Seq allows the entire transcriptome (e.g., mRNA, rRNA, tRNA) to be analyzed. RNA-Seq is not limited to genes that encode proteins, and thus, detects genes that do not encode proteins. However, RNA-Seq is relatively easy to perform and provides accurate quantification of gene expression levels.

Gene-expression detection system 110 may perform normalization (e.g., to counts per million), filtering (e.g., to remove lowly expressed genes), and/or transformations. Outliers may be removed, such as by using a component analysis technique (e.g., principal component analysis).

Each samples processed by digital pathology system 105 may have been collected from a subject. One or more different users (e.g., one or more physicians, laboratory technicians and/or medical providers) may have initiated the collection of the sample, initiated the processing of the sample and/or may receive results of processing of the sample. An associated user can include a person who ordered a test or biopsy that produced a sample being imaged and/or a person with permission to receive results of a test or biopsy. For example, a user can correspond to a physician or a subject (from whom a sample was taken) him/herself. A user can use one or one user devices 120 to (for example) initially submit one or more requests (e.g., that identify a subject) that a sample be processed by digital pathology system 105.

In some instances, each of digital pathology system 105 and/or gene-expression detection system 110 transmits results directly to expression-based phenotype classification system 115. In some instances, each of digital pathology system 105 and/or gene-expression detection system transmits results to user device 120, which can initiate automated processing of the results by expression-based phenotype classification system 115.

Expression-based phenotype classification system 115 can include a label generator 120 that can assign one or more labels to each subject's data in a training set based on objects detected within the subject's digital pathology images. The labels may include a first "quantity" label characterizing a quantity of depictions of a particular object type (e.g., $CD8^+$ T cells) and a second "spatial-distribution" label characterizing a spatial distribution of depictions of a particular object type ($CD8^+$ T cells). The quantity label may include and/or may be based on a count (e.g., raw or normalized count, such as a density) of depictions of the object type within one or more regions. For example, the quantity label may be defined to be the sum of depictions of $CD8^+$ T cells in stroma versus tumor regions or the square root of the sum of the square of the count of $CD8^+$ T cells in the stroma regions and the square of the count of $CD8^+$ T cells in the tumor regions.

The spatial-distribution label may be based on a difference, ratio and/or angle between a count (e.g., raw or normalized count, such as a density) of depictions of the object type within a first region and a count of depictions of the object type within a second region. For example, the spatial-distribution label may be defined to be the arctangent of the ratio of a count of $CD8^+$ T cells in the stroma regions relative to a count of the $CD8^+$ T cells in the tumor regions. Thus, if all of the $CD8^+$ T cells are in the tumor regions, the spatial-distribution label would be 0.

Expression-based phenotype classification system 115 further includes a gene-significance detector 125 that uses the gene-expression data and the labels to determine, for each gene (of a set of genes for which expression levels were measured), whether the gene is specific to a quantity prediction (predicting a quantity of $CD8^+$ T cells), spatial-distribution prediction (predicting a distribution of $CD8^+$ T cells across tumor versus stroma cells), both or neither. Gene-significance detector 125 may, for each of the set of genes, fit or train a model using the labels and gene-expression data from the training data. The model may include (for example) a regression model and/or random-forest regression model. Gene-significance detector 125 may characterize a gene as being specific to a quantity prediction (or spatial-distribution prediction) when an increase in a mean-square error of the quantity prediction (or spatial-distribution prediction) was above a predefined threshold (e.g., a bottom threshold of a fourth quartile). In some instances, a given gene is specific both to a quantity prediction and to a spatial-distribution prediction. In some instances, a given gene is not specific both to a quantity prediction or to a spatial-distribution prediction.

A phenotype clustering controller 130 can use expression levels from the training data for the genes determined to be specific to quantity predictions and for genes specific to spatial-distribution predictions to perform a clustering analysis (e.g., consensus clustering). In some instances, training data pertaining to genes determined to be specific both to quantity and spatial-distribution predictions were further used for the clustering analysis. For example, the immune desert phenotype may be associated with smaller quantity predictions (predicting fewer $CD8^+$ T cells), an immune infiltrated phenotype may be associated with a spatial-distribution prediction predicting presence of $CD8^+$ T cells in tumor regions, and an immune excluded phenotype may be associated with a spatial-distribution prediction predicting relatively few $CD8^+$ T cells in tumor regions and more $CD8^+$ T cells in stroma regions.

The clustering analysis may implement a constraint on a number of clusters. Phenotype clustering controller 130 can assign each of the clusters to an immune phenotype based on the labels associated with the clusters. Immune phenotypes to which a cluster may be assigned may include immune desert, immune excluded or immune infiltrated.

Thus, multiple machine-learning models may be used to identify the genes that are specific to T-cell quantity and distribution and to characterize how expression of those genes are associated with immune phenotypes.

While digital-pathology images can be used to identify particular genes that are informative and/or predictive as to immune phenotype and can also be used to identify genetic profiles associated with immune phenotypes, the particular genes and genetic profiles may then be used to support predicting immune-phenotype prediction without relying on digital pathology images. Thus, phenotype clustering controller 130 may be configured to receive a new data set of gene-expression levels corresponding to a particular subject from gene-expression detection system 110 (which may be a same or different system as one contributing to training data) and may assign the data set to a particular cluster and to thus predict a phenotype associated with the cluster for the particular subject.

Each component and/or system depicted in FIG. 1 can include (for example) one or more computers, one or more servers, one or more processors and/or one or more computer-readable media. In instances in which a component and/or system depicted in FIG. 1 includes multiple servers, multiple processors and/or multiple computer-readable media, the multiple servers, processors and/or media may be co-located and/or distributed. In some instances, a component and/or system depicted in FIG. 1 may include and/or may be part of a cloud computing system.

III. Exemplary Training and Use of Phenotype-Classification Procedures

III.A. Exemplary Training of Tumor Phenotype-Classification Procedure

Figure 2:
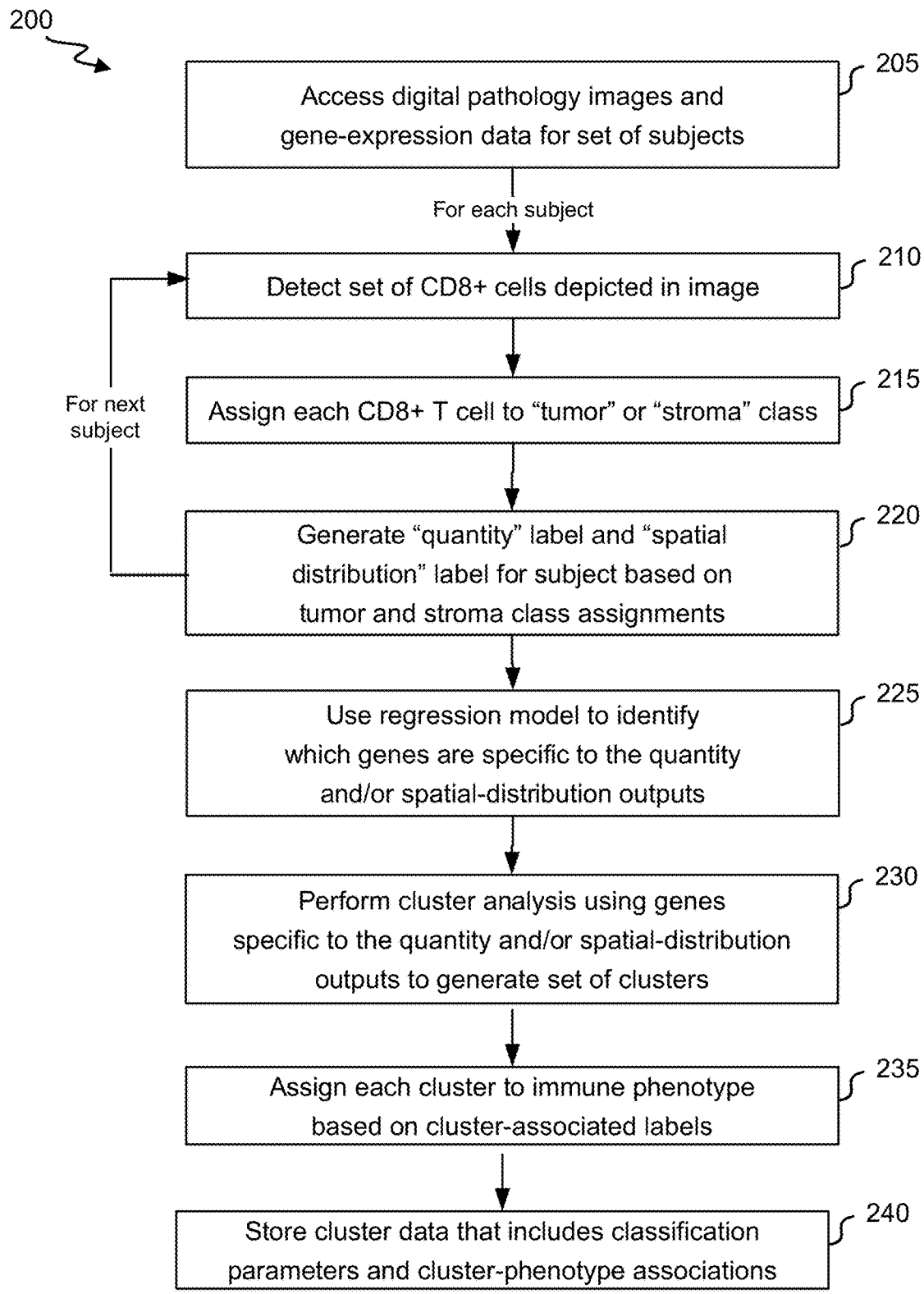
FIG. 2 shows an exemplary process for training a tumor phenotype-classification workflow according to some embodiments.

FIG. 2 shows an exemplary process 200 for training a tumor phenotype-classification workflow according to some embodiments. Process 200 begins at block 205 where a training data set corresponding to a set of subjects is received. The training data set may include, for each of a set of subjects, one or more digital pathology images and a set of expression levels of each of a set of genes. The training data set may have been received (e.g., from or based on data initially received from) one or more digital pathology systems 105 and one or more gene-expression detection systems 110. The digital pathology images may include depictions of stained and counterstained biological objects. For example, the digital pathology images may include signals representative of nuclei and $CD8^+$ T cells. The set of expression levels may have been determined based on (for example) Northern blotting, Western blotting, RT-qPCR, flow cytometry, and RNA-Seq processing.

Blocks 210-220 may be performed (e.g., at expression-based phenotype classification system 115) for each subject in the set of subjects. At block 210, a set of $CD8^+$ T cell depictions in the digital pathology image(s) corresponding to the subject can be identified. For example, each digital pathology image may have been subjected to $CD8^+$ IHC staining and hematoxylin counterstaining. Each image may be filtered using a frequency corresponding to the $CD8^+$ IHC staining and further processed to identify substantial signals (e.g., via thresholding, peak detection, local averaging and thresholding, etc.). In some instances, an image is first filtered based on a counterstain frequency and processed for cell segmentation to identify cell boundaries. Within each boundary, signals at the $CD8^+$ IHC staining frequency may then be (for example) averaged, summed or processed to identify a median value, and the result may be compared to a threshold to predict whether the cell is a $CD8^+$ T cell.

At block 215, each detected $CD8^+$ T cell is assigned to a category to indicate whether it is within a tumor region or a stroma region. In some instances, a human annotator may have identified each of one or more tumor and/or stroma regions within the image (or another version thereof), and a mapping may be used for the categorization. In some instances, an automated processing is used to predict which portions of the image correspond to tumor (versus stroma regions). For example, hematoxylin signals may be predictive of whether a given cell is within a tumor region, as nuclei in tumors may have greater asymmetry and size outliers. A neighbor, cluster, convolution-network or other approach may then be used to process nuclei assignments to predict tumor/stroma regions.

At block 220, a quantity label and spatial distribution label can be generated for the subject based on the $CD8^+$ T cell detections and classifications. The quantity label may be based on (for example) a total number of detected $CD8^+$ T cells, a (normalized or unnormalized) number of $CD8^+$ T cells detected in each stroma region, a (normalized or unnormalized) number of $CD8^+$ T cells detected in each tumor region, a square of a number of $CD8^+$ T cells detected in each stroma region, and/or a square of a number of $CD8^+$ T cells detected in each tumor region. For example, the quantity label can be defined to be a square root of a sum of a square of a number of $CD8^+$ T cells detected in each stroma region and a square of a number of $CD8^+$ T cells detected in each tumor region. The spatial-distribution label may be based on (for example) a difference between, a ratio or and/or an angle between a (normalized or unnormalized) number of $CD8^+$ T cells detected in each stroma region and a (normalized or unnormalized) number of $CD8^+$ T cells detected in each tumor region. In some instances, the quantity label and the spatial-distribution label can be configured to be represented as polar coordinates.

At block 225, a regression model may be used (e.g., by expression-based phenotype classification system 115) to identify which genes of the set of genes represented in the expression data are specific to $CD8^+$ T cell quantity and/or $CD8^+$ T cell spatial distribution. For each of the set of genes, a first model may be trained and/or a first function may be fit to determine an extent expression of the gene is predictive of and/or informative of (e.g., in terms of entropy reduction) values of the quantity label. Similarly, a second model may be trained and/or a second function may be fit to determine an extent expression of the gene is predictive of and/or informative of (e.g., in terms of entropy reduction) values of the spatial-distribution label. The first and second models and/or functions may be of a same or different type. The first and/or second models and/or functions may include a regression function and/or a random forest regression model. Training a model and/or fitting a function may result in determining one or more parameters and/or weights, which may then be compared to a threshold to assess specificity. The threshold may include an absolute threshold or relative threshold (e.g., defined based on the parameters and/or weights identified across the set of genes). A subset of the set of genes determined to be sufficiently specific may be determined based on the threshold analysis. In some instances, the subset includes genes within the set of genes determined to be sufficiently specific for the quantity variable or for the spatial-distribution variable. In some instances, the subset includes genes within the set of genes determined to be sufficiently specific for the quantity variable and/or for the spatial-distribution variable.

At block 230, a cluster analysis is performed using expression values for genes determined to be sufficiently specific. The cluster analysis may include using a component analysis, such as principal component analysis or independent component analysis. The cluster analysis may limit a number of clusters (e.g., to 3, 4, 5, 6, 7, 8, etc.). The cluster analysis may be unsupervised and/or performed only based on quantity and spatial-distribution values.

At block 235, each of the clusters may be assigned to an immune phenotype based on quantity and/or spatial-distribution labels associated with data points (associated with subjects) assigned to the cluster. The immune-phenotype assignment may be based on whether cluster-associated quantity labels were low or high and/or whether cluster-associated spatial-distribution labels were indicative of CD8+ T cell enrichment in the stroma versus in tumors. Potential immune-phenotype assignments include immune desert, immune excluded or immune infiltrated. For example, the immune desert phenotype may be associated with low $CD8^+$ T cell quantity labels; the immune excluded phenotype may be associated with high $CD8^+$ T cell quantity labels and spatial distribution labels indicating stroma concentration; and the immune infiltrated phenotype may be associated with high CD8+ T cell quantity labels and spatial distribution labels indicating tumor concentration.

At block 240, cluster data is stored. The cluster data may indicate how the clusters are differentiated from each other (e.g., via one or more hyperplanes, weight assessments, principal components, ranges of quantity and/or spatial-distribution values, etc.). The cluster data may further identify, for each cluster, to which immune phenotype the cluster corresponds.

III.B. Exemplary Use of Tumor Phenotype-Classification Procedure

Figure 3:
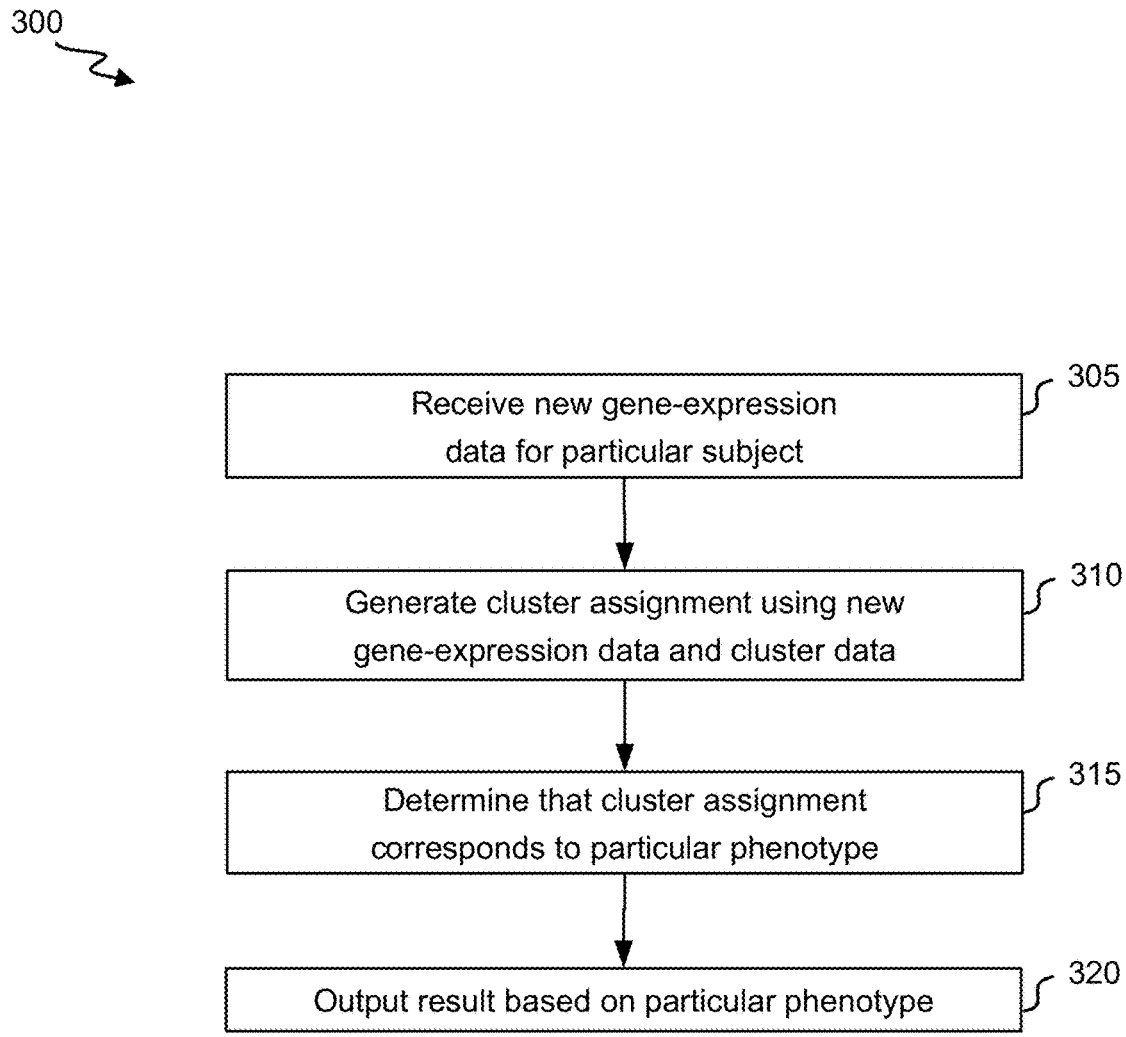
FIG. 3 shows an exemplary process for using a trained tumor phenotype-classification workflow to predict an immune phenotype based on genetic expression data according to some embodiments.

FIG. 3 shows an exemplary process 300 for using a trained tumor phenotype-classification workflow to predict an immune phenotype based on genetic expression data according to some embodiments. Process 300 may be performed in part or in its entirety by expression-based phenotype classification system 115. Process 300 begins at block 305, where new gene-expression data is received that corresponds to a particular subject. The new gene-expression data may be received from a gene-expression detection system 110. The new gene-expression data identify expression levels for each of some or all of the genes for which it was determined the gene was specific to the quantity and/or spatial distribution outputs at block 225 of process 200. In some instances, digital pathology data for the particular subject was not received.

At block 310, a cluster assignment is generated using the new gene-expression data and cluster data (e.g., that was stored at block 240 in process 200). For example, each of the expression levels in the new gene-expression data may be weighted and/or transformed (e.g., using one or more components) to generate a set of coordinates in a representative space. A distance between the coordinates and each of a set of reference coordinates (corresponding to multiple clusters) may be calculated to identify a cluster associated with a minimum distance. In some instances, a cluster assignment is generated using a nearest-neighbor or K-means approach.

At block 315, it is determined that the cluster assignment corresponds to a particular immune phenotype. The determination may be made using a look-up from data in the cluster data (e.g., that was stored at block 240 in process 200).

At block 320, a result is output based on the particular immune phenotype. The result may identify the particular immune phenotype, a treatment predicted to be effective for the particular immune phenotype, a predicted efficacy of a particular treatment given the predicted particular immune phenotype, etc. The result may further be accompanied by (for example) some or all of the new gene-expression data (or a processed version thereof).

In some instances, a prediction of a molecular subtype of a tumor is generated based on a predicted immune phenotype. For example, it may be predicted that a particular subject has an immunoreactive molecular subtype of ovarian cancer when it is predicted that genetic expression data for the subject corresponds to an infiltrated immune phenotype. As another example, it may be predicted that a particular subject has a mesenchymal molecular subtype of ovarian cancer when it is predicted that genetic expression data for the subject corresponds to an excluded immune phenotype. As yet another example, it may be predicted that a particular subject has either a differentiated molecular subtype or a proliferative molecular subtype when it is predicted that genetic expression data for the subject corresponds to an immune desert phenotype.

In some instances, immune phenotype predictions may be used to investigate and identify pathways and immune features of a particular immune phenotype (e.g., an excluded phenotype). More specifically, an immune phenotype may be predicted based on expression levels of multiple genes (e.g., in accordance with process 300), and in situ analysis may be performed to detect whether and/or an extent to which a particular phenotype is associated with one or more particular types of upregulation or downregulation. For example, as further detailed in Section IV.D. below, phenotype predictions and transcriptional analysis can be used to predict that the immune excluded phenotype is associated with upregulation of TGFβ and stromal activation and the loss of antigen presentation on tumor cells. As another example, phenotype predictions and transcriptional analysis can be used to predict that the immune excluded phenotype and a subset of the immune desert phenotype are associated with a downregulation of HLA-A.

It will be appreciated that treatments may be informed, selected and/or provided based on the immune phenotype predictions and/or based on predicted pathways and/or immune features of particular immune phenotypes. For example, it may be inferred or determined that a tumor of a subject has an immunosuppressive microenvironment (e.g., by processing a sample to assess immunoactivity or based on gene-expression data). A treatment of an inhibitor of TGFβ may then be provided to the subject. As another example, it may be inferred or determined that a subject has a medical condition associated with reduced expression of HLA-A relative to healthy subjects. The medical condition may include an immune excluded phenotype of cancer. A treatment including an inhibitor of TGFβ can then be provided to the subject. As another example, it may be inferred or determined that a subject has a medical condition associated with reduced expression of HLA-A relative to healthy subjects. The medical condition may include an immune excluded phenotype of cancer. A treatment including an IFNγ treatment and a EZH2 or DNMT inhibitor.

IV. Example

IV.A. Technique for Processing Immunohistochemistry Images to Generate CD8 T Cell Quantity and/or Distribution Metrics Digital pathology images were accessed, which depict stained samples. More specifically, CD8 immunohistochemistry with a haematoxylin counter-staining was performed on each of a set tissue samples collected from a set of subjects in the ICON7 trial having ovarian cancer (n=155). Cell-type detection was performed. Each detected cell was assigned to a category (e.g., a tumor epithelium cell or stromal cell). The assignment was based on a size and shape of a nucleus. $CD8^+$ T cell densities in the tumor epithelium and/or $CD8^+$ T cell densities in the stroma compartment were calculated based on the categorizations.

Metrics were defined to include a total $CD8^+$ T cell count, a $CD8^+$ T cell count per tumor epithelium and/or a $CD8^+$ T cell count stroma area (See FIG. 4a). To better capture and quantify the CD8 infiltration patterns, the CD8 scores were converted into polar coordinates defining two new quantitative metrics: 1) the quantity of $CD8^+$ T cells (R=squareroot $[(CD8\ tumor)^2+(CD8\ stroma)^2]$) and 2) the spatial distribution of $CD8^+$ T cells (θ=atan(CD8 stroma/CD8 tumor)).

These two digitally defined quantitative metrics were used to profile the immune phenotype of each tumor using a two-dimensional map (FIG. 4b). Representative tumors of the infiltrated, excluded and desert immune phenotypes, manually defined by a pathologist, were highlighted to validate the two digital metrics, with desert tumors having low $CD8^+$ T cell quantity (R), and excluded versus infiltrated tumors differing in the spatial distribution of $CD8^+$ T cells (θ). The distinct patterns of $CD8^+$ T cell distribution in digitally denoted stroma vs. tumor epithelial areas of these tumors are illustrated in FIG. 4c, which shows example images of representative infiltrated, excluded and desert tumor-immune phenotypes to illustrate their distinct $CD8^+$ T cell distribution in digitally denoted stroma vs. tumor areas. For example, the images show relative positions of tumor areas 405, stroma areas 410, $CD8^+$ cells present in the tumor 415, and $CD8^+$ cells present in the stroma 420. Tumor nuclei 425 (nuclei of cells in the tumor areas) can have different spatial characteristics relative to stroma nuclei 430 (nuclei of cells in the stroma areas). The results demonstrate that both total $CD8^+$ T cell quantities and their spatial distribution in the tumor microenvironment are more on a continuum rather than discrete entities in the vast majority of tumors (FIG. 4b). These results highlight advantages of using the digitally devised two-dimensional quantitative metrics to define the immune phenotype of individual ovarian tumors.

IV.B. Machine-Learning Processing of CD8 T Cell Quantity and/or Distribution Metrics to Identify Tumor-Immune Phenotype A gene expression-based molecular classifier was generated using a machine learning approach to characterize tumor-immune phenotypes. FIG. 5a summarizes the development workflow. In this approach, transcriptome RNAseq analysis can be integrated with the digital pathology analysis. More specifically, a machine-learning model (e.g., a random forest regression model) can be trained with a training data set that includes quantitative metrics corresponding to pathology images (e.g., CD8 T-cell quantity and distribution metrics), RNAseq data and labels that indicate whether each data element corresponds to an infiltrated, excluded or desert immune phenotype.

As indicated in blocks 1 and 2 of FIG. 5a, digital pathology data (corresponding to different immune phenotypes) and transcriptome analyses can be accessed. Blocks 1 and 2 of FIG. 5 may correspond to block 205 of process 200 depicted in FIG. 2. In some instances, the digital pathology data is labeled to indicate $CD8^+$ T cell quantity and/or spatial-distribution metrics (e.g., based on actions corresponding to blocks 210-220 of process 200 depicted in FIG. 2). In some instances, the digital pathology data is processed (e.g., via actions corresponding to blocks 210-220 of process 200 depicted in FIG. 2) to generate $CD8^+$ T cell quantity and spatial-distribution metrics. In block 3 of FIG. 5a, one or more machine-learning models (e.g., a random forest model) can be used to identify genes that are specific to the quantity and/or spatial-distribution metrics. Block 3 of FIG. 5a may correspond to block 225 of process 200 depicted in FIG. 2. In block 4 of FIG. 5*a*, consensus clustering can be performed to define a set of clusters for each of a set of immune phenotypes. Block 4 of FIG. 5*a* may correspond to block 230 of process 200 depicted in FIG. 2. At block 5 of FIG. 5*a*, a 157-gene molecular classifier can be built based on cluster data associated with the set of clusters.

In an exemplary case, a training data set was defined to include data from 155 samples from the ICON7 trial. By assessing the learned data, 352 genes were identified for which expression of the gene was significantly related to the quantity (R) and/or spatial distribution of $CD8^+$ T cells (θ) (See FIG. 6*a-b*, Table 2). Among these genes, 103 genes were associated with total $CD8^+$ T cell quantity, 56 genes varied in expression by spatial $CD8^+$ T cell distribution, and 193 genes were associated with both total quantity and spatial distribution (FIGS. 5*b* and 6*c*). Thus, it will be appreciated that the relationships between the $CD8^+$ T-cell (quantity and spatial-distribution) metrics and immune phenotypes as depicted in FIGS. 6A and 6B may be used in block 235 of process 200 (depicted in FIG. 2) to assign each cluster of gene-expression data points to an immune phenotype class.

TABLE 2

| entrez | Percent Inc MSE R | Percent Inc MSE theta | IncNode Purity R | Inc Node Purity theta | imp SD R | imp SD theta | mean mse |
|---:|---:|---:|---:|---:|---:|---:|---:|
| 10663 | 52.77584 | 18.38540 | 114.33024 | 64.11113 | 0.01002 | 0.00731 | 0.64911 |
| 285175 | 52.06611 | 12.08795 | 108.80847 | 64.07137 | 0.00909 | 0.00631 | 0.71764 |
| 2395 | 11.74546 | 13.48128 | 66.06567 | 64.57157 | 0.00683 | 0.00746 | 0.71934 |
| 54470 | 9.02468 | 10.73301 | 56.16052 | 70.62778 | 0.00721 | 0.00733 | 0.72575 |
| 2191 | 49.12452 | 19.32572 | 115.53590 | 74.94296 | 0.00997 | 0.00673 | 0.73447 |
| 80709 | 59.65823 | 25.22041 | 124.27186 | 73.95832 | 0.01001 | 0.00729 | 0.75605 |
| 9830 | 51.84139 | 14.35802 | 108.18857 | 66.56565 | 0.00945 | 0.00709 | 0.76034 |
| 64761 | 54.11211 | 13.41919 | 115.54400 | 70.63301 | 0.00998 | 0.00736 | 0.76202 |
| 54809 | 58.56798 | 11.97310 | 126.56990 | 62.01809 | 0.01112 | 0.00700 | 0.76271 |
| 3822 | 48.93460 | 12.32536 | 116.52976 | 76.21844 | 0.00954 | 0.00793 | 0.76917 |
| 57643 | 30.45691 | 11.26409 | 95.69994 | 68.47897 | 0.00817 | 0.00766 | 0.78159 |
| 943 | 33.33167 | 11.45578 | 98.35017 | 68.01929 | 0.00925 | 0.00758 | 0.78433 |
| 347731 | 48.26768 | 12.16732 | 113.52434 | 74.16325 | 0.01055 | 0.00768 | 0.78462 |
| 53829 | 47.91098 | 10.24170 | 117.66306 | 72.55352 | 0.00970 | 0.00779 | 0.78562 |
| 474354 | 50.47335 | 15.66253 | 124.33489 | 80.62467 | 0.01135 | 0.00890 | 0.78981 |
| 3601 | 53.32777 | 18.69516 | 126.28528 | 75.18373 | 0.01064 | 0.00796 | 0.79233 |
| 55589 | 58.24552 | 10.34827 | 137.88544 | 59.74336 | 0.01085 | 0.00717 | 0.79303 |
| 3718 | 49.39215 | 18.15247 | 121.49378 | 74.97037 | 0.01110 | 0.00771 | 0.79456 |
| 57333 | 7.12602 | 20.27556 | 71.85936 | 78.82313 | 0.00707 | 0.00823 | 0.79703 |
| 64127 | 59.39032 | 12.15968 | 134.87688 | 65.91532 | 0.01055 | 0.00730 | 0.80142 |
| 54578 | 37.26812 | 16.19775 | 104.76405 | 70.60200 | 0.01069 | 0.00863 | 0.80512 |
| 8737 | 34.67532 | 20.05405 | 98.36039 | 77.49393 | 0.00931 | 0.00796 | 0.80527 |
| 6999 | 48.07688 | 10.38006 | 119.98205 | 72.03570 | 0.00910 | 0.00729 | 0.80553 |
| 51816 | 48.03886 | 10.66160 | 125.63012 | 71.63275 | 0.01003 | 0.00770 | 0.80560 |
| 460 | 46.12450 | 16.21435 | 108.32151 | 77.12986 | 0.01038 | 0.00804 | 0.80615 |
| 152789 | 33.23724 | 11.68959 | 110.32180 | 74.57565 | 0.01086 | 0.00822 | 0.80866 |
| 116986 | 46.24840 | 15.58608 | 126.15265 | 72.27593 | 0.01194 | 0.00802 | 0.81093 |
| 3112 | 53.14611 | 12.19775 | 127.42489 | 70.26102 | 0.01142 | 0.00809 | 0.81562 |
| 8643 | 35.39198 | 10.22808 | 102.83205 | 72.13323 | 0.00968 | 0.00805 | 0.81646 |
| 5699 | 45.33917 | 17.50402 | 120.95994 | 82.70124 | 0.00964 | 0.00801 | 0.81917 |
| 55840 | 46.80652 | 11.79301 | 124.96452 | 78.38424 | 0.01203 | 0.00855 | 0.81983 |
| 10154 | 46.25412 | 15.61540 | 114.61539 | 76.66837 | 0.01074 | 0.00800 | 0.82087 |
| 196740 | 43.35386 | 13.63341 | 106.44191 | 78.63587 | 0.00995 | 0.00779 | 0.82391 |
| 219654 | 24.52037 | 26.55238 | 77.94490 | 89.29776 | 0.00887 | 0.00865 | 0.82494 |
| 6892 | 53.92957 | 24.54225 | 120.50222 | 85.49727 | 0.01064 | 0.00877 | 0.82624 |
| 347736 | 22.27066 | 12.62419 | 89.70483 | 74.81484 | 0.00842 | 0.00758 | 0.82759 |
| 197358 | 43.82128 | 20.33007 | 116.46185 | 81.36987 | 0.00994 | 0.00793 | 0.82816 |
| 1945 | 25.01949 | 28.23179 | 103.62053 | 93.89257 | 0.00961 | 0.00997 | 0.82929 |
| 146562 | 20.75102 | 11.81963 | 85.32423 | 77.10055 | 0.00857 | 0.00787 | 0.82933 |
| 4599 | 47.72123 | 13.37017 | 104.88072 | 76.65746 | 0.00984 | 0.00733 | 0.83007 |
| 54579 | 36.41598 | 13.32028 | 106.08222 | 70.71467 | 0.01052 | 0.00848 | 0.83063 |
| 151636 | 53.42420 | 13.07918 | 118.39599 | 79.83609 | 0.01102 | 0.00848 | 0.83223 |
| 1236 | 43.95872 | 11.72201 | 127.44761 | 65.47000 | 0.01226 | 0.01116 | 0.83256 |
| 64780 | 39.57488 | 11.86410 | 113.14271 | 79.65169 | 0.00979 | 0.00862 | 0.83261 |
| 652 | 27.18893 | 24.10954 | 95.45501 | 84.03813 | 0.00894 | 0.00925 | 0.83286 |
| 221188 | 52.12892 | 11.25671 | 136.87754 | 71.56786 | 0.01087 | 0.00810 | 0.83337 |
| 80863 | 37.82874 | 12.93589 | 105.51530 | 79.53361 | 0.01007 | 0.00915 | 0.83356 |
| 54659 | 36.01508 | 12.65764 | 104.99257 | 70.79344 | 0.01084 | 0.00867 | 0.83382 |
| 3385 | 52.97387 | 10.94805 | 127.94036 | 72.42144 | 0.01061 | 0.00819 | 0.83651 |
| 8671 | 37.60168 | 15.34638 | 109.64073 | 72.00864 | 0.00948 | 0.00765 | 0.83658 |
| 80790 | 21.42274 | 18.00331 | 90.01805 | 85.74904 | 0.00892 | 0.00881 | 0.83670 |
| 282991 | −1.35229 | 13.44653 | 70.63279 | 78.16162 | 0.00790 | 0.00829 | 0.83706 |
| 3624 | 39.32452 | 19.31748 | 110.77369 | 84.83336 | 0.00915 | 0.00757 | 0.84133 |
| 8875 | 49.42235 | 22.61988 | 119.09363 | 82.32962 | 0.01090 | 0.00874 | 0.84152 |
| 9267 | 39.89000 | 11.26623 | 109.79900 | 77.72958 | 0.01016 | 0.00792 | 0.84189 |
| 50863 | 40.35883 | 14.86484 | 108.02357 | 85.53347 | 0.00971 | 0.00824 | 0.84200 |
| 925 | 132.46887 | 18.29649 | 179.85158 | 23.93083 | 0.01092 | 0.00267 | 0.26197 |
| 916 | 133.93218 | 12.89002 | 184.35881 | 22.34171 | 0.01114 | 0.00263 | 0.27279 |
| 914 | 131.23760 | 14.88456 | 188.56867 | 25.34725 | 0.01157 | 0.00332 | 0.29831 |
| 915 | 117.38132 | 14.63689 | 176.43983 | 28.28830 | 0.01227 | 0.00508 | 0.31877 |

TABLE 2-continued

| | | | | | | | |
|---|---|---|---|---|---|---|---|
| 149628 | 132.73069 | 12.31325 | 171.50480 | 27.14178 | 0.00977 | 0.00285 | 0.33732 |
| 3702 | 118.32179 | 10.54127 | 166.43669 | 27.24559 | 0.01044 | 0.00282 | 0.34360 |
| 10225 | 123.34174 | 9.46925 | 165.78766 | 30.65280 | 0.01036 | 0.00362 | 0.34408 |
| 387357 | 117.00730 | 10.79152 | 178.02784 | 31.01831 | 0.01174 | 0.00351 | 0.35205 |
| 114836 | 125.11731 | 19.09206 | 170.82197 | 33.09353 | 0.01026 | 0.00344 | 0.35821 |
| 50852 | 121.75371 | 13.88679 | 160.19686 | 29.99529 | 0.00981 | 0.00370 | 0.36545 |
| 84636 | 132.80946 | 5.95025 | 180.20267 | 29.22073 | 0.01029 | 0.00346 | 0.37054 |
| 962 | 127.26747 | 8.42451 | 179.64518 | 27.75532 | 0.01088 | 0.00340 | 0.37063 |
| 57823 | 122.77484 | 12.48054 | 175.50296 | 32.91310 | 0.01025 | 0.00356 | 0.38515 |
| 4283 | 123.60807 | 6.36385 | 164.83864 | 30.52667 | 0.00988 | 0.00328 | 0.39029 |
| 29851 | 106.09183 | 12.72677 | 166.62829 | 34.16291 | 0.01142 | 0.00447 | 0.39802 |
| 128611 | 116.67694 | 9.05224 | 150.07781 | 34.37668 | 0.00900 | 0.00354 | 0.40126 |
| 3683 | 119.15373 | 8.60030 | 176.00370 | 33.41992 | 0.01079 | 0.00412 | 0.40299 |
| 10320 | 117.08934 | 5.43061 | 176.92176 | 31.40813 | 0.01096 | 0.00363 | 0.41123 |
| 6504 | 110.68923 | 9.79623 | 172.72428 | 33.38671 | 0.01120 | 0.00401 | 0.41215 |
| 645432 | 111.81413 | 11.07637 | 153.50283 | 36.64844 | 0.00980 | 0.00378 | 0.41608 |
| 80342 | 113.19331 | 11.37108 | 162.33821 | 38.47857 | 0.01078 | 0.00415 | 0.41698 |
| 9402 | 117.69073 | 9.48485 | 167.66451 | 31.74649 | 0.01028 | 0.00361 | 0.42026 |
| 919 | 115.87243 | 7.03211 | 162.35794 | 35.42517 | 0.00974 | 0.00372 | 0.42049 |
| 3003 | 108.46256 | 10.75190 | 166.34588 | 35.53013 | 0.01106 | 0.00398 | 0.42425 |
| 51411 | 117.30196 | 7.92136 | 176.58712 | 33.10866 | 0.01086 | 0.00372 | 0.42796 |
| 5551 | 106.23376 | 11.21409 | 154.18474 | 39.19618 | 0.00992 | 0.00411 | 0.42805 |
| 4063 | 116.06616 | 7.41292 | 158.25594 | 33.98378 | 0.00997 | 0.00372 | 0.43109 |
| 100506736 | 117.54280 | 13.54147 | 169.53244 | 42.72690 | 0.01057 | 0.00419 | 0.43395 |
| 3587 | 116.03577 | 7.99997 | 174.97051 | 34.18446 | 0.01102 | 0.00370 | 0.43776 |
| 27334 | 106.37952 | 14.22478 | 160.39567 | 36.86228 | 0.01081 | 0.00403 | 0.43895 |
| 165631 | 111.44208 | 10.30576 | 165.56899 | 38.31349 | 0.01107 | 0.00415 | 0.44138 |
| 1794 | 116.87392 | 7.66347 | 176.36212 | 35.32146 | 0.01097 | 0.00425 | 0.44563 |
| 53347 | 111.01662 | 5.90117 | 172.27339 | 36.94182 | 0.01093 | 0.00451 | 0.44831 |
| 115362 | 121.79847 | 9.47539 | 168.77173 | 36.72659 | 0.01003 | 0.00421 | 0.45166 |
| 917 | 113.20245 | 5.78312 | 167.81893 | 31.97522 | 0.01026 | 0.00421 | 0.45194 |
| 1493 | 104.35232 | 14.78784 | 165.22580 | 39.86139 | 0.01169 | 0.00502 | 0.45277 |
| 64926 | 107.57037 | 11.93173 | 176.81526 | 35.32880 | 0.01198 | 0.00403 | 0.45618 |
| 4068 | 115.24678 | 5.59277 | 178.62097 | 31.33717 | 0.01041 | 0.00360 | 0.45736 |
| 30009 | 100.63393 | 7.39648 | 153.82326 | 34.50429 | 0.00990 | 0.00373 | 0.46039 |
| 7535 | 107.79463 | 11.12895 | 163.64242 | 39.02380 | 0.01038 | 0.00415 | 0.46559 |
| 3560 | 95.06219 | 10.13894 | 168.18687 | 41.18957 | 0.01245 | 0.00657 | 0.47531 |
| 5294 | 108.87132 | 7.44934 | 172.45530 | 39.04218 | 0.01114 | 0.00404 | 0.47703 |
| 2633 | 105.27573 | 20.22381 | 148.09733 | 43.90399 | 0.01026 | 0.00433 | 0.47944 |
| 64333 | 107.09157 | 13.47478 | 157.92832 | 38.70094 | 0.01005 | 0.00426 | 0.48115 |
| 55843 | 104.29020 | 7.95075 | 165.36530 | 38.00935 | 0.01153 | 0.00428 | 0.48608 |
| 952 | 100.67975 | 18.61407 | 158.59179 | 45.54358 | 0.01064 | 0.00453 | 0.48897 |
| 11262 | 96.39771 | 13.99468 | 174.44917 | 40.05028 | 0.01230 | 0.00495 | 0.48949 |
| 695 | 96.31108 | 5.59876 | 170.25131 | 37.10761 | 0.01217 | 0.00413 | 0.49320 |
| 3561 | 95.48508 | 8.74903 | 162.73838 | 40.11315 | 0.01157 | 0.00550 | 0.49716 |
| 101929889 | 104.38252 | 9.42204 | 172.15231 | 39.56659 | 0.01188 | 0.00485 | 0.49807 |
| 6693 | 104.38252 | 9.42204 | 172.15231 | 39.56659 | 0.01188 | 0.00485 | 0.49807 |
| 117289 | 102.03624 | 15.43525 | 160.45010 | 42.93780 | 0.01088 | 0.00438 | 0.49980 |
| 10563 | 105.22786 | 12.20707 | 152.79695 | 44.68870 | 0.00992 | 0.00482 | 0.50154 |
| 8302 | 96.43330 | 16.18173 | 153.59506 | 50.77142 | 0.01041 | 0.00563 | 0.50192 |
| 80008 | 103.79367 | 10.69148 | 162.79523 | 42.91688 | 0.01037 | 0.00429 | 0.50202 |
| 115352 | 99.39562 | 11.74043 | 151.54439 | 43.86855 | 0.01061 | 0.00453 | 0.50320 |
| 147138 | 109.23256 | 11.10203 | 173.70442 | 39.71838 | 0.01103 | 0.00445 | 0.50813 |
| 356 | 98.09735 | 6.24900 | 162.55232 | 39.91570 | 0.01129 | 0.00442 | 0.50903 |
| 26191 | 100.35709 | 18.91938 | 165.86877 | 46.38119 | 0.01168 | 0.00543 | 0.51038 |
| 3575 | 99.32053 | 12.71791 | 159.34036 | 41.81554 | 0.01044 | 0.00447 | 0.51145 |
| 4046 | 93.55675 | 8.11861 | 145.34576 | 42.29249 | 0.01063 | 0.00475 | 0.51219 |
| 1536 | 108.72728 | 6.64746 | 175.55749 | 38.53193 | 0.01126 | 0.00406 | 0.51253 |
| 6352 | 89.44945 | 5.99922 | 171.92569 | 33.06592 | 0.01261 | 0.00731 | 0.51342 |
| 8832 | 99.86605 | 8.51703 | 168.97805 | 41.27310 | 0.01132 | 0.00547 | 0.51998 |
| 3662 | 96.57416 | 9.21514 | 154.88667 | 44.52140 | 0.01025 | 0.00483 | 0.52522 |
| 3627 | 101.79815 | 8.82904 | 147.63854 | 43.13246 | 0.00985 | 0.00449 | 0.52650 |
| 64092 | 96.53302 | 5.05011 | 159.85401 | 38.69263 | 0.01024 | 0.00424 | 0.52739 |
| 3458 | 106.60667 | 6.39166 | 169.61890 | 42.58520 | 0.01062 | 0.00470 | 0.53630 |
| 9404 | 96.26452 | 21.76770 | 165.76714 | 48.71138 | 0.01127 | 0.00513 | 0.53821 |
| 729230 | 99.92119 | 11.55690 | 179.55369 | 44.15642 | 0.01212 | 0.00500 | 0.54503 |
| 1233 | 89.70372 | 7.12215 | 150.11956 | 41.71310 | 0.01014 | 0.00496 | 0.54588 |
| 79931 | 93.41558 | 21.86794 | 147.02841 | 49.77474 | 0.01054 | 0.00555 | 0.54753 |
| 115361 | 97.93410 | 29.78883 | 138.35246 | 57.26008 | 0.00926 | 0.00552 | 0.55001 |
| 4332 | 91.13200 | 8.73738 | 149.45156 | 42.35489 | 0.01048 | 0.00473 | 0.55017 |
| 923 | 89.77222 | 8.71504 | 149.82150 | 43.16582 | 0.01042 | 0.00476 | 0.55313 |
| 4064 | 93.83193 | 6.93479 | 153.71439 | 47.07478 | 0.01035 | 0.00525 | 0.55812 |
| 10673 | 101.79869 | 6.86652 | 163.40567 | 44.99960 | 0.01087 | 0.00505 | 0.56462 |
| 3134 | 96.92569 | 17.88404 | 145.74897 | 51.57694 | 0.00955 | 0.00527 | 0.56847 |
| 313 | 107.29637 | 5.04276 | 169.57604 | 44.69271 | 0.01078 | 0.00486 | 0.56944 |
| 51056 | 92.54992 | 15.30238 | 141.68211 | 52.07536 | 0.00989 | 0.00540 | 0.57003 |
| 80833 | 96.66312 | 11.26206 | 154.57096 | 53.94460 | 0.01084 | 0.00516 | 0.57043 |
| 100528032 | 95.93514 | 16.21324 | 163.05155 | 54.22077 | 0.01065 | 0.00561 | 0.57115 |
| 22914 | 95.93514 | 16.21324 | 163.05155 | 54.22077 | 0.01065 | 0.00561 | 0.57115 |
| 199 | 85.56611 | 7.81703 | 150.61633 | 46.17227 | 0.01137 | 0.00556 | 0.57168 |

TABLE 2-continued

| | | | | | | | |
|---:|---:|---:|---:|---:|---:|---:|---:|
| 29126 | 81.60203 | 14.13583 | 139.09936 | 51.54096 | 0.01058 | 0.00601 | 0.57356 |
| 225 | 90.72288 | 25.77552 | 143.31608 | 61.31422 | 0.00968 | 0.00599 | 0.57460 |
| 5778 | 90.81931 | 14.10946 | 157.26388 | 46.58757 | 0.01105 | 0.00520 | 0.57462 |
| 567 | 95.78378 | 17.04518 | 158.23538 | 51.97684 | 0.01061 | 0.00524 | 0.57954 |
| 6775 | 91.99588 | 10.91435 | 162.55531 | 51.22044 | 0.01088 | 0.00533 | 0.58492 |
| 4818 | 85.36120 | 11.72280 | 150.78838 | 50.94266 | 0.01089 | 0.00605 | 0.58562 |
| 2207 | 90.54658 | 5.67149 | 161.68595 | 45.60882 | 0.01088 | 0.00520 | 0.58623 |
| 3604 | 85.12915 | 5.45326 | 153.02287 | 42.02596 | 0.01085 | 0.00539 | 0.58687 |
| 3682 | 77.60302 | 7.78041 | 148.68418 | 49.74072 | 0.01106 | 0.00612 | 0.58957 |
| 6890 | 86.73422 | 23.12621 | 142.66366 | 58.80568 | 0.01078 | 0.00644 | 0.59142 |
| 55340 | 92.60007 | 6.47920 | 167.73807 | 45.53285 | 0.01176 | 0.00480 | 0.59361 |
| 10666 | 91.26894 | 7.67466 | 157.76778 | 50.19185 | 0.01075 | 0.00512 | 0.59536 |
| 64581 | 88.71665 | 6.94110 | 148.66998 | 47.05405 | 0.01045 | 0.00474 | 0.59597 |
| 5698 | 94.09534 | 19.10426 | 144.84165 | 55.46439 | 0.00972 | 0.00539 | 0.59635 |
| 6373 | 90.72499 | 8.75213 | 146.53072 | 48.95605 | 0.01058 | 0.00485 | 0.59651 |
| 441168 | 90.70116 | 16.22806 | 144.49771 | 54.54732 | 0.01037 | 0.00572 | 0.59937 |
| 100423062 | 90.18182 | 5.71107 | 156.05802 | 48.33666 | 0.01071 | 0.00495 | 0.59950 |
| 1071 | 91.17916 | 9.54219 | 147.25928 | 53.12205 | 0.01031 | 0.00573 | 0.60049 |
| 100527949 | 104.17220 | 5.43079 | 167.50763 | 45.77021 | 0.01038 | 0.00489 | 0.60382 |
| 3659 | 79.31865 | 30.22253 | 136.63928 | 61.83805 | 0.01014 | 0.00551 | 0.60584 |
| 154075 | 85.66716 | 11.05534 | 160.11112 | 52.95588 | 0.01102 | 0.00563 | 0.60990 |
| 653361 | 80.66753 | 5.54485 | 144.90555 | 50.21386 | 0.01027 | 0.00578 | 0.61196 |
| 92241 | 85.13870 | 9.26042 | 155.01767 | 46.97921 | 0.01155 | 0.00525 | 0.61310 |
| 834 | 83.29509 | 6.00292 | 149.93766 | 50.44030 | 0.01073 | 0.00543 | 0.61425 |
| 57705 | 91.10238 | 8.42721 | 155.94644 | 50.90703 | 0.01124 | 0.00506 | 0.61729 |
| 81030 | 86.08957 | 6.59619 | 147.48925 | 47.45504 | 0.01071 | 0.00573 | 0.61833 |
| 5026 | 82.73410 | 12.38147 | 137.26640 | 54.47773 | 0.01002 | 0.00600 | 0.61886 |
| 9046 | 79.58734 | 7.00718 | 157.12434 | 48.31603 | 0.01247 | 0.00608 | 0.62107 |
| 55911 | 70.54267 | 5.77443 | 136.80134 | 51.19045 | 0.01238 | 0.00694 | 0.62454 |
| 102725018 | 85.20471 | 6.36191 | 149.26132 | 51.22154 | 0.01057 | 0.00546 | 0.62533 |
| 973 | 85.18442 | 11.75279 | 152.32893 | 54.22476 | 0.01134 | 0.00558 | 0.62807 |
| 219285 | 89.83587 | 5.86281 | 144.25444 | 50.47000 | 0.00997 | 0.00522 | 0.63072 |
| 5133 | 79.40986 | 5.34058 | 131.90773 | 58.24841 | 0.00930 | 0.00639 | 0.63184 |
| 89790 | 85.22522 | 7.81127 | 149.30224 | 51.01999 | 0.01008 | 0.00550 | 0.63598 |
| 27240 | 76.49493 | 7.11166 | 146.62189 | 54.75766 | 0.01146 | 0.00619 | 0.63969 |
| 27299 | 81.33400 | 5.14655 | 156.98788 | 47.51924 | 0.01100 | 0.00580 | 0.64045 |
| 9051 | 89.86342 | 8.53248 | 160.88631 | 53.94924 | 0.01117 | 0.00556 | 0.64581 |
| 3738 | 78.53332 | 21.26959 | 145.34405 | 62.38270 | 0.01163 | 0.00605 | 0.64591 |
| 89857 | 89.23379 | 14.21749 | 151.59460 | 56.86102 | 0.01085 | 0.00627 | 0.64615 |
| 51744 | 68.96590 | 7.78655 | 134.83225 | 52.58498 | 0.01046 | 0.00649 | 0.64738 |
| 10538 | 77.27067 | 11.98959 | 156.54463 | 48.24031 | 0.01184 | 0.00587 | 0.64846 |
| 27128 | 85.58750 | 5.69072 | 153.09451 | 51.85922 | 0.01129 | 0.00574 | 0.65084 |
| 80830 | 83.98319 | 17.03071 | 155.41408 | 55.73009 | 0.01117 | 0.00653 | 0.65243 |
| 146722 | 82.72179 | 6.44087 | 148.68993 | 50.30402 | 0.01028 | 0.00568 | 0.65245 |
| 340152 | 77.61859 | 8.91021 | 149.21506 | 53.62821 | 0.01135 | 0.00607 | 0.65425 |
| 120425 | 82.00793 | 7.19969 | 156.21352 | 50.51242 | 0.01141 | 0.00524 | 0.65733 |
| 221472 | 79.28695 | 10.35114 | 150.44535 | 57.71451 | 0.01187 | 0.00636 | 0.65969 |
| 8807 | 73.63819 | 13.22794 | 142.38568 | 58.56197 | 0.01089 | 0.00687 | 0.66078 |
| 3512 | 86.52446 | 5.60505 | 156.69237 | 57.00721 | 0.01122 | 0.00599 | 0.66336 |
| 5790 | 71.67447 | 7.29587 | 128.44758 | 61.35845 | 0.00989 | 0.00623 | 0.66446 |
| 3603 | 75.26950 | 13.87542 | 131.74493 | 61.75342 | 0.01015 | 0.00565 | 0.66524 |
| 6891 | 80.51280 | 21.30470 | 134.50722 | 60.00391 | 0.00971 | 0.00617 | 0.66652 |
| 9744 | 73.44253 | 11.35831 | 149.81950 | 58.71249 | 0.01181 | 0.00630 | 0.67015 |
| 197135 | 85.76842 | 19.47486 | 139.95287 | 65.65495 | 0.00940 | 0.00684 | 0.67301 |
| 6772 | 74.52271 | 10.30336 | 131.94226 | 62.91232 | 0.01040 | 0.00619 | 0.67498 |
| 51513 | 86.52372 | 13.00134 | 143.15852 | 57.61892 | 0.01002 | 0.00563 | 0.67520 |
| 1520 | 87.68917 | 6.02294 | 171.98825 | 49.36624 | 0.01179 | 0.00620 | 0.67821 |
| 9214 | 82.95540 | 6.10937 | 160.02711 | 53.37932 | 0.01155 | 0.00650 | 0.68181 |
| 54625 | 73.58426 | 21.37131 | 131.20026 | 69.23161 | 0.01052 | 0.00722 | 0.68289 |
| 2634 | 68.27766 | 10.76840 | 143.43607 | 57.73826 | 0.01138 | 0.00670 | 0.68590 |
| 26279 | 76.99458 | 5.52123 | 155.07406 | 54.59525 | 0.01040 | 0.00544 | 0.68758 |
| 489 | 67.68474 | 8.97458 | 130.24366 | 61.79580 | 0.00998 | 0.00676 | 0.68801 |
| 341 | 74.19059 | 5.82340 | 152.35227 | 53.06582 | 0.01143 | 0.00643 | 0.69060 |
| 1318 | 72.98302 | 17.68887 | 134.70251 | 62.17808 | 0.01010 | 0.00606 | 0.69387 |
| 926 | 66.48779 | 8.96143 | 143.20925 | 56.18168 | 0.01080 | 0.00704 | 0.69692 |
| 64135 | 69.68008 | 17.79180 | 122.38841 | 62.68430 | 0.00951 | 0.00636 | 0.70307 |
| 5552 | 68.30857 | 5.81153 | 145.26790 | 56.05875 | 0.01145 | 0.00608 | 0.70392 |
| 5293 | 79.85345 | 7.70086 | 142.86906 | 56.69066 | 0.00958 | 0.00608 | 0.70465 |
| 25816 | 71.83670 | 11.30326 | 142.56470 | 61.58315 | 0.01035 | 0.00707 | 0.70658 |
| 9056 | 64.35888 | 11.02274 | 138.18480 | 54.93858 | 0.01063 | 0.00816 | 0.71116 |
| 116449 | 75.39628 | 7.68924 | 157.51504 | 55.70947 | 0.01102 | 0.00601 | 0.71226 |
| 50856 | 63.35701 | 5.97076 | 125.27345 | 61.06849 | 0.00984 | 0.00586 | 0.71227 |
| 7185 | 71.03510 | 10.29482 | 130.87641 | 61.37305 | 0.00958 | 0.00624 | 0.71272 |
| 5696 | 76.67496 | 22.78305 | 131.73241 | 74.99409 | 0.01013 | 0.00759 | 0.71298 |
| 3117 | 69.33569 | 14.57142 | 140.11202 | 63.22185 | 0.01062 | 0.00652 | 0.71308 |
| 51237 | 76.10019 | 12.80387 | 150.60321 | 61.05290 | 0.01141 | 0.00658 | 0.71665 |
| 79368 | 72.52709 | 9.39197 | 136.69421 | 64.42200 | 0.01061 | 0.00632 | 0.71733 |
| 25780 | 68.80723 | 11.97515 | 135.60895 | 62.21749 | 0.01101 | 0.00678 | 0.72213 |
| 51296 | 68.46611 | 9.72774 | 135.60691 | 59.33931 | 0.01198 | 0.00669 | 0.72628 |
| 100509457 | 68.30667 | 15.04428 | 137.79972 | 65.14500 | 0.01044 | 0.00613 | 0.72876 |

TABLE 2-continued

| | | | | | | | |
|---|---|---|---|---|---|---|---|
| 2643 | 70.26464 | 11.70748 | 143.41268 | 61.91503 | 0.01072 | 0.00705 | 0.73073 |
| 83937 | 75.40572 | 8.68154 | 153.41273 | 56.87214 | 0.01120 | 0.00567 | 0.73639 |
| 150372 | 65.69703 | 5.25704 | 139.67446 | 55.46383 | 0.01162 | 0.00721 | 0.73760 |
| 23526 | 61.03539 | 9.23143 | 151.16644 | 59.84711 | 0.01290 | 0.00762 | 0.73924 |
| 6916 | 75.84286 | 6.20168 | 156.55428 | 60.93057 | 0.01167 | 0.00628 | 0.74250 |
| 3123 | 72.84865 | 8.16628 | 150.84031 | 59.75881 | 0.01172 | 0.00677 | 0.74458 |
| 102723407 | 75.93399 | 5.03645 | 138.74351 | 60.54263 | 0.00948 | 0.00609 | 0.74513 |
| 25939 | 72.51134 | 8.66075 | 153.96000 | 57.42418 | 0.01199 | 0.00743 | 0.74904 |
| 1806 | 68.41470 | 13.97356 | 135.90536 | 69.18360 | 0.01104 | 0.00703 | 0.75312 |
| 160365 | 61.95310 | 8.98446 | 136.66442 | 58.56895 | 0.01057 | 0.00676 | 0.75476 |
| 3635 | 73.28658 | 8.23166 | 160.14450 | 60.32852 | 0.01236 | 0.00657 | 0.75533 |
| 2124 | 68.36587 | 6.00550 | 143.22433 | 59.23862 | 0.01033 | 0.00647 | 0.75964 |
| 3431 | 67.85569 | 7.57238 | 134.72968 | 58.81245 | 0.01074 | 0.00650 | 0.76262 |
| 9111 | 60.82240 | 11.47109 | 121.27965 | 69.01749 | 0.00965 | 0.00745 | 0.76797 |
| 4261 | 68.76751 | 7.71196 | 142.63347 | 60.78440 | 0.01094 | 0.00646 | 0.76830 |
| 3108 | 68.64809 | 12.33576 | 143.52614 | 65.73080 | 0.01079 | 0.00747 | 0.76969 |
| 10791 | 60.96002 | 7.98801 | 135.45241 | 65.46077 | 0.01056 | 0.00736 | 0.77038 |
| 5734 | 64.87056 | 5.57321 | 141.18999 | 57.28328 | 0.01072 | 0.00643 | 0.77377 |
| 57713 | 60.53831 | 21.94007 | 124.40193 | 74.36285 | 0.01060 | 0.00740 | 0.78204 |
| 11118 | 62.70905 | 22.99701 | 127.88520 | 78.05679 | 0.01059 | 0.00822 | 0.78389 |
| 5027 | 61.00043 | 8.62227 | 135.52896 | 68.52551 | 0.01169 | 0.00703 | 0.78577 |
| 3105 | 67.17138 | 7.66897 | 141.25231 | 63.12921 | 0.01002 | 0.00654 | 0.78593 |
| 2014 | 62.83667 | 7.88366 | 128.22903 | 67.25077 | 0.01043 | 0.00666 | 0.79097 |
| 26157 | 63.26634 | 7.52504 | 140.40815 | 68.96011 | 0.01069 | 0.00720 | 0.79249 |
| 11119 | 61.03069 | 20.84164 | 126.43252 | 77.13378 | 0.01031 | 0.00765 | 0.80404 |
| 55016 | 60.34485 | 5.00504 | 142.42274 | 63.28249 | 0.01181 | 0.00700 | 0.80671 |
| 10384 | 63.72442 | 15.08478 | 135.67743 | 70.88642 | 0.01069 | 0.00758 | 0.82158 |
| 118788 | 65.46841 | 7.30700 | 150.38569 | 65.68488 | 0.01153 | 0.00738 | 0.82521 |
| 2313 | 67.14551 | 9.32111 | 150.85811 | 67.27955 | 0.01202 | 0.00688 | 0.82689 |
| 1234 | 127.65473 | 3.92105 | 187.10196 | 29.48237 | 0.01172 | 0.00346 | 0.36352 |
| 55423 | 102.94246 | 0.27420 | 177.50330 | 33.52955 | 0.01212 | 0.00438 | 0.41887 |
| 50615 | 106.65259 | −1.47190 | 160.68772 | 31.55578 | 0.01035 | 0.00336 | 0.42019 |
| 257101 | 113.17840 | 4.16811 | 171.33881 | 36.51843 | 0.01042 | 0.00419 | 0.48224 |
| 963 | 110.53518 | 3.25201 | 171.32772 | 37.49119 | 0.01077 | 0.00418 | 0.49033 |
| 2999 | 113.77353 | 3.94566 | 172.10120 | 37.00820 | 0.01049 | 0.00461 | 0.49146 |
| 5788 | 105.46083 | 4.49207 | 171.27444 | 35.59486 | 0.01121 | 0.00512 | 0.49381 |
| 3937 | 106.09125 | 4.55122 | 165.23620 | 38.64909 | 0.01081 | 0.00414 | 0.50019 |
| 399 | 100.75618 | 3.10814 | 149.97003 | 38.35955 | 0.00983 | 0.00404 | 0.50144 |
| 56833 | 112.15579 | 4.63548 | 169.26160 | 38.31825 | 0.01060 | 0.00497 | 0.50321 |
| 2359 | 105.99579 | 4.38794 | 176.08598 | 34.66006 | 0.01071 | 0.00404 | 0.50493 |
| 84868 | 102.33990 | 2.57376 | 173.58954 | 37.46459 | 0.01135 | 0.00409 | 0.50714 |
| 201633 | 100.58867 | −2.37600 | 157.40864 | 34.96740 | 0.01043 | 0.00425 | 0.50983 |
| 168537 | 104.79463 | 1.82749 | 153.16616 | 40.45759 | 0.00959 | 0.00417 | 0.51018 |
| 22797 | 100.21092 | −1.91337 | 175.45693 | 29.78683 | 0.01132 | 0.00401 | 0.51234 |
| 942 | 93.79277 | 4.30693 | 145.61564 | 40.25785 | 0.00978 | 0.00436 | 0.51691 |
| 2533 | 104.01083 | 3.41810 | 166.72533 | 36.58293 | 0.01048 | 0.00456 | 0.51793 |
| 3071 | 104.72259 | 4.20027 | 173.89453 | 36.53594 | 0.01110 | 0.00461 | 0.51995 |
| 3932 | 102.55358 | 3.33079 | 167.22468 | 36.76962 | 0.01058 | 0.00472 | 0.52058 |
| 128346 | 90.91598 | 3.89621 | 145.84690 | 38.81794 | 0.01021 | 0.00421 | 0.52074 |
| 54900 | 106.73124 | 3.85337 | 161.63662 | 40.74484 | 0.00987 | 0.00453 | 0.52154 |
| 55303 | 107.34248 | 3.36874 | 172.63715 | 39.71747 | 0.01076 | 0.00430 | 0.52943 |
| 8477 | 104.57577 | 1.50534 | 169.33264 | 37.36588 | 0.01048 | 0.00405 | 0.53463 |
| 54440 | 99.07711 | 3.42177 | 167.64467 | 42.88777 | 0.01144 | 0.00473 | 0.54394 |
| 84174 | 97.33791 | 0.53203 | 151.21515 | 41.08077 | 0.00949 | 0.00478 | 0.54562 |
| 920 | 102.07401 | 3.13176 | 152.06315 | 39.97909 | 0.00951 | 0.00460 | 0.54639 |
| 5341 | 94.10478 | 2.40840 | 163.24582 | 41.71978 | 0.01131 | 0.00465 | 0.55497 |
| 1043 | 97.21454 | −0.48789 | 174.29424 | 36.34138 | 0.01135 | 0.00546 | 0.55512 |
| 445347 | 87.61347 | 4.38534 | 156.90199 | 42.74712 | 0.01049 | 0.00578 | 0.55635 |
| 64005 | 92.53071 | 4.26664 | 168.82952 | 40.11309 | 0.01190 | 0.00457 | 0.55773 |
| 3676 | 103.53520 | 4.95413 | 165.88512 | 39.65685 | 0.01036 | 0.00439 | 0.55930 |
| 8320 | 103.77495 | −3.52951 | 180.85378 | 35.96204 | 0.01085 | 0.00432 | 0.56351 |
| 3903 | 95.70473 | 2.24170 | 173.32303 | 43.67922 | 0.01168 | 0.00494 | 0.56422 |
| 941 | 98.00337 | 3.19719 | 159.27300 | 39.47283 | 0.01005 | 0.00521 | 0.56959 |
| 7805 | 99.49486 | 1.72013 | 165.33048 | 41.55008 | 0.01052 | 0.00489 | 0.57081 |
| 256380 | 82.83181 | 0.28667 | 154.56627 | 41.55361 | 0.01146 | 0.00526 | 0.57967 |
| 3001 | 96.62391 | 1.41260 | 162.62651 | 41.60512 | 0.01047 | 0.00539 | 0.58931 |
| 1521 | 75.45276 | 3.61631 | 144.69165 | 46.93261 | 0.01144 | 0.00569 | 0.59151 |
| 9447 | 89.18421 | −4.59938 | 143.07625 | 44.43326 | 0.00967 | 0.00507 | 0.59485 |
| 9535 | 97.28306 | 3.31791 | 156.57246 | 43.04832 | 0.00995 | 0.00491 | 0.59513 |
| 3594 | 100.25272 | 3.13245 | 160.97514 | 50.23059 | 0.01053 | 0.00554 | 0.59947 |
| 3002 | 97.56249 | 3.70026 | 156.76569 | 46.22616 | 0.00959 | 0.00501 | 0.59949 |
| 11151 | 90.14177 | −1.36732 | 157.85376 | 39.93976 | 0.01059 | 0.00447 | 0.60224 |
| 257106 | 92.97246 | −0.09334 | 156.75068 | 42.76178 | 0.01042 | 0.00451 | 0.60233 |
| 713 | 92.80672 | 0.47790 | 161.72498 | 43.59288 | 0.01057 | 0.00466 | 0.60309 |
| 7305 | 87.12905 | −1.33579 | 164.09025 | 41.18656 | 0.01127 | 0.00486 | 0.60388 |
| 8530 | 78.93325 | −0.23413 | 144.30259 | 47.37843 | 0.01035 | 0.00519 | 0.60852 |
| 7940 | 81.42373 | 1.30248 | 151.17978 | 41.51454 | 0.01077 | 0.00488 | 0.60868 |
| 11006 | 94.58501 | −5.35949 | 170.00476 | 41.05079 | 0.01086 | 0.00494 | 0.60953 |
| 64231 | 93.14525 | 2.10698 | 164.68751 | 43.29548 | 0.01077 | 0.00494 | 0.60989 |
| 6404 | 85.19813 | 4.42469 | 156.66956 | 44.64174 | 0.01113 | 0.00507 | 0.61165 |

TABLE 2-continued

| | | | | | | | |
|---|---|---|---|---|---|---|---|
| 23533 | 82.26444 | 2.00660 | 150.79667 | 44.11646 | 0.01060 | 0.00458 | 0.61313 |
| 219972 | 88.19342 | 3.39557 | 162.91737 | 44.59265 | 0.01114 | 0.00486 | 0.61477 |
| 1439 | 84.04980 | 3.34028 | 154.29053 | 46.87632 | 0.01087 | 0.00538 | 0.61847 |
| 10859 | 81.11953 | −1.81230 | 152.31463 | 44.65589 | 0.01119 | 0.00509 | 0.61891 |
| 6688 | 90.07522 | 0.56888 | 160.07804 | 44.09437 | 0.01097 | 0.00496 | 0.62040 |
| 56253 | 76.21249 | −2.68056 | 139.24669 | 45.96821 | 0.01013 | 0.00604 | 0.62389 |
| 83706 | 84.81626 | 3.96584 | 148.86031 | 50.49040 | 0.01090 | 0.00577 | 0.62404 |
| 2672 | 74.44434 | 3.98830 | 152.29944 | 44.48333 | 0.01124 | 0.00592 | 0.62455 |
| 9840 | 87.91168 | 0.32427 | 156.72914 | 47.13635 | 0.01059 | 0.00553 | 0.62455 |
| 7456 | 79.90563 | 1.41962 | 155.56805 | 43.61989 | 0.01100 | 0.00474 | 0.62585 |
| 4069 | 74.64151 | −2.94474 | 146.93579 | 44.56466 | 0.01045 | 0.00589 | 0.62726 |
| 26228 | 88.79817 | 4.39917 | 152.77557 | 51.66082 | 0.01086 | 0.00510 | 0.62732 |
| 6503 | 78.21187 | 4.99199 | 154.91762 | 49.81022 | 0.01207 | 0.00699 | 0.63181 |
| 139716 | 91.88982 | 4.29049 | 168.94246 | 51.12366 | 0.01245 | 0.00582 | 0.63663 |
| 714 | 80.61809 | −1.98322 | 162.56207 | 44.58052 | 0.01141 | 0.00534 | 0.64055 |
| 80231 | 81.49521 | −7.17672 | 147.67016 | 40.75078 | 0.01017 | 0.00445 | 0.64305 |
| 241 | 77.82758 | 4.47915 | 141.82300 | 52.49117 | 0.01059 | 0.00548 | 0.65585 |
| 712 | 80.24531 | 1.16896 | 163.17093 | 48.41308 | 0.01159 | 0.00567 | 0.65875 |
| 51225 | 85.58041 | 3.24299 | 152.27950 | 51.24696 | 0.01045 | 0.00563 | 0.65928 |
| 3687 | 78.03248 | 2.89094 | 149.65270 | 49.05506 | 0.01106 | 0.00580 | 0.66311 |
| 83416 | 84.71633 | −1.84101 | 155.19095 | 50.81523 | 0.01093 | 0.00546 | 0.66326 |
| 931 | 81.31713 | 3.27220 | 145.93179 | 55.50469 | 0.01075 | 0.00629 | 0.66623 |
| 6351 | 76.10244 | 1.18998 | 143.29700 | 54.91954 | 0.01094 | 0.00597 | 0.66879 |
| 924 | 75.81050 | 0.45365 | 148.63616 | 47.94176 | 0.01074 | 0.00579 | 0.67376 |
| 5330 | 80.72567 | 0.07391 | 156.33255 | 51.66496 | 0.01182 | 0.00587 | 0.67508 |
| 80380 | 81.00039 | 1.17098 | 156.70057 | 46.17450 | 0.01099 | 0.00575 | 0.67611 |
| 100293211 | 78.34811 | 4.28246 | 154.89069 | 57.06290 | 0.01174 | 0.00558 | 0.67893 |
| 397 | 85.10336 | 3.17425 | 165.10833 | 47.34753 | 0.01148 | 0.00585 | 0.68053 |
| 959 | 85.09541 | −0.27608 | 153.02680 | 52.88176 | 0.01018 | 0.00525 | 0.68304 |
| 64919 | 75.20953 | −3.29278 | 150.92875 | 47.50909 | 0.01068 | 0.00577 | 0.68305 |
| 10870 | 70.76905 | −2.64620 | 144.91065 | 51.24813 | 0.01091 | 0.00710 | 0.68542 |
| 8514 | 77.90397 | 0.18997 | 149.50324 | 50.54879 | 0.01045 | 0.00584 | 0.68666 |
| 4689 | 76.44884 | 4.75425 | 152.01086 | 54.38079 | 0.01162 | 0.00588 | 0.68782 |
| 91526 | 72.50884 | 0.72565 | 140.48769 | 51.95416 | 0.01090 | 0.00611 | 0.69015 |
| 2214 | 74.75131 | 0.37490 | 155.62859 | 51.49957 | 0.01194 | 0.00632 | 0.69038 |
| 3684 | 76.75668 | −1.89335 | 153.61208 | 50.82383 | 0.01143 | 0.00551 | 0.69081 |
| 84166 | 74.54244 | 1.25245 | 142.18479 | 49.97280 | 0.01010 | 0.00536 | 0.69342 |
| 719 | 77.47431 | 1.67065 | 158.35059 | 54.96463 | 0.01165 | 0.00583 | 0.69451 |
| 6402 | 70.99992 | −1.20570 | 143.47299 | 50.86437 | 0.01051 | 0.00570 | 0.69922 |
| 219855 | 70.58564 | 2.16587 | 141.17585 | 53.40986 | 0.01103 | 0.00606 | 0.70006 |
| 10333 | 76.28794 | 3.62303 | 150.67110 | 59.69887 | 0.01111 | 0.00557 | 0.71014 |
| 6039 | 76.18987 | 2.04088 | 143.58778 | 49.09400 | 0.00998 | 0.00556 | 0.71033 |
| 3689 | 71.89336 | −0.82920 | 158.66872 | 54.33917 | 0.01187 | 0.00560 | 0.71742 |
| 4481 | 74.03373 | 2.60794 | 146.25927 | 58.02520 | 0.01074 | 0.00561 | 0.71746 |
| 101060789 | 72.84700 | −1.06737 | 148.83683 | 52.25951 | 0.01097 | 0.00648 | 0.72792 |
| 972 | 71.63987 | 0.01651 | 148.44491 | 55.75164 | 0.01157 | 0.00608 | 0.73602 |
| 474344 | 74.28843 | 2.09883 | 153.85511 | 59.47095 | 0.01080 | 0.00592 | 0.73962 |
| 80896 | 70.43578 | −1.55911 | 150.65064 | 53.08572 | 0.01068 | 0.00550 | 0.74132 |
| 100049587 | 75.27710 | −0.06896 | 151.43117 | 50.93288 | 0.01068 | 0.00646 | 0.74426 |
| 100131897 | 70.84981 | 0.67662 | 149.81415 | 59.50378 | 0.01122 | 0.00606 | 0.74557 |
| 115350 | 72.36584 | −3.22877 | 141.83809 | 62.30798 | 0.01063 | 0.00624 | 0.75160 |
| 5450 | 70.55045 | 1.24450 | 148.20065 | 61.12277 | 0.01065 | 0.00655 | 0.77282 |
| 10288 | 66.28822 | 0.48589 | 127.91013 | 47.74697 | 0.01003 | 0.00549 | 0.65099 |
| 3394 | 65.28760 | 3.65624 | 134.90597 | 54.92136 | 0.01135 | 0.00644 | 0.67252 |
| 7454 | 55.18320 | 1.13790 | 122.42595 | 48.09606 | 0.00975 | 0.00587 | 0.69443 |
| 136647 | 5.35962 | 1.85714 | 56.09716 | 64.19140 | 0.00607 | 0.00615 | 0.69460 |
| 1230 | 69.27962 | −0.45970 | 145.00327 | 52.30491 | 0.01096 | 0.00555 | 0.69907 |
| 5880 | 67.64587 | 2.94719 | 148.39370 | 60.10039 | 0.01194 | 0.00635 | 0.70143 |
| 5996 | 64.12651 | −1.38379 | 136.18383 | 58.88934 | 0.01138 | 0.00643 | 0.71060 |
| 7462 | 67.40900 | 0.61016 | 132.25565 | 52.17792 | 0.01020 | 0.00636 | 0.71460 |
| 10578 | 57.52965 | 6.83042 | 121.06396 | 59.68905 | 0.00955 | 0.00637 | 0.71467 |
| 4688 | 66.60632 | 2.49651 | 146.76940 | 52.31282 | 0.01078 | 0.00610 | 0.71598 |
| 2213 | 66.51953 | −0.95318 | 147.29876 | 53.52706 | 0.01182 | 0.00639 | 0.71741 |
| 7634 | 59.82772 | −1.24460 | 127.66089 | 56.23341 | 0.00983 | 0.00669 | 0.72073 |
| 1908 | 63.64039 | 1.01726 | 127.18117 | 61.90460 | 0.00911 | 0.00586 | 0.72187 |
| 23495 | 68.20788 | 1.31645 | 137.88114 | 59.62642 | 0.01027 | 0.00579 | 0.72279 |
| 717 | 65.81684 | 0.82422 | 140.80149 | 59.71161 | 0.01110 | 0.00623 | 0.72482 |
| 158830 | 61.31413 | −7.40886 | 130.02324 | 54.19587 | 0.01050 | 0.00606 | 0.72489 |
| 100129083 | 61.93783 | 3.63712 | 136.55464 | 57.18902 | 0.01075 | 0.00650 | 0.72734 |
| 3936 | 61.87143 | −0.28151 | 142.13978 | 57.84167 | 0.01229 | 0.00708 | 0.72826 |
| 2212 | 67.99370 | 0.76188 | 147.08107 | 55.64183 | 0.01170 | 0.00627 | 0.73048 |
| 6356 | 54.71418 | 8.89251 | 119.79321 | 61.39001 | 0.00943 | 0.00652 | 0.73184 |
| 1240 | 69.36095 | 0.94835 | 151.12830 | 53.20022 | 0.01098 | 0.00566 | 0.73374 |
| 11040 | 58.13352 | 9.27554 | 140.52273 | 59.40708 | 0.01145 | 0.00689 | 0.73535 |
| 3821 | 50.81887 | 6.67730 | 119.19445 | 63.88703 | 0.00980 | 0.00705 | 0.73660 |
| 3858 | −0.50678 | 0.82123 | 57.51027 | 62.34264 | 0.00666 | 0.00683 | 0.74011 |
| 55013 | 68.43729 | 2.43874 | 141.81711 | 50.70110 | 0.00977 | 0.00602 | 0.74175 |
| 84541 | 50.85166 | 1.22838 | 115.63608 | 57.76760 | 0.00976 | 0.00625 | 0.74194 |
| 7727 | 14.40529 | 2.11399 | 73.18770 | 62.45171 | 0.00754 | 0.00666 | 0.74311 |
| 27180 | 58.62341 | −0.67150 | 132.98549 | 56.53434 | 0.01208 | 0.00718 | 0.74755 |

TABLE 2-continued

| | | | | | | | |
|---|---|---|---|---|---|---|---|
| 91543 | 63.16108 | 3.81224 | 125.58541 | 57.82716 | 0.01046 | 0.00634 | 0.75016 |
| 102724536 | 53.17032 | 9.89197 | 127.43420 | 72.78792 | 0.01069 | 0.00822 | 0.75086 |
| 22806 | 62.03377 | 1.94207 | 130.45336 | 57.08837 | 0.01017 | 0.00741 | 0.75346 |
| 4973 | 55.27239 | −2.85349 | 127.31841 | 52.60434 | 0.00973 | 0.00573 | 0.75448 |
| 10871 | 61.40985 | −2.75309 | 133.18321 | 52.71784 | 0.00977 | 0.00583 | 0.75466 |
| 8419 | 66.73951 | 1.23129 | 152.83202 | 46.55359 | 0.01122 | 0.00625 | 0.75483 |
| 971 | 59.41336 | 5.70045 | 136.11952 | 57.17595 | 0.01043 | 0.00669 | 0.75633 |
| 197259 | 67.57949 | 3.48482 | 146.96429 | 59.46607 | 0.01112 | 0.00704 | 0.75732 |
| 3559 | 66.01182 | −0.05703 | 148.84677 | 53.35594 | 0.01046 | 0.00597 | 0.75759 |
| 284759 | 44.79756 | 9.69705 | 125.46414 | 56.20379 | 0.01117 | 0.00845 | 0.75765 |
| 752 | 56.55209 | 1.60288 | 133.50585 | 60.10421 | 0.01070 | 0.00713 | 0.75900 |
| 55821 | 60.50159 | −0.17607 | 127.88092 | 60.69908 | 0.00927 | 0.00607 | 0.75960 |
| 94240 | 63.77556 | −3.56427 | 138.86911 | 53.83212 | 0.01026 | 0.00574 | 0.76124 |
| 11314 | 62.83242 | 2.34120 | 139.09276 | 56.22874 | 0.01084 | 0.00631 | 0.76132 |
| 115992 | 41.51517 | 2.04143 | 107.27256 | 60.64139 | 0.00872 | 0.00646 | 0.76152 |
| 3902 | 56.97909 | 7.77951 | 133.93615 | 61.23961 | 0.01106 | 0.00698 | 0.76485 |
| 2268 | 58.20014 | 1.79968 | 132.15316 | 56.91588 | 0.01032 | 0.00610 | 0.76533 |
| 50619 | 54.91167 | 4.08799 | 123.37730 | 60.26282 | 0.00937 | 0.00620 | 0.76636 |
| 9437 | 57.65200 | 6.16754 | 139.15142 | 59.40310 | 0.01086 | 0.00730 | 0.76701 |
| 124637 | 1.98376 | 1.85344 | 64.38490 | 65.92825 | 0.00747 | 0.00713 | 0.76718 |
| 23433 | 22.90552 | 9.61674 | 83.48395 | 64.33013 | 0.00804 | 0.00667 | 0.76809 |
| 2323 | 57.26420 | 3.94008 | 114.10534 | 65.16346 | 0.00885 | 0.00661 | 0.76828 |
| 5791 | 45.63373 | 3.75023 | 109.95433 | 62.94289 | 0.00963 | 0.00721 | 0.76942 |
| 4640 | 3.01149 | 7.46213 | 58.65750 | 66.53875 | 0.00951 | 0.00903 | 0.76957 |
| 81793 | 65.75953 | 1.41159 | 139.56691 | 62.62136 | 0.01064 | 0.00651 | 0.77025 |
| 3101 | 67.47988 | −2.33938 | 145.13172 | 53.69186 | 0.01043 | 0.00579 | 0.77121 |
| 338557 | 54.29394 | 7.26251 | 122.86208 | 66.23974 | 0.00982 | 0.00688 | 0.77361 |
| 974 | 51.87169 | 5.93472 | 122.48902 | 64.24794 | 0.01041 | 0.00671 | 0.77499 |
| 255231 | 52.31048 | 2.35981 | 127.92938 | 52.87273 | 0.01010 | 0.00700 | 0.77564 |
| 129607 | 59.48414 | 4.12430 | 126.78524 | 63.50472 | 0.01026 | 0.00659 | 0.77655 |
| 9034 | 55.62179 | −0.64799 | 141.25900 | 53.43767 | 0.01087 | 0.00590 | 0.77800 |
| 7097 | 66.38242 | 0.23990 | 143.68369 | 60.78023 | 0.01127 | 0.00639 | 0.77817 |
| 283234 | 52.34428 | 7.01203 | 131.10607 | 58.34524 | 0.01095 | 0.00631 | 0.77927 |
| 170575 | 56.26116 | −2.95005 | 138.63558 | 57.07862 | 0.01041 | 0.00667 | 0.77986 |
| 54491 | 59.72072 | 1.91648 | 129.42710 | 58.78011 | 0.00952 | 0.00651 | 0.78126 |
| 388336 | 21.26850 | 0.45362 | 84.50467 | 66.17216 | 0.00879 | 0.00711 | 0.78181 |
| 58475 | 66.73044 | 0.56528 | 145.11050 | 58.03338 | 0.01052 | 0.00598 | 0.78214 |
| 10437 | 53.93870 | 4.92816 | 135.88176 | 58.53452 | 0.01090 | 0.00696 | 0.78217 |
| 945 | 62.84198 | −4.61226 | 148.52650 | 52.42450 | 0.01155 | 0.00631 | 0.78239 |
| 100129697 | 54.76499 | 9.39237 | 129.04787 | 65.94740 | 0.01043 | 0.00770 | 0.78262 |
| 846 | 39.44157 | 4.05360 | 106.86677 | 65.73516 | 0.00923 | 0.00659 | 0.78291 |
| 2877 | 10.29673 | 3.19853 | 71.84656 | 63.91176 | 0.00981 | 0.00975 | 0.78532 |
| 4938 | 52.74062 | 4.05300 | 119.47506 | 58.87130 | 0.00992 | 0.00636 | 0.78592 |
| 27074 | 54.32287 | 8.56370 | 129.38150 | 66.91557 | 0.01139 | 0.00772 | 0.78659 |
| 23213 | 47.18140 | 2.53020 | 122.44071 | 66.76277 | 0.01000 | 0.00643 | 0.78664 |
| 101930405 | 64.41926 | 3.42382 | 134.78610 | 62.25268 | 0.01019 | 0.00649 | 0.78765 |
| 8728 | 53.56595 | 2.58188 | 122.54225 | 65.13083 | 0.00969 | 0.00703 | 0.78881 |
| 10200 | −6.28102 | −3.63692 | 61.67599 | 64.28527 | 0.00668 | 0.00688 | 0.78918 |
| 78989 | 55.97727 | 3.75118 | 130.76342 | 62.16437 | 0.00972 | 0.00690 | 0.79241 |
| 133418 | 54.75721 | −1.42517 | 133.50817 | 58.01722 | 0.01067 | 0.00656 | 0.79368 |
| 10537 | 56.06482 | 9.03488 | 126.76209 | 71.05793 | 0.01129 | 0.00758 | 0.79405 |
| 160364 | 64.93579 | −5.93459 | 147.14730 | 56.76060 | 0.01089 | 0.00652 | 0.79416 |
| 54 | 53.44482 | 8.50355 | 132.57193 | 65.90488 | 0.01153 | 0.00691 | 0.79464 |
| 54557 | 13.20409 | 4.27696 | 81.64026 | 67.17345 | 0.00796 | 0.00767 | 0.79655 |
| 8638 | 63.63813 | −0.31377 | 130.45321 | 60.46656 | 0.01025 | 0.00644 | 0.79664 |
| 409 | 53.99782 | 0.62373 | 140.14457 | 54.57062 | 0.01147 | 0.00759 | 0.79704 |
| 26033 | 44.52124 | 1.18111 | 113.47520 | 67.10866 | 0.00939 | 0.00663 | 0.79777 |
| 3383 | 52.47774 | 4.55490 | 131.39093 | 59.88872 | 0.01064 | 0.00679 | 0.79847 |
| 57715 | 42.38252 | 4.91818 | 106.79984 | 62.86747 | 0.00952 | 0.00657 | 0.79855 |
| 5142 | 55.79658 | 2.94358 | 131.75788 | 57.72304 | 0.01026 | 0.00656 | 0.79875 |
| 164668 | 69.14824 | −6.53408 | 150.40426 | 55.66483 | 0.01111 | 0.00663 | 0.80021 |
| 9246 | 60.36565 | 3.16236 | 131.88920 | 62.46688 | 0.01074 | 0.00657 | 0.80086 |
| 164118 | 49.01515 | 7.90988 | 120.61597 | 68.55666 | 0.01041 | 0.00776 | 0.80113 |
| 10993 | 39.01074 | 2.22010 | 110.54152 | 65.68740 | 0.00970 | 0.00753 | 0.80125 |
| 27036 | 47.10051 | −3.34717 | 133.29749 | 55.76482 | 0.01197 | 0.00660 | 0.80126 |
| 639 | 55.88946 | 7.32029 | 131.42825 | 68.80610 | 0.01088 | 0.00735 | 0.80133 |
| 79713 | 50.07337 | 1.98790 | 126.28917 | 62.72780 | 0.01034 | 0.00652 | 0.80162 |
| 2793 | 59.37622 | 1.23290 | 144.17486 | 54.80567 | 0.01027 | 0.00692 | 0.80550 |
| 203100 | 56.23784 | −0.66917 | 143.99437 | 56.62561 | 0.01087 | 0.00656 | 0.80765 |
| 1436 | 62.54781 | −4.46528 | 155.55190 | 56.26147 | 0.01225 | 0.00635 | 0.80899 |
| 219537 | 54.64096 | −0.17482 | 122.14836 | 62.05160 | 0.00935 | 0.00664 | 0.80979 |
| 3823 | 47.45547 | 6.76366 | 124.67866 | 73.40353 | 0.01012 | 0.00797 | 0.81017 |
| 4939 | 54.93668 | 2.34612 | 124.16029 | 62.90848 | 0.01034 | 0.00729 | 0.81044 |
| 140 | 62.63920 | −1.16922 | 136.74443 | 56.50799 | 0.01021 | 0.00654 | 0.81089 |
| 4867 | 35.87421 | 0.34243 | 111.42361 | 59.31244 | 0.00971 | 0.00679 | 0.81185 |
| 5920 | 57.16997 | 9.56822 | 129.77091 | 74.00633 | 0.01060 | 0.00772 | 0.81259 |
| 6171 | 6.19726 | −3.95861 | 76.13618 | 60.33724 | 0.00776 | 0.00704 | 0.81259 |
| 84290 | 18.87466 | 9.12580 | 88.23989 | 75.86612 | 0.00883 | 0.00804 | 0.81332 |
| 3437 | 52.43637 | 3.24532 | 117.32633 | 64.53447 | 0.00999 | 0.00715 | 0.81524 |
| 7903 | 65.35338 | −2.55649 | 145.76332 | 60.50851 | 0.01131 | 0.00663 | 0.81592 |

TABLE 2-continued

| | | | | | | | |
|---|---|---|---|---|---|---|---|
| 155038 | 63.76326 | 1.65517 | 152.51841 | 63.21803 | 0.01153 | 0.00691 | 0.81647 |
| 26071 | −5.74124 | 3.63743 | 64.25481 | 70.17830 | 0.00688 | 0.00751 | 0.81649 |
| 6519 | 30.74723 | 4.38991 | 106.84782 | 62.27222 | 0.01091 | 0.00800 | 0.81659 |
| 152559 | −1.44138 | −0.43929 | 70.43237 | 68.41128 | 0.00790 | 0.00777 | 0.81694 |
| 940 | 64.97114 | 2.67748 | 150.48590 | 65.44691 | 0.01187 | 0.00673 | 0.81714 |
| 85479 | 49.31461 | 1.76395 | 133.08913 | 66.94601 | 0.01068 | 0.00746 | 0.81765 |
| 5727 | 36.89524 | 7.65485 | 117.30419 | 74.16238 | 0.00995 | 0.00852 | 0.81773 |
| 126364 | 58.11260 | −7.45389 | 147.36881 | 54.44648 | 0.01132 | 0.00608 | 0.81789 |
| 968 | 57.84426 | −2.67166 | 150.69366 | 54.95064 | 0.01069 | 0.00677 | 0.81846 |
| 80774 | 46.06496 | 9.94201 | 117.54467 | 69.54511 | 0.01012 | 0.00727 | 0.81860 |
| 3960 | 7.98020 | −0.74566 | 65.98992 | 64.60424 | 0.00851 | 0.00802 | 0.81865 |
| 4318 | 58.39929 | 5.80813 | 136.93020 | 62.92695 | 0.01043 | 0.00708 | 0.81941 |
| 4050 | 53.38745 | 3.17434 | 138.95153 | 56.19906 | 0.01125 | 0.00739 | 0.81942 |
| 2342 | 12.28136 | 4.23959 | 79.10357 | 62.84488 | 0.00765 | 0.00706 | 0.81965 |
| 597 | 48.05879 | 4.58031 | 118.39267 | 67.15359 | 0.00985 | 0.00751 | 0.82021 |
| 23547 | 62.16419 | −3.34769 | 141.04547 | 60.50778 | 0.01092 | 0.00700 | 0.82061 |
| 27071 | 54.34650 | 7.74891 | 128.60774 | 65.00592 | 0.01048 | 0.00720 | 0.82072 |
| 6789 | 50.57443 | 7.55461 | 121.39711 | 70.49460 | 0.01084 | 0.00806 | 0.82136 |
| 11184 | 45.96366 | 6.32221 | 124.95374 | 65.74082 | 0.01032 | 0.00747 | 0.82191 |
| 10110 | 38.39073 | 0.29446 | 118.49405 | 59.80849 | 0.01029 | 0.00737 | 0.82224 |
| 286336 | 58.05907 | −3.02701 | 145.83192 | 59.29360 | 0.01098 | 0.00753 | 0.82313 |
| 969 | 55.98939 | −3.90915 | 126.41968 | 55.45782 | 0.00983 | 0.00629 | 0.82344 |
| 79825 | 47.58007 | 5.72279 | 120.75714 | 68.13441 | 0.00940 | 0.00799 | 0.82472 |
| 3600 | 53.88127 | 4.53756 | 130.34766 | 70.15040 | 0.01010 | 0.00784 | 0.82481 |
| 10800 | 58.76235 | 2.52583 | 143.30702 | 64.85583 | 0.01029 | 0.00702 | 0.82493 |
| 27233 | 36.13347 | −2.71233 | 108.52696 | 58.08836 | 0.00956 | 0.00654 | 0.82497 |
| 3824 | 46.44886 | 9.76558 | 134.29179 | 67.78766 | 0.01165 | 0.00846 | 0.82510 |
| 154 | 51.27713 | 9.40383 | 124.50888 | 71.41633 | 0.01070 | 0.00768 | 0.82537 |
| 7133 | 46.43729 | 6.06602 | 127.71199 | 67.68378 | 0.01078 | 0.00722 | 0.82574 |
| 5046 | 46.36774 | 4.00919 | 113.38597 | 68.54663 | 0.00856 | 0.00709 | 0.82784 |
| 114769 | 52.13986 | 0.23648 | 131.23671 | 68.77287 | 0.01116 | 0.00729 | 0.82817 |
| 8676 | 36.41949 | 3.28973 | 130.56420 | 50.06633 | 0.01085 | 0.00794 | 0.82834 |
| 3055 | 55.13288 | 0.23757 | 154.67101 | 54.67495 | 0.01287 | 0.00703 | 0.82852 |
| 7474 | 32.24400 | 2.88838 | 102.68396 | 67.65519 | 0.00900 | 0.00687 | 0.82888 |
| 2908 | 43.60186 | −5.22815 | 127.47082 | 60.57820 | 0.01088 | 0.00721 | 0.82898 |
| 4210 | 32.10912 | 6.84879 | 109.84383 | 71.15662 | 0.01014 | 0.00867 | 0.82921 |
| 9332 | 61.08714 | −1.01821 | 153.05685 | 61.38332 | 0.01164 | 0.00715 | 0.82935 |
| 11009 | 58.30112 | 6.67258 | 131.85307 | 67.46419 | 0.01020 | 0.00697 | 0.82936 |
| 6793 | 46.89513 | 5.51269 | 121.84925 | 70.27754 | 0.01106 | 0.00828 | 0.82970 |
| 5079 | 48.67362 | −1.40113 | 124.09206 | 68.13831 | 0.01086 | 0.00755 | 0.83073 |
| 3120 | 53.11646 | −1.98562 | 142.44735 | 59.89207 | 0.01132 | 0.00672 | 0.83082 |
| 26051 | 55.01586 | 2.73947 | 133.51655 | 68.86814 | 0.01127 | 0.00725 | 0.83094 |
| 1731 | 55.64025 | −0.68619 | 140.53684 | 61.17675 | 0.01128 | 0.00679 | 0.83113 |
| 7226 | 47.85360 | −0.56814 | 123.43311 | 62.83765 | 0.00966 | 0.00683 | 0.83157 |
| 2264 | 43.93821 | 3.36429 | 112.79335 | 66.23167 | 0.00938 | 0.00731 | 0.83189 |
| 9935 | 48.46257 | 5.82780 | 122.43335 | 67.87585 | 0.01046 | 0.00705 | 0.83189 |
| 137209 | 5.92955 | 1.98041 | 72.19498 | 64.09589 | 0.00758 | 0.00687 | 0.83361 |
| 5579 | 61.80780 | 0.61779 | 150.40975 | 60.73572 | 0.01245 | 0.00841 | 0.83392 |
| 91409 | 43.24937 | −3.13761 | 115.62948 | 61.95984 | 0.00961 | 0.00700 | 0.83465 |
| 348 | 55.32599 | −1.81077 | 139.45621 | 63.39835 | 0.01071 | 0.00662 | 0.83503 |
| 10797 | 41.10924 | 6.17891 | 104.45751 | 71.96586 | 0.00885 | 0.00785 | 0.83523 |
| 83666 | 55.05599 | 9.19356 | 127.69576 | 68.74883 | 0.01068 | 0.00738 | 0.83532 |
| 341640 | 43.46687 | 9.18667 | 116.16729 | 72.09336 | 0.01060 | 0.00773 | 0.83575 |
| 55220 | 40.26630 | 1.65430 | 110.46335 | 69.73718 | 0.00881 | 0.00698 | 0.83587 |
| 50943 | 41.95693 | 2.40431 | 125.59467 | 60.90867 | 0.01030 | 0.00795 | 0.83602 |
| 84957 | 34.77743 | 3.67619 | 108.38839 | 67.11210 | 0.00978 | 0.00751 | 0.83611 |
| 54518 | 49.79572 | −0.51884 | 149.41923 | 51.08921 | 0.01159 | 0.00762 | 0.83697 |
| 9047 | 39.44417 | −0.79531 | 119.87172 | 60.22297 | 0.00973 | 0.00722 | 0.83703 |
| 25805 | 46.90848 | 7.66370 | 119.01414 | 67.67187 | 0.01026 | 0.00670 | 0.83778 |
| 80301 | 50.00635 | −1.21913 | 124.85427 | 62.56289 | 0.01020 | 0.00722 | 0.83836 |
| 196403 | 31.83717 | 3.46940 | 101.46817 | 69.72132 | 0.00967 | 0.00808 | 0.83838 |
| 11309 | 60.29427 | 4.01881 | 145.44522 | 62.99419 | 0.01151 | 0.00714 | 0.83844 |
| 5768 | 26.85720 | 7.94965 | 103.23774 | 65.04000 | 0.01033 | 0.00863 | 0.83854 |
| 84689 | 47.60070 | −0.34561 | 129.38347 | 62.87637 | 0.01050 | 0.00657 | 0.83860 |
| 8330 | 12.34486 | 5.52676 | 76.73445 | 70.75327 | 0.00776 | 0.00774 | 0.83883 |
| 57047 | 3.24328 | 6.58658 | 71.51197 | 71.81900 | 0.00776 | 0.00743 | 0.84023 |
| 4542 | 46.28018 | 7.46991 | 125.75081 | 71.09173 | 0.01128 | 0.00784 | 0.84092 |
| 83605 | 42.18748 | 5.24599 | 117.43789 | 74.49219 | 0.00998 | 0.00821 | 0.84096 |
| 58189 | 34.80158 | 6.74555 | 109.37307 | 72.59243 | 0.01025 | 0.00803 | 0.84177 |

| entrez | mean rsq | Gene symbol | Threshold | Threshold genes | Specific genes |
|---|---|---|---|---|---|
| 10663 | 0.26573 | CXCR6 | Significant | CXCR6 | Theta specific |
| 285175 | 0.17542 | UNC80 | Significant | UNC80 | Theta specific |
| 2395 | −0.07065 | FXN | Significant | FXN | Theta specific |
| 54470 | −0.08968 | ARMCX6 | Significant | ARMCX6 | Theta specific |
| 2191 | 0.22382 | FAP | Significant | FAP | Theta specific |
| 80709 | 0.23515 | AKNA | Significant | AKNA | Theta specific |
| 9830 | 0.13366 | TRIM14 | Significant | TRIM14 | Theta specific |

TABLE 2-continued

| | | | | | |
|---|---|---|---|---|---|
| 64761 | 0.18101 | PARP12 | Significant | PARP12 | Theta specific |
| 54809 | 0.19207 | SAMD9 | Significant | SAMD9 | Theta specific |
| 3822 | 0.19304 | KLRC2 | Significant | KLRC2 | Theta specific |
| 57643 | 0.05978 | ZSWIM5 | Significant | ZSWIM5 | Theta specific |
| 943 | 0.06788 | TNFRSF8 | Significant | TNFRSF8 | Theta specific |
| 347731 | 0.17550 | LRRTM3 | Significant | LRRTM3 | Theta specific |
| 53829 | 0.17823 | P2RY13 | Significant | P2RY13 | Theta specific |
| 474354 | 0.22337 | LRRC18 | Significant | LRRC18 | Theta specific |
| 3601 | 0.20126 | IL15RA | Significant | IL15RA | Theta specific |
| 55589 | 0.19935 | BMP2K | Significant | BMP2K | Theta specific |
| 3718 | 0.19433 | JAK3 | Significant | JAK3 | Theta specific |
| 57333 | −0.02406 | RCN3 | Significant | RCN3 | Theta specific |
| 64127 | 0.20240 | NOD2 | Significant | NOD2 | Theta specific |
| 54578 | 0.09398 | UGT1A6 | Significant | UGT1A6 | Theta specific |
| 8737 | 0.09020 | RIPK1 | Significant | RIPK1 | Theta specific |
| 6999 | 0.16063 | TDO2 | Significant | TDO2 | Theta specific |
| 51816 | 0.18588 | CECR1 | Significant | CECR1 | Theta specific |
| 460 | 0.13313 | ASTN1 | Significant | ASTN1 | Theta specific |
| 152789 | 0.12013 | JAKMIP1 | Significant | JAKMIP1 | Theta specific |
| 116986 | 0.18166 | AGAP2 | Significant | AGAP2 | Theta specific |
| 3112 | 0.17082 | HLA-DOB | Significant | HLA-DOB | Theta specific |
| 8643 | 0.07795 | PTCH2 | Significant | PTCH2 | Theta specific |
| 5699 | 0.18712 | PSMB10 | Significant | PSMB10 | Theta specific |
| 55840 | 0.19230 | EAF2 | Significant | EAF2 | Theta specific |
| 10154 | 0.14815 | PLXNC1 | Significant | PLXNC1 | Theta specific |
| 196740 | 0.12238 | VSTM4 | Significant | VSTM4 | Theta specific |
| 219654 | 0.03644 | ZCCHC24 | Significant | ZCCHC24 | Theta specific |
| 6892 | 0.19602 | TAPBP | Significant | TAPBP | Theta specific |
| 347736 | 0.00899 | NME9 | Significant | NME9 | Theta specific |
| 197358 | 0.17476 | NLRC3 | Significant | NLRC3 | Theta specific |
| 1945 | 0.15824 | EFNA4 | Significant | EFNA4 | Theta specific |
| 146562 | 0.02108 | C16orf71 | Significant | C16orf71 | Theta specific |
| 4599 | 0.09123 | MX1 | Significant | MX1 | Theta specific |
| 54579 | 0.07628 | UGT1A5 | Significant | UGT1A5 | Theta specific |
| 151636 | 0.16048 | DTX3L | Significant | DTX3L | Theta specific |
| 1236 | 0.14549 | CCR7 | Significant | CCR7 | Theta specific |
| 64780 | 0.13836 | MICAL1 | Significant | MICAL1 | Theta specific |
| 652 | 0.08080 | BMP4 | Significant | BMP4 | Theta specific |
| 221188 | 0.18961 | ADGRG5 | Significant | ADGRG5 | Theta specific |
| 80863 | 0.11736 | PRRT1 | Significant | PRRT1 | Theta specific |
| 54659 | 0.06949 | UGT1A3 | Significant | UGT1A3 | Theta specific |
| 3385 | 0.16898 | ICAM3 | Significant | ICAM3 | Theta specific |
| 8671 | 0.09671 | SLC4A4 | Significant | SLC4A4 | Theta specific |
| 80790 | 0.06852 | CMIP | Significant | CMIP | Theta specific |
| 282991 | −0.08073 | BLOC1S2 | Significant | BLOC1S2 | Theta specific |
| 3624 | 0.14807 | INHBA | Significant | INHBA | Theta specific |
| 8875 | 0.16719 | VNN2 | Significant | VNN2 | Theta specific |
| 9267 | 0.11038 | CYTH1 | Significant | CYTH1 | Theta specific |
| 50863 | 0.13345 | NTM | Significant | NTM | Theta specific |
| 925 | 0.72703 | CD8A | Significant | CD8A | R Theta common |
| 916 | 0.72216 | CD3E | Significant | CD3E | R Theta common |
| 914 | 0.70376 | CD2 | Significant | CD2 | R Theta common |
| 915 | 0.67183 | CD3D | Significant | CD3D | R Theta common |
| 149628 | 0.63963 | PYHIN1 | Significant | PYHIN1 | R Theta common |
| 3702 | 0.62547 | ITK | Significant | ITK | R Theta common |
| 10225 | 0.63018 | CD96 | Significant | CD96 | R Theta common |
| 387357 | 0.64464 | THEMIS | Significant | THEMIS | R Theta common |
| 114836 | 0.63036 | SLAMF6 | Significant | SLAMF6 | R Theta common |
| 50852 | 0.59883 | TRAT1 | Significant | TRAT1 | R Theta common |
| 84636 | 0.62531 | GPR174 | Significant | GPR174 | R Theta common |
| 962 | 0.62257 | CD48 | Significant | CD48 | R Theta common |
| 57823 | 0.60983 | SLAMF7 | Significant | SLAMF7 | R Theta common |
| 4283 | 0.58280 | CXCL9 | Significant | CXCL9 | R Theta common |
| 29851 | 0.58114 | ICOS | Significant | ICOS | R Theta common |
| 128611 | 0.54696 | ZNF831 | Significant | ZNF831 | R Theta common |
| 3683 | 0.59279 | ITGAL | Significant | ITGAL | R Theta common |
| 10320 | 0.58566 | IKZF1 | Significant | IKZF1 | R Theta common |
| 6504 | 0.57798 | SLAMF1 | Significant | SLAMF1 | R Theta common |
| 645432 | 0.54292 | ARRDC5 | Significant | ARRDC5 | R Theta common |
| 80342 | 0.56828 | TRAF3IP3 | Significant | TRAF3IP3 | R Theta common |
| 9402 | 0.55816 | GRAP2 | Significant | GRAP2 | R Theta common |
| 919 | 0.55485 | CD247 | Significant | CD247 | R Theta common |
| 3003 | 0.56186 | GZMK | Significant | GZMK | R Theta common |
| 51411 | 0.57120 | BIN2 | Significant | BIN2 | R Theta common |
| 5551 | 0.53721 | PRF1 | Significant | PRF1 | R Theta common |
| 4063 | 0.53248 | LY9 | Significant | LY9 | R Theta common |
| 100506736 | 0.57160 | SLFN12L | Significant | SLFN12L | R Theta common |
| 3587 | 0.56227 | IL10RA | Significant | IL10RA | R Theta common |
| 27334 | 0.53452 | P2RY10 | Significant | P2RY10 | R Theta common |
| 165631 | 0.54535 | PARP15 | Significant | PARP15 | R Theta common |

TABLE 2-continued

| | | | | | |
|---|---|---|---|---|---|
| 1794 | 0.55875 | DOCK2 | Significant | DOCK2 | R Theta common |
| 53347 | 0.54709 | UBASH3A | Significant | UBASH3A | R Theta common |
| 115362 | 0.54424 | GBP5 | Significant | GBP5 | R Theta common |
| 917 | 0.52547 | CD3G | Significant | CD3G | R Theta common |
| 1493 | 0.53795 | CTLA4 | Significant | CTLA4 | R Theta common |
| 64926 | 0.55040 | RASAL3 | Significant | RASAL3 | R Theta common |
| 4068 | 0.54066 | SH2D1A | Significant | SH2D1A | R Theta common |
| 30009 | 0.49010 | TBX21 | Significant | TBX21 | R Theta common |
| 7535 | 0.51936 | ZAP70 | Significant | ZAP70 | R Theta common |
| 3560 | 0.52032 | IL2RB | Significant | IL2RB | R Theta common |
| 5294 | 0.52620 | PIK3CG | Significant | PIK3CG | R Theta common |
| 2633 | 0.47849 | GBP1 | Significant | GBP1 | R Theta common |
| 64333 | 0.49019 | ARHGAP9 | Significant | ARHGAP9 | R Theta common |
| 55843 | 0.49896 | ARHGAP15 | Significant | ARHGAP15 | R Theta common |
| 952 | 0.50352 | CD38 | Significant | CD38 | R Theta common |
| 11262 | 0.52392 | SP140 | Significant | SP140 | R Theta common |
| 695 | 0.50613 | BTK | Significant | BTK | R Theta common |
| 3561 | 0.49311 | IL2RG | Significant | IL2RG | R Theta common |
| 101929889 | 0.51432 | | Significant | | R Theta common |
| 6693 | 0.51432 | SPN | Significant | SPN | R Theta common |
| 117289 | 0.48817 | TAGAP | Significant | TAGAP | R Theta common |
| 10563 | 0.47252 | CXCL13 | Significant | CXCL13 | R Theta common |
| 8302 | 0.48703 | KLRC4 | Significant | KLRC4 | R Theta common |
| 80008 | 0.49030 | TMEM156 | Significant | TMEM156 | R Theta common |
| 115352 | 0.46794 | FCRL3 | Significant | FCRL3 | R Theta common |
| 147138 | 0.50808 | TMC8 | Significant | TMC8 | R Theta common |
| 356 | 0.47992 | FASLG | Significant | FASLG | R Theta common |
| 26191 | 0.49722 | PTPN22 | Significant | PTPN22 | R Theta common |
| 3575 | 0.47169 | IL7R | Significant | IL7R | R Theta common |
| 4046 | 0.43619 | LSP1 | Significant | LSP1 | R Theta common |
| 1536 | 0.50379 | CYBB | Significant | CYBB | R Theta common |
| 6352 | 0.47449 | CCL5 | Significant | CCL5 | R Theta common |
| 8832 | 0.48847 | CD84 | Significant | CD84 | R Theta common |
| 3662 | 0.45705 | IRF4 | Significant | IRF4 | R Theta common |
| 3627 | 0.43211 | CXCL10 | Significant | CXCL10 | R Theta common |
| 64092 | 0.44722 | SAMSN1 | Significant | SAMSN1 | R Theta common |
| 3458 | 0.47492 | IFNG | Significant | IFNG | R Theta common |
| 9404 | 0.47885 | LPXN | Significant | LPXN | R Theta common |
| 729230 | 0.49208 | CCR2 | Significant | CCR2 | R Theta common |
| 1233 | 0.41597 | CCR4 | Significant | CCR4 | R Theta common |
| 79931 | 0.43199 | TNIP3 | Significant | TNIP3 | R Theta common |
| 115361 | 0.42090 | GBP4 | Significant | GBP4 | R Theta common |
| 4332 | 0.40797 | MNDA | Significant | MNDA | R Theta common |
| 923 | 0.41203 | CD6 | Significant | CD6 | R Theta common |
| 4064 | 0.42577 | CD180 | Significant | CD180 | R Theta common |
| 10673 | 0.44497 | TNFSF13B | Significant | TNFSF13B | R Theta common |
| 3134 | 0.40570 | HLA-F | Significant | HLA-F | R Theta common |
| 313 | 0.45148 | AOAH | Significant | AOAH | R Theta common |
| 51056 | 0.39574 | LAP3 | Significant | LAP3 | R Theta common |
| 80833 | 0.43238 | APOL3 | Significant | APOL3 | R Theta common |
| 100528032 | 0.45359 | KLRK1 | Significant | KLRK1 | R Theta common |
| 22914 | 0.45359 | KLRK1 | Significant | KLRK1 | R Theta common |
| 199 | 0.40100 | AIF1 | Significant | AIF1 | R Theta common |
| 29126 | 0.39122 | CD274 | Significant | CD274 | R Theta common |
| 225 | 0.41974 | ABCD2 | Significant | ABCD2 | R Theta common |
| 5778 | 0.42754 | PTPN7 | Significant | PTPN7 | R Theta common |
| 567 | 0.42903 | B2M | Significant | B2M | R Theta common |
| 6775 | 0.43781 | STAT4 | Significant | STAT4 | R Theta common |
| 4818 | 0.41174 | NKG7 | Significant | NKG7 | R Theta common |
| 2207 | 0.41841 | FCER1G | Significant | FCER1G | R Theta common |
| 3604 | 0.38691 | TNFRSF9 | Significant | TNFRSF9 | R Theta common |
| 3682 | 0.38635 | ITGAE | Significant | ITGAE | R Theta common |
| 6890 | 0.39653 | TAP1 | Significant | TAP1 | R Theta common |
| 55340 | 0.42917 | GIMAP5 | Significant | GIMAP5 | R Theta common |
| 10666 | 0.41253 | CD226 | Significant | CD226 | R Theta common |
| 64581 | 0.37354 | CLEC7A | Significant | CLEC7A | R Theta common |
| 5698 | 0.38139 | PSMB9 | Significant | PSMB9 | R Theta common |
| 6373 | 0.37553 | CXCL11 | Significant | CXCL11 | R Theta common |
| 441168 | 0.38751 | FAM26F | Significant | FAM26F | R Theta common |
| 100423062 | 0.39155 | IGLL5 | Significant | IGLL5 | R Theta common |
| 1071 | 0.38363 | CETP | Significant | CETP | R Theta common |
| 100527949 | 0.42008 | GIMAP1-GIMAP5 | Significant | GIMAP1-GIMAP5 | R Theta common |
| 3659 | 0.37314 | IRF1 | Significant | IRF1 | R Theta common |
| 154075 | 0.41047 | SAMD3 | Significant | SAMD3 | R Theta common |
| 653361 | 0.35917 | NCF1 | Significant | NCF1 | R Theta common |
| 92241 | 0.37665 | RCSD1 | Significant | RCSD1 | R Theta common |
| 834 | 0.36929 | CASP1 | Significant | CASP1 | R Theta common |
| 57705 | 0.38581 | WDFY4 | Significant | WDFY4 | R Theta common |
| 81030 | 0.35414 | ZBP1 | Significant | ZBP1 | R Theta common |

TABLE 2-continued

| | | | | | |
|---|---|---|---|---|---|
| 5026 | 0.34617 | P2RX5 | Significant | P2RX5 | R Theta common |
| 9046 | 0.37700 | DOK2 | Significant | DOK2 | R Theta common |
| 55911 | 0.32426 | APOBR | Significant | APOBR | R Theta common |
| 102725018 | 0.35744 | | Significant | | R Theta common |
| 973 | 0.37838 | CD79A | Significant | CD79A | R Theta common |
| 219285 | 0.33726 | SAMD9L | Significant | SAMD9L | R Theta common |
| 5133 | 0.31564 | PDCD1 | Significant | PDCD1 | R Theta common |
| 89790 | 0.35745 | SIGLEC10 | Significant | SIGLEC10 | R Theta common |
| 27240 | 0.35944 | SIT1 | Significant | SIT1 | R Theta common |
| 27299 | 0.36100 | ADAMDEC1 | Significant | ADAMDEC1 | R Theta common |
| 9051 | 0.38413 | PSTPIP1 | Significant | PSTPIP1 | R Theta common |
| 3738 | 0.36690 | KCNA3 | Significant | KCNA3 | R Theta common |
| 89857 | 0.36556 | KLHL6 | Significant | KLHL6 | R Theta common |
| 51744 | 0.29397 | CD244 | Significant | CD244 | R Theta common |
| 10538 | 0.35066 | BATF | Significant | BATF | R Theta common |
| 27128 | 0.34925 | CYTH4 | Significant | CYTH4 | R Theta common |
| 80830 | 0.36324 | APOL6 | Significant | APOL6 | R Theta common |
| 146722 | 0.33326 | CD300LF | Significant | CD300LF | R Theta common |
| 340152 | 0.33937 | ZC3H12D | Significant | ZC3H12D | R Theta common |
| 120425 | 0.34577 | AMICA1 | Significant | AMICA1 | R Theta common |
| 221472 | 0.35387 | FGD2 | Significant | FGD2 | R Theta common |
| 8807 | 0.32981 | IL18RAP | Significant | IL18RAP | R Theta common |
| 3512 | 0.36173 | JCHAIN | Significant | JCHAIN | R Theta common |
| 5790 | 0.28832 | PTPRCAP | Significant | PTPRCAP | R Theta common |
| 3603 | 0.30912 | IL16 | Significant | IL16 | R Theta common |
| 6891 | 0.30412 | TAP2 | Significant | TAP2 | R Theta common |
| 9744 | 0.34877 | ACAP1 | Significant | ACAP1 | R Theta common |
| 197135 | 0.33410 | PATL2 | Significant | PATL2 | R Theta common |
| 6772 | 0.29344 | STAT1 | Significant | STAT1 | R Theta common |
| 51513 | 0.30968 | ETV7 | Significant | ETV7 | R Theta common |
| 1520 | 0.37236 | CTSS | Significant | CTSS | R Theta common |
| 9214 | 0.34237 | FCMR | Significant | FCMR | R Theta common |
| 54625 | 0.30961 | PARP14 | Significant | PARP14 | R Theta common |
| 2634 | 0.29579 | GBP2 | Significant | GBP2 | R Theta common |
| 26279 | 0.32789 | PLA2G2D | Significant | PLA2G2D | R Theta common |
| 489 | 0.28481 | ATP2A3 | Significant | ATP2A3 | R Theta common |
| 341 | 0.31777 | APOC1 | Significant | APOC1 | R Theta common |
| 1318 | 0.28536 | SLC31A2 | Significant | SLC31A2 | R Theta common |
| 926 | 0.29477 | CD8B | Significant | CD8B | R Theta common |
| 64135 | 0.23486 | IFIH1 | Significant | IFIH1 | R Theta common |
| 5552 | 0.28895 | SRGN | Significant | SRGN | R Theta common |
| 5293 | 0.28535 | PIK3CD | Significant | PIK3CD | R Theta common |
| 25816 | 0.29437 | TNFAIP8 | Significant | TNFAIP8 | R Theta common |
| 9056 | 0.25745 | SLC7A7 | Significant | SLC7A7 | R Theta common |
| 116449 | 0.30964 | CLNK | Significant | CLNK | R Theta common |
| 50856 | 0.23549 | CLEC4A | Significant | CLEC4A | R Theta common |
| 7185 | 0.25236 | TRAF1 | Significant | TRAF1 | R Theta common |
| 5696 | 0.29834 | PSMB8 | Significant | PSMB8 | R Theta common |
| 3117 | 0.28360 | HLA-DQA1 | Significant | HLA-DQA1 | R Theta common |
| 51237 | 0.30932 | MZB1 | Significant | MZB1 | R Theta common |
| 79368 | 0.27728 | FCRL2 | Significant | FCRL2 | R Theta common |
| 25780 | 0.25821 | RASGRP3 | Significant | RASGRP3 | R Theta common |
| 51296 | 0.24343 | SLC15A3 | Significant | SLC15A3 | R Theta common |
| 100509457 | 0.27053 | | Significant | | R Theta common |
| 2643 | 0.27824 | GCH1 | Significant | GCH1 | R Theta common |
| 83937 | 0.28787 | RASSF4 | Significant | RASSF4 | R Theta common |
| 150372 | 0.23262 | NFAM1 | Significant | NFAM1 | R Theta common |
| 23526 | 0.27879 | HMHA1 | Significant | HMHA1 | R Theta common |
| 6916 | 0.30687 | TBXAS1 | Significant | TBXAS1 | R Theta common |
| 3123 | 0.27992 | HLA-DRB1 | Significant | HLA-DRB1 | R Theta common |
| 102723407 | 0.24087 | | Significant | | R Theta common |
| 25939 | 0.27751 | SAMHD1 | Significant | SAMHD1 | R Theta common |
| 1806 | 0.25641 | DPYD | Significant | DPYD | R Theta common |
| 160365 | 0.22262 | CLECL1 | Significant | CLECL1 | R Theta common |
| 3635 | 0.29644 | INPP5D | Significant | INPP5D | R Theta common |
| 2124 | 0.23735 | EVI2B | Significant | EVI2B | R Theta common |
| 3431 | 0.20715 | | Significant | | R Theta common |
| 9111 | 0.19265 | NMI | Significant | NMI | R Theta common |
| 4261 | 0.23730 | CIITA | Significant | CIITA | R Theta common |
| 3108 | 0.24481 | HLA-DMA | Significant | HLA-DMA | R Theta common |
| 10791 | 0.23626 | VAMP5 | Significant | VAMP5 | R Theta common |
| 5734 | 0.22256 | PTGER4 | Significant | PTGER4 | R Theta common |
| 57713 | 0.20990 | SFMBT2 | Significant | SFMBT2 | R Theta common |
| 11118 | 0.23138 | BTN3A2 | Significant | BTN3A2 | R Theta common |
| 5027 | 0.22812 | P2RX7 | Significant | P2RX7 | R Theta common |
| 3105 | 0.21982 | HLA-A | Significant | HLA-A | R Theta common |
| 2014 | 0.19211 | EMP3 | Significant | EMP3 | R Theta common |
| 26157 | 0.23821 | GIMAP2 | Significant | GIMAP2 | R Theta common |
| 11119 | 0.20300 | BTN3A1 | Significant | BTN3A1 | R Theta common |
| 55016 | 0.21408 | MARCH1 | Significant | MARCH1 | R Theta common |

TABLE 2-continued

| | | | | | |
|---|---|---|---|---|---|
| 10384 | 0.19773 | BTN3A3 | Significant | BTN3A3 | R Theta common |
| 118788 | 0.22211 | PIK3AP1 | Significant | PIK3AP1 | R Theta common |
| 2313 | 0.23244 | FLI1 | Significant | FLI1 | R Theta common |
| 1234 | 0.64682 | CCR5 | Significant | CCR5 | R specific |
| 55423 | 0.58067 | SIRPG | Significant | SIRPG | R specific |
| 50615 | 0.54656 | IL21R | Significant | IL21R | R specific |
| 257101 | 0.51317 | ZNF683 | Significant | ZNF683 | R specific |
| 963 | 0.51273 | CD53 | Significant | CD53 | R specific |
| 2999 | 0.51931 | GZMH | Significant | GZMH | R specific |
| 5788 | 0.50614 | PTPRC | Significant | PTPRC | R specific |
| 3937 | 0.48940 | LCP2 | Significant | LCP2 | R specific |
| 399 | 0.45076 | RHOH | Significant | RHOH | R specific |
| 56833 | 0.49765 | SLAMF8 | Significant | SLAMF8 | R specific |
| 2359 | 0.50129 | FPR3 | Significant | FPR3 | R specific |
| 84868 | 0.50083 | HAVCR2 | Significant | HAVCR2 | R specific |
| 201633 | 0.45374 | TIGIT | Significant | TIGIT | R specific |
| 168537 | 0.45492 | GIMAP7 | Significant | GIMAP7 | R specific |
| 22797 | 0.48216 | TFEC | Significant | TFEC | R specific |
| 942 | 0.43031 | CD86 | Significant | CD86 | R specific |
| 2533 | 0.46313 | FYB | Significant | FYB | R specific |
| 3071 | 0.48605 | NCKAP1L | Significant | NCKAP1L | R specific |
| 3932 | 0.46936 | LCK | Significant | LCK | R specific |
| 128346 | 0.41895 | C1orf162 | Significant | C1orf162 | R specific |
| 54900 | 0.47099 | LAX1 | Significant | LAX1 | R specific |
| 55303 | 0.48279 | GIMAP4 | Significant | GIMAP4 | R specific |
| 8477 | 0.46453 | GPR65 | Significant | GPR65 | R specific |
| 54440 | 0.46556 | SASH3 | Significant | SASH3 | R specific |
| 84174 | 0.41774 | SLA2 | Significant | SLA2 | R specific |
| 920 | 0.41967 | CD4 | Significant | CD4 | R specific |
| 5341 | 0.44281 | PLEK | Significant | PLEK | R specific |
| 1043 | 0.45353 | CD52 | Significant | CD52 | R specific |
| 445347 | 0.41926 | TRGC1 | Significant | TRGC1 | R specific |
| 64005 | 0.45197 | MYO1G | Significant | MYO1G | R specific |
| 3676 | 0.43522 | ITGA4 | Significant | ITGA4 | R specific |
| 8320 | 0.45734 | EOMES | Significant | EOMES | R specific |
| 3903 | 0.45943 | LAIR1 | Significant | LAIR1 | R specific |
| 941 | 0.41578 | CD80 | Significant | CD80 | R specific |
| 7805 | 0.43393 | LAPTM5 | Significant | LAPTM5 | R specific |
| 256380 | 0.39560 | SCML4 | Significant | SCML4 | R specific |
| 3001 | 0.39954 | GZMA | Significant | GZMA | R specific |
| 1521 | 0.36348 | CTSW | Significant | CTSW | R specific |
| 9447 | 0.35714 | AIM2 | Significant | AIM2 | R specific |
| 9535 | 0.38403 | GMFG | Significant | GMFG | R specific |
| 3594 | 0.41421 | IL12RB1 | Significant | IL12RB1 | R specific |
| 3002 | 0.39342 | GZMB | Significant | GZMB | R specific |
| 11151 | 0.38228 | CORO1A | Significant | CORO1A | R specific |
| 257106 | 0.38653 | ARHGAP30 | Significant | ARHGAP30 | R specific |
| 713 | 0.39460 | C1QB | Significant | C1QB | R specific |
| 7305 | 0.39381 | TYROBP | Significant | TYROBP | R specific |
| 8530 | 0.35104 | CST7 | Significant | CST7 | R specific |
| 7940 | 0.35523 | LST1 | Significant | LST1 | R specific |
| 11006 | 0.40520 | LILRB4 | Significant | LILRB4 | R specific |
| 64231 | 0.39581 | MS4A6A | Significant | MS4A6A | R specific |
| 6404 | 0.37798 | SELPLG | Significant | SELPLG | R specific |
| 23533 | 0.35915 | PIK3R5 | Significant | PIK3R5 | R specific |
| 219972 | 0.38599 | MPEG1 | Significant | MPEG1 | R specific |
| 1439 | 0.37229 | CSF2RB | Significant | CSF2RB | R specific |
| 10859 | 0.35458 | LILRB1 | Significant | LILRB1 | R specific |
| 6688 | 0.37718 | SPI1 | Significant | SPI1 | R specific |
| 56253 | 0.31470 | CRTAM | Significant | CRTAM | R specific |
| 83706 | 0.36203 | FERMT3 | Significant | FERMT3 | R specific |
| 2672 | 0.36272 | GFI1 | Significant | GFI1 | R specific |
| 9840 | 0.37637 | TESPA1 | Significant | TESPA1 | R specific |
| 7456 | 0.35947 | WIPF1 | Significant | WIPF1 | R specific |
| 4069 | 0.33607 | LYZ | Significant | LYZ | R specific |
| 26228 | 0.37200 | STAP1 | Significant | STAP1 | R specific |
| 6503 | 0.36468 | SLA | Significant | SLA | R specific |
| 139716 | 0.40328 | GAB3 | Significant | GAB3 | R specific |
| 714 | 0.36164 | C1QC | Significant | C1QC | R specific |
| 80231 | 0.30893 | CXorf21 | Significant | CXorf21 | R specific |
| 241 | 0.31455 | ALOX5AP | Significant | ALOX5AP | R specific |
| 712 | 0.36127 | C1QA | Significant | C1QA | R specific |
| 51225 | 0.34396 | ABI3 | Significant | ABI3 | R specific |
| 3687 | 0.32179 | ITGAX | Significant | ITGAX | R specific |
| 83416 | 0.34022 | FCRL5 | Significant | FCRL5 | R specific |
| 931 | 0.32334 | MS4A1 | Significant | MS4A1 | R specific |
| 6351 | 0.30607 | CCL4 | Significant | CCL4 | R specific |
| 924 | 0.29869 | CD7 | Significant | CD7 | R specific |
| 5330 | 0.33144 | PLCB2 | Significant | PLCB2 | R specific |
| 80380 | 0.32086 | PDCD1LG2 | Significant | PDCD1LG2 | R specific |

TABLE 2-continued

| | | | | |
|---|---|---|---|---|
| 100293211 | 0.34321 | | Significant | R specific |
| 397 | 0.34035 | ARHGDIB | Significant ARHGDIB | R specific |
| 959 | 0.32248 | CD40LG | Significant CD40LG | R specific |
| 64919 | 0.29918 | BCL11B | Significant BCL11B | R specific |
| 10870 | 0.30432 | HOST | Significant HOST | R specific |
| 8514 | 0.30852 | KCNAB2 | Significant KCNAB2 | R specific |
| 4689 | 0.32776 | NCF4 | Significant NCF4 | R specific |
| 91526 | 0.27475 | ANKRD44 | Significant ANKRD44 | R specific |
| 2214 | 0.31691 | FCGR3A | Significant FCGR3A | R specific |
| 3684 | 0.31024 | ITGAM | Significant ITGAM | R specific |
| 84166 | 0.26629 | NLRC5 | Significant NLRC5 | R specific |
| 719 | 0.33047 | C3AR1 | Significant C3AR1 | R specific |
| 6402 | 0.27079 | SELL | Significant SELL | R specific |
| 219855 | 0.27398 | SLC37A2 | Significant SLC37A2 | R specific |
| 10333 | 0.30816 | TLR6 | Significant TLR6 | R specific |
| 6039 | 0.25131 | RNASE6 | Significant RNASE6 | R specific |
| 3689 | 0.31610 | ITGB2 | Significant ITGB2 | R specific |
| 4481 | 0.28816 | MSR1 | Significant MSR1 | R specific |
| 101060789 | 0.26379 | | Significant | R specific |
| 972 | 0.26480 | CD74 | Significant CD74 | R specific |
| 474344 | 0.29403 | GIMAP6 | Significant GIMAP6 | R specific |
| 80896 | 0.26079 | NPL | Significant NPL | R specific |
| 100049587 | 0.26207 | SIGLEC14 | Significant SIGLEC14 | R specific |
| 100131897 | 0.27929 | FAM196B | Significant FAM196B | R specific |
| 115350 | 0.25151 | FCRL1 | Significant FCRL1 | R specific |
| 5450 | 0.25209 | POU2AF1 | Significant POU2AF1 | R specific |
| 10288 | 0.25178 | LILRB3 | Significant LILRB3 | Not specific |
| 3394 | 0.27686 | IRF8 | Significant IRF8 | Not specific |
| 7454 | 0.19068 | WAS | Significant WAS | Not specific |
| 136647 | −0.12538 | MPLKIP | Significant MPLKIP | Not specific |
| 1230 | 0.27913 | CCR1 | Significant CCR1 | Not specific |
| 5880 | 0.31566 | RAC2 | Significant RAC2 | Not specific |
| 5996 | 0.26560 | RGS1 | Significant RGS1 | Not specific |
| 7462 | 0.21782 | LAT2 | Significant LAT2 | Not specific |
| 10578 | 0.19883 | GNLY | Significant GNLY | Not specific |
| 4688 | 0.26826 | NCF2 | Significant NCF2 | Not specific |
| 2213 | 0.27818 | FCGR2B | Significant FCGR2B | Not specific |
| 7634 | 0.21549 | ZNF80 | Significant ZNF80 | Not specific |
| 1908 | 0.22973 | EDN3 | Significant EDN3 | Not specific |
| 23495 | 0.26013 | TNFRSF13B | Significant TNFRSF13B | Not specific |
| 717 | 0.26771 | C2 | Significant C2 | Not specific |
| 158830 | 0.20776 | CXorf65 | Significant CXorf65 | Not specific |
| 100129083 | 0.25417 | | Significant | Not specific |
| 3936 | 0.26591 | LCP1 | Significant LCP1 | Not specific |
| 2212 | 0.26842 | FCGR2A | Significant FCGR2A | Not specific |
| 6356 | 0.19169 | CCL11 | Significant CCL11 | Not specific |
| 1240 | 0.27369 | CMKLR1 | Significant CMKLR1 | Not specific |
| 11040 | 0.26549 | PIM2 | Significant PIM2 | Not specific |
| 3821 | 0.18747 | KLRC1 | Significant KLRC1 | Not specific |
| 3858 | −0.16088 | KRT10 | Significant KRT10 | Not specific |
| 55013 | 0.22541 | CCDC109B | Significant CCDC109B | Not specific |
| 84541 | 0.15118 | KBTBD8 | Significant KBTBD8 | Not specific |
| 7727 | −0.07233 | ZNF174 | Significant ZNF174 | Not specific |
| 27180 | 0.20228 | SIGLEC9 | Significant SIGLEC9 | Not specific |
| 91543 | 0.17905 | RSAD2 | Significant RSAD2 | Not specific |
| 102724536 | 0.24740 | | Significant | Not specific |
| 22806 | 0.19890 | IKZF3 | Significant IKZF3 | Not specific |
| 4973 | 0.16101 | OLR1 | Significant OLR1 | Not specific |
| 10871 | 0.18872 | CD300C | Significant CD300C | Not specific |
| 8419 | 0.22887 | BFSP2 | Significant BFSP2 | Not specific |
| 971 | 0.20868 | CD72 | Significant CD72 | Not specific |
| 197259 | 0.25438 | MLKL | Significant MLKL | Not specific |
| 3559 | 0.23761 | IL2RA | Significant IL2RA | Not specific |
| 284759 | 0.17529 | SIRPB2 | Significant SIRPB2 | Not specific |
| 752 | 0.21868 | FMNL1 | Significant FMNL1 | Not specific |
| 55821 | 0.18683 | ALLC | Significant ALLC | Not specific |
| 94240 | 0.20786 | EPSTI1 | Significant EPSTI1 | Not specific |
| 11314 | 0.21964 | CD300A | Significant CD300A | Not specific |
| 115992 | 0.09593 | RNF166 | Significant RNF166 | Not specific |
| 3902 | 0.21733 | LAG3 | Significant LAG3 | Not specific |
| 2268 | 0.18496 | FGR | Significant FGR | Not specific |
| 50619 | 0.16705 | DEF6 | Significant DEF6 | Not specific |
| 9437 | 0.21029 | NCR1 | Significant NCR1 | Not specific |
| 124637 | −0.13146 | CYB5D1 | Significant CYB5D1 | Not specific |
| 23433 | −0.01643 | RHOQ | Significant RHOQ | Not specific |
| 2323 | 0.14279 | FLT3LG | Significant FLT3LG | Not specific |
| 5791 | 0.11377 | PTPRE | Significant PTPRE | Not specific |
| 4640 | −0.11075 | MYO1A | Significant MYO1A | Not specific |
| 81793 | 0.22793 | TLR10 | Significant TLR10 | Not specific |
| 3101 | 0.22203 | HK3 | Significant HK3 | Not specific |

TABLE 2-continued

| | | | | | |
|---|---|---|---|---|---|
| 338557 | 0.18450 | FFAR4 | Significant | FFAR4 | Not specific |
| 974 | 0.16758 | CD79B | Significant | CD79B | Not specific |
| 255231 | 0.14886 | MCOLN2 | Significant | MCOLN2 | Not specific |
| 129607 | 0.18463 | CMPK2 | Significant | CMPK2 | Not specific |
| 9034 | 0.18923 | CCRL2 | Significant | CCRL2 | Not specific |
| 7097 | 0.23671 | TLR2 | Significant | TLR2 | Not specific |
| 283234 | 0.18401 | CCDC88B | Significant | CCDC88B | Not specific |
| 170575 | 0.20643 | GIMAP1 | Significant | GIMAP1 | Not specific |
| 54491 | 0.16876 | FAM105A | Significant | FAM105A | Not specific |
| 388336 | −0.01044 | SHISA6 | Significant | SHISA6 | Not specific |
| 58475 | 0.22101 | MS4A7 | Significant | MS4A7 | Not specific |
| 10437 | 0.19455 | IFI30 | Significant | IFI30 | Not specific |
| 945 | 0.21730 | CD33 | Significant | CD33 | Not specific |
| 100129697 | 0.19837 | | Significant | | Not specific |
| 846 | 0.08543 | CASR | Significant | CASR | Not specific |
| 2877 | −0.09497 | GPX2 | Significant | GPX2 | Not specific |
| 4938 | 0.12382 | OAS1 | Significant | OAS1 | Not specific |
| 27074 | 0.19672 | LAMP3 | Significant | LAMP3 | Not specific |
| 23213 | 0.16479 | SULF1 | Significant | SULF1 | Not specific |
| 101930405 | 0.19753 | | Significant | | Not specific |
| 8728 | 0.16146 | ADAM19 | Significant | ADAM19 | Not specific |
| 10200 | −0.21193 | MPHOSPH6 | Significant | MPHOSPH6 | Not specific |
| 78989 | 0.17462 | COLEC11 | Significant | COLEC11 | Not specific |
| 133418 | 0.16536 | EMB | Significant | EMB | Not specific |
| 10537 | 0.18173 | UBD | Significant | UBD | Not specific |
| 160364 | 0.21657 | CLEC12A | Significant | CLEC12A | Not specific |
| 54 | 0.20346 | ACP5 | Significant | ACP5 | Not specific |
| 54557 | −0.05296 | SGTB | Significant | SGTB | Not specific |
| 8638 | 0.16404 | OASL | Significant | OASL | Not specific |
| 409 | 0.17771 | ARRB2 | Significant | ARRB2 | Not specific |
| 26033 | 0.12464 | ATRNL1 | Significant | ATRNL1 | Not specific |
| 3383 | 0.16394 | ICAM1 | Significant | ICAM1 | Not specific |
| 57715 | 0.07313 | SEMA4G | Significant | SEMA4G | Not specific |
| 5142 | 0.15000 | PDE4B | Significant | PDE4B | Not specific |
| 164668 | 0.22575 | APOBEC3H | Significant | APOBEC3H | Not specific |
| 9246 | 0.17017 | UBE2L6 | Significant | UBE2L6 | Not specific |
| 164118 | 0.15566 | TTC24 | Significant | TTC24 | Not specific |
| 10993 | 0.09622 | SDS | Significant | SDS | Not specific |
| 27036 | 0.14512 | SIGLEC7 | Significant | SIGLEC7 | Not specific |
| 639 | 0.19460 | PRDM1 | Significant | PRDM1 | Not specific |
| 79713 | 0.15774 | IGFLR1 | Significant | IGFLR1 | Not specific |
| 2793 | 0.18315 | GNGT2 | Significant | GNGT2 | Not specific |
| 203100 | 0.19100 | HTRA4 | Significant | HTRA4 | Not specific |
| 1436 | 0.22651 | CSF1R | Significant | CSF1R | Not specific |
| 219537 | 0.11930 | SMTNL1 | Significant | SMTNL1 | Not specific |
| 3823 | 0.17625 | KLRC3 | Significant | KLRC3 | Not specific |
| 4939 | 0.13151 | OAS2 | Significant | OAS2 | Not specific |
| 140 | 0.15924 | ADORA3 | Significant | ADORA3 | Not specific |
| 4867 | 0.05650 | NPHP1 | Significant | NPHP1 | Not specific |
| 5920 | 0.19528 | RARRES3 | Significant | RARRES3 | Not specific |
| 6171 | −0.14714 | RPL41 | Significant | RPL41 | Not specific |
| 84290 | 0.02054 | CAPNS2 | Significant | CAPNS2 | Not specific |
| 3437 | 0.11133 | IFIT3 | Significant | IFIT3 | Not specific |
| 7903 | 0.19616 | ST8SIA4 | Significant | ST8SIA4 | Not specific |
| 155038 | 0.23672 | GIMAP8 | Significant | GIMAP8 | Not specific |
| 26071 | −0.16116 | FAM127B | Significant | FAM127B | Not specific |
| 6519 | 0.05700 | SLC3A1 | Significant | SLC3A1 | Not specific |
| 152559 | −0.13299 | PAQR3 | Significant | PAQR3 | Not specific |
| 940 | 0.23263 | CD28 | Significant | CD28 | Not specific |
| 85479 | 0.18360 | DNAJC5B | Significant | DNAJC5B | Not specific |
| 5727 | 0.14337 | PTCH1 | Significant | PTCH1 | Not specific |
| 126364 | 0.18613 | LRRC25 | Significant | LRRC25 | Not specific |
| 968 | 0.19903 | CD68 | Significant | CD68 | Not specific |
| 80774 | 0.13405 | LIMD2 | Significant | LIMD2 | Not specific |
| 3960 | −0.15196 | LGALS4 | Significant | LGALS4 | Not specific |
| 4318 | 0.17911 | MMP9 | Significant | MMP9 | Not specific |
| 4050 | 0.16518 | LTB | Significant | LTB | Not specific |
| 2342 | −0.11578 | FNTB | Significant | FNTB | Not specific |
| 597 | 0.12796 | BCL2A1 | Significant | BCL2A1 | Not specific |
| 23547 | 0.18404 | LILRA4 | Significant | LILRA4 | Not specific |
| 27071 | 0.15460 | DAPP1 | Significant | DAPP1 | Not specific |
| 6789 | 0.16849 | STK4 | Significant | STK4 | Not specific |
| 11184 | 0.14398 | MAP4K1 | Significant | MAP4K1 | Not specific |
| 10110 | 0.09458 | SGK2 | Significant | SGK2 | Not specific |
| 286336 | 0.20323 | FAM78A | Significant | FAM78A | Not specific |
| 969 | 0.09497 | CD69 | Significant | CD69 | Not specific |
| 79825 | 0.13357 | EFCC1 | Significant | EFCC1 | Not specific |
| 3600 | 0.17464 | IL15 | Significant | IL15 | Not specific |
| 10800 | 0.19968 | CYSLTR1 | Significant | CYSLTR1 | Not specific |
| 27233 | 0.02463 | SULT1C4 | Significant | SULT1C4 | Not specific |

TABLE 2-continued

| | | | | | |
|---|---|---|---|---|---|
| 3824 | 0.17998 | KLRD1 | Significant | KLRD1 | Not specific |
| 154 | 0.15860 | ADRB2 | Significant | ADRB2 | Not specific |
| 7133 | 0.16189 | TNFRSF1B | Significant | TNFRSF1B | Not specific |
| 5046 | 0.09752 | PCSK6 | Significant | PCSK6 | Not specific |
| 114769 | 0.17075 | CARD16 | Significant | CARD16 | Not specific |
| 8676 | 0.08915 | STX11 | Significant | STX11 | Not specific |
| 3055 | 0.19965 | HCK | Significant | HCK | Not specific |
| 7474 | 0.03448 | WNT5A | Significant | WNT5A | Not specific |
| 2908 | 0.11773 | NR3C1 | Significant | NR3C1 | Not specific |
| 4210 | 0.09283 | MEFV | Significant | MEFV | Not specific |
| 9332 | 0.21957 | CD163 | Significant | CD163 | Not specific |
| 11009 | 0.16545 | IL24 | Significant | IL24 | Not specific |
| 6793 | 0.13940 | STK10 | Significant | STK10 | Not specific |
| 5079 | 0.14256 | PAX5 | Significant | PAX5 | Not specific |
| 3120 | 0.16934 | HLA-DQB2 | Significant | HLA-DQB2 | Not specific |
| 26051 | 0.17407 | PPP1R16B | Significant | PPP1R16B | Not specific |
| 1731 | 0.18428 | SEPT1 | Significant | SEPT1 | Not specific |
| 7226 | 0.11525 | TRPM2 | Significant | TRPM2 | Not specific |
| 2264 | 0.08712 | FGFR4 | Significant | FGFR4 | Not specific |
| 9935 | 0.12844 | MAFB | Significant | MAFB | Not specific |
| 137209 | −0.17802 | ZNF572 | Significant | ZNF572 | Not specific |
| 5579 | 0.20442 | PRKCB | Significant | PRKCB | Not specific |
| 91409 | 0.06912 | CCDC74B | Significant | CCDC74B | Not specific |
| 348 | 0.17765 | APOE | Significant | APOE | Not specific |
| 10797 | 0.06976 | MTHFD2 | Significant | MTHFD2 | Not specific |
| 83666 | 0.15014 | PARP9 | Significant | PARP9 | Not specific |
| 341640 | 0.11833 | FREM2 | Significant | FREM2 | Not specific |
| 55220 | 0.07941 | KLHDC8A | Significant | KLHDC8A | Not specific |
| 50943 | 0.12263 | FOXP3 | Significant | FOXP3 | Not specific |
| 84957 | 0.05839 | RELT | Significant | RELT | Not specific |
| 54518 | 0.16816 | APBB1IP | Significant | APBB1IP | Not specific |
| 9047 | 0.07667 | SH2D2A | Significant | SH2D2A | Not specific |
| 25805 | 0.11070 | BAMBI | Significant | BAMBI | Not specific |
| 80301 | 0.11478 | PLEKHO2 | Significant | PLEKHO2 | Not specific |
| 196403 | 0.03842 | DTX3 | Significant | DTX3 | Not specific |
| 11309 | 0.19518 | SLCO2B1 | Significant | SLCO2B1 | Not specific |
| 5768 | 0.03385 | QSOX1 | Significant | QSOX1 | Not specific |
| 84689 | 0.13324 | MS4A14 | Significant | MS4A14 | Not specific |
| 8330 | −0.10756 | HIST1H2AK | Significant | HIST1H2AK | Not specific |
| 57047 | −0.12540 | PLSCR2 | Significant | PLSCR2 | Not specific |
| 4542 | 0.15909 | MYO1F | Significant | MYO1F | Not specific |
| 83605 | 0.12784 | CCM2 | Significant | CCM2 | Not specific |
| 58189 | 0.08825 | WFDC1 | Significant | WFDC1 | Not specific |

Focusing on the 159 genes that are associated with either the quantity or spatial distribution of CD8+ T cells, consensus clustering was performed on the training data. Six clusters were detected with distinct molecular profiles (FIGS. 6d, 6e, and 6f). More specifically, the top plot of FIG. 6d shows a cumulative distribution function (CDF) of the consensus matrix for number of clusters k varying from 2 to 10. The bottom plot of FIG. 6d whos the relative change in area under the CDF curve per increase in k of 1. FIG. 6e shows heatmap illustrations displaying the consensus matrix for k from k=3 to k=6. FIG. 6f shows a two-dimensional representation of CD8 distribution with the tumor dots shaded by cluster for k from 3 to 6. These six clusters could each be assigned to one of the three previously defined tumor-immune phenotypes, i.e. infiltrated, excluded and desert, given their association with low vs. moderate-to-high total CD8+ T cell quantity, or with CD8+ T cell enrichment in stroma vs. tumor cells.

A 157-gene classifier was built to distinguish these three tumor-immune phenotypes, by applying the Prediction Analysis of Microarrays (PAM) approach to the training set (FIG. 7). This classifier was applied to the remaining 215 tumor samples from the ICON7 collection (FIG. 5c) as an independent testing set. From the ICON7 testing set, 196 out of the 215 samples (91%) could be confidently classified, among which 64 tumors as infiltrated (30%), 44 as excluded (20%), and 88 as desert (41%) (FIG. 5c). CD8 IHC data and digital pathology analysis were available for 122 out of the 215 tumor samples. The two-dimensional metrics defining CD8+ T cell quantities and distribution for these 122 samples confirmed that the classifier assigned them to a sensible immune phenotype (FIG. 5d, right panel). A subset of 39 samples were also selected from the testing set and compared the tumor-immune phenotypes predicted by the 157-gene molecular classifier with those manually annotated by a pathologist. FIG. 7a shows the misclassification error rate overall (top) and per immune phenotype (bottom) for the PAM classifier in function of number of classifier genes ranging from 157 to 1. FIG. 7c shows centroids of the 157 genes per immune phenotype. The results were concordant even with the subjectivity of phenotypes as assigned by pathologists (FIGS. 7c and 7d).

Four clinically and biologically relevant molecular subtypes, i.e. immunoreactive (IMR), mesenchymal (MES), proliferative (PRO) and differentiated (DIF), have been previously identified in ovarian cancer. The relationship between the tumor-immune phenotypes defined in this study and the predicted molecular subtypes based on previously developed classifier (as described in Verhaak, R. G. et al. Prognostically relevant gene signatures of high-grade serous ovarian carcinoma. *J Clin Invest* 123, 517-525, (2013) and Tothill, R. W. et al. Novel molecular subtypes of serous and endometrioid ovarian cancer linked to clinical outcome. *Clin Cancer Res* 14, 5198-5208, (2008), which are hereby incorporated by reference in their entireties for all purposes, was assessed. As shown in FIG. 5e, strong concordance was observed between the two classification schemes in both of the training and testing datasets (n=155 and n=196, respectively) from the ICON7 study. Specifically, the IMR molecular subtype was highly enriched in the infiltrated immune phenotype, while MES tumors were highly enriched in the excluded phenotype. Desert tumors were primarily of the PRO or DIF molecular subtypes. With respect to FIG. 5e, each bar displays the percentage of tumors of particular molecular subtype classified as infiltrated, excluded or desert. Unclassified tumors (n=19) were excluded from the analysis.

Finally, the results indicate a significant association of the tumor-immune phenotypes with clinical outcome in ovarian cancer. A Cox proportional hazards analysis was performed on the dataset from 172 patients enrolled in a chemo-control arm of the ICON7 clinical trial with uniform follow-up. As shown in FIG. 25f, patients with the T cell excluded phenotype showed significant shorter progression free survival (PFS) as compared to patients with the infiltrated or the desert phenotype. Similarly, the MES tumors, a subtype that significantly overlaps with the T cell excluded immune phenotype, also showed significantly worse PFS compared to patients with a PRO or DIF tumor. On the other hand, a significant difference in PFS between the infiltrated and desert immune phenotypes was not detected (FIG. 5f). This may be partly due to the mixed intrinsic biology represented by the desert immune phenotype. Supporting this notion is a trending difference in PFS between the two molecular subtypes enriched in the desert immune phenotype, the DIF and the PRO subtype of ovarian cancer (FIG. 5f). These findings highlighted the clinical relevance of the tumor-immune phenotypes and provided insights into their association with the intrinsic biological processes implicated in the molecular subtypes.

IV.C. Molecular and Immune Features Predictive of Tumor-Immune Phenotypes

Molecular features associated with the two quantitative metrics defining distinct immune phenotypes were identified. FIG. 8a shows a heatmap representing the z-scored expression data of the 159 genes that associate with CD8$^+$ T cell quantity or CD8 spatial distribution in the ICON7 training dataset (n=155). Samples are annotated on top by molecular subtypes, the six-class consensus clustering and the three-class tumor-immune phenotype. Eight genes clusters were identified. Three clusters exhibit similar biology representing cytotoxic effector functions and hence were manually pooled. The detailed gene list is shown in Table 2. A table summarizing the biological features of the three tumor-immune phenotypes is displayed below the heatmap. Among the 159 genes identified in the ICON7 training set, 103 genes associated with total CD8$^+$ T cell quantities mostly constituted a cytotoxic signature (e.g. GZMA, GZMB, GMZH, CD40LG) and served as the primary feature to distinguish the desert tumors from the infiltrated and excluded tumors (FIG. 8a). On the other hand, multiple distinct molecular features were enriched among the 56 genes associated with the CD8$^+$ T cell spatial distribution, including antigen presentation (i.e. TAPBP, PSMB10, HLA-DOB), TGFβ/stromal activity (i.e. FAP, TDO2), neuroendocrine-like features (i.e. LRRTM3, ASTN1, SLC4A4) and metabolism (i.e. UGT1A3, UGT1A5, UGT1A6) (FIG. 8a). The infiltrated and excluded phenotypes both exhibited a cytotoxic immune cell gene signature with variable expression from medium to high, but differed markedly in expression of antigen presentation and stromal genes (FIG. 8a). Compared to the infiltrated tumors, the excluded tumors featured significantly higher expression of the TGFβ-associated activated stromal genes and downregulation of antigen presentation genes. Desert tumors, on the other hand, showed a low cytotoxic gene signature as expected, but uniquely expressed metabolic genes and genes suggestive of a neuroendocrine-like state (FIG. 8a).

Figure 9B:
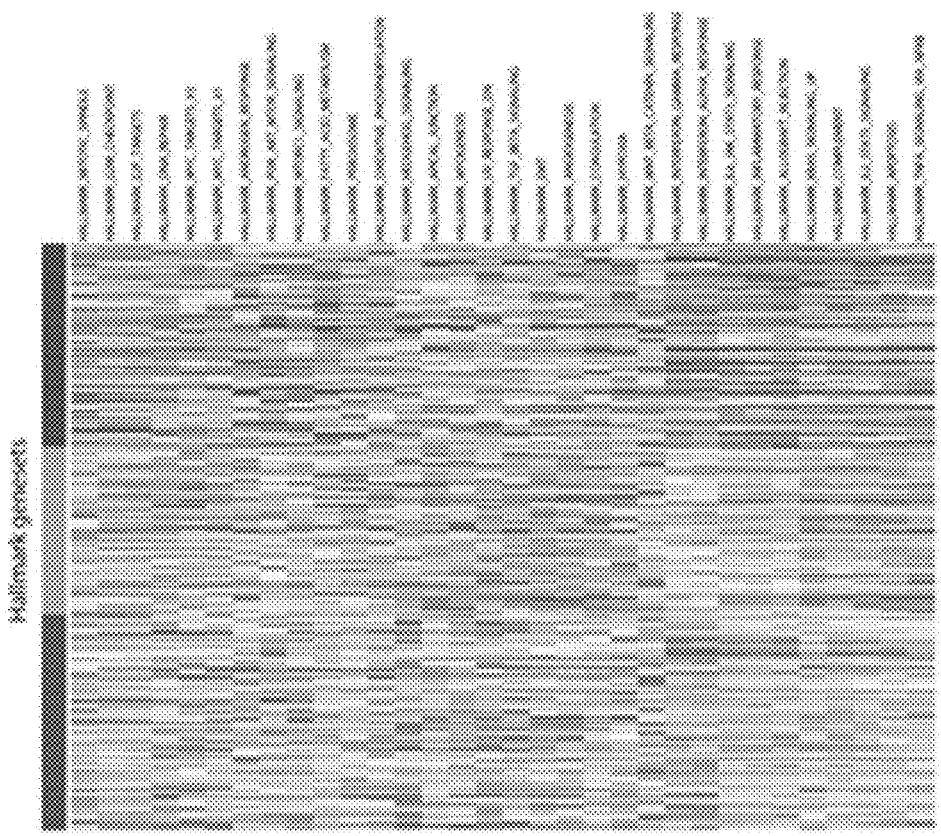
FIGS. 9a-9b show an exemplary pathway enrichment analysis characterizing the 3 immune phenotypes.
Figure 9A:
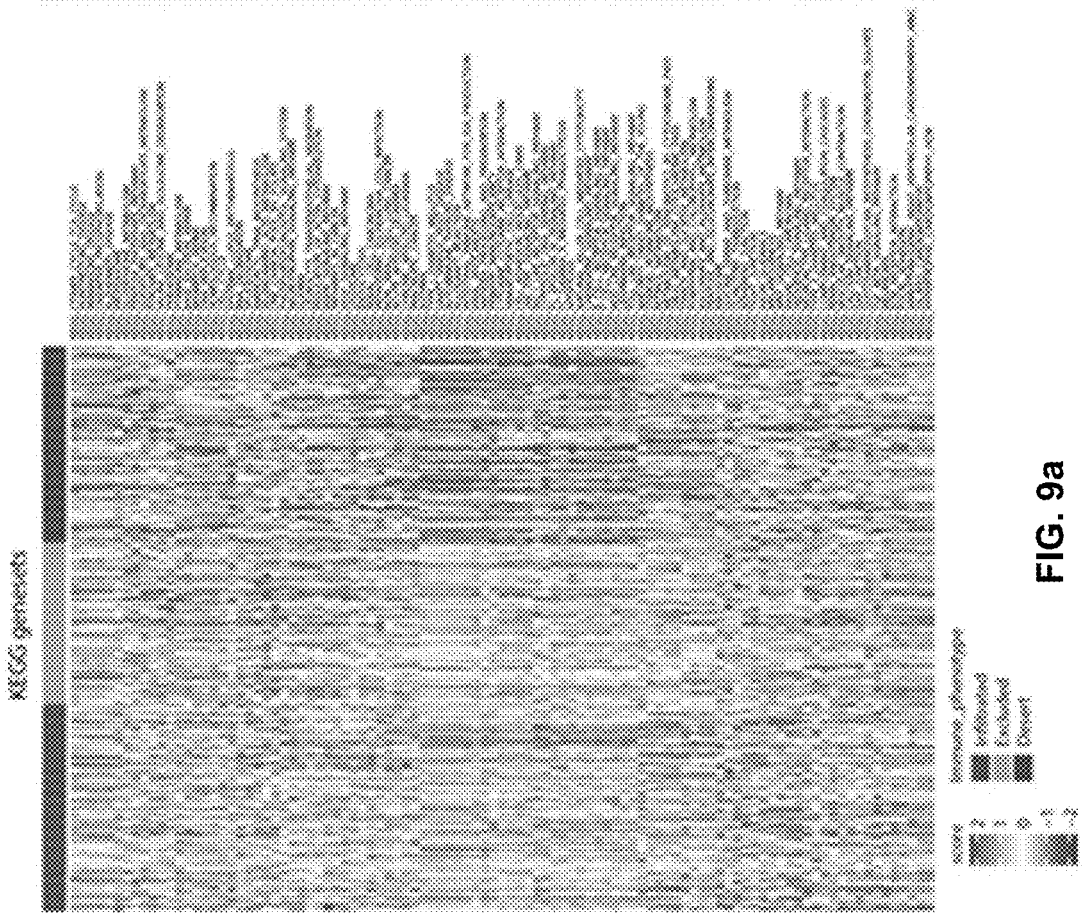

In order to gain a more comprehensive understanding of the biology underlying these tumor-immune phenotypes, pathway enrichment analysis was performed on the full transcriptome of the 370 ICON7 samples. Based on two databases, KEGG (Antigen processing and presentation and Chemokine signaling) and Hallmark (IFNγ response, WNT-β-catenin signaling, TGFβ signaling and Angiogenesis), molecular pathways significantly enriched in each tumor-immune phenotype were summarized in FIG. 8b and FIG. 9. Specifically, FIG. 8b shows enrichment analysis results for the Hallmark pathways in the entire ICON7 dataset (n=370) for (top) infiltrated vs. excluded tumors, and (bottom) desert vs. excluded/infiltrated tumors. Camera was the statistical method applied, and FIG. 9 shows heatmap illustrations with average pathway-level z-scored expression for significant KEGG pathways (FIG. 9a) and significant Hallmark pathways (FIG. 9b). This analysis confirmed the biological features associated with the T cell excluded phenotype previously identified in FIG. 6a, including the downregulation of genes associated with antigen processing and presentation (FIG. 8c), and a strong signal for TGFβ activity with an increased expression of TGFβ ligands, a TGFβ response signature in fibroblasts (F-TBRS) and an overall increase in genes indicative of active TGFβ signaling (FIG. 8d).

Furthermore, pathway analysis revealed additional molecular features characterizing the distinct tumor-immune phenotypes. The pathways characterizing the infiltrated and desert phenotypes are represented in FIG. 8c and those characterizing the excluded tumors in FIG. 8d. For example, the infiltrated tumors showed enriched interferon gamma response (FIG. 8c), plausibly explaining the higher expression of antigen presentation genes in this phenotype. Enrichment for the angiogenesis pathway in the immune excluded tumors was also observed (FIG. 8d). For the immune desert tumors, this phenotype was not only featured by the lowest expression in interferon gamma response and antigen presentation compared to the other two tumor-immune phenotypes, it also showed a significantly downregulation of genes involved in chemotaxis (chemokine signaling) (FIG. 8c), suggesting a defect in T cell recruitment ability. Interestingly, a slight enrichment for the WNT-β-catenin signaling pathway was also detected in the desert tumors. A correlation between the activation of this pathway and low expression of the T cell gene signature has been previously reported in melanoma.

To evaluate in more detail which specific immune and stromal cell types are associated with a given immune phenotype, a cell type enrichment analysis was performed using xCell, a gene signature-based deconvolution method, on the bulk RNAseq datasets of ICON7 study (n=370). The deconvolution analysis confirmed many findings from the machine learning and pathway enrichment analyses, including a high overall immune score in infiltrated and excluded tumors, and the highest overall stromal score in the excluded tumors (FIG. 8e). In addition, the deconvolution analysis was suggestive of a significant enrichment of many immune cell types, including CD8$^+$ T cells, regulatory T cells (Treg), and macrophages were significantly enriched in both of the infiltrated and excluded tumors compared to the desert tumors. Meanwhile, the excluded tumors were specifically enriched for fibroblasts (FIG. 8e).

Figure 10A:
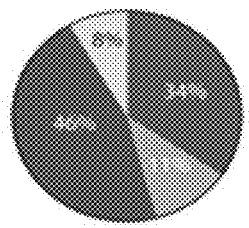
FIGS. 10a-10d show exemplary results generated by using a gene-expression based molecular classifier to predict the immune phenotypes in the vendor procured cohort.

Genetic components, such as tumor mutation burden (TMB), neo-antigen burden, and high genomic instability including microsatellite instability high (MSI-H) and deficient mismatch repair (dMMR), have been shown to associate with increased T cell infiltration and better responses to checkpoint inhibitors in some cancer types. To investigate the impact of genetic components in ovarian cancer in the context of tumor-immune phenotypes, the published ovarian cancer TCGA dataset (n=412) was accessed. Both bulk RNAseq and whole exome sequencing data are available for this dataset. Using the RNAseq data, a tumor-immune phenotype was predicted for each of 412 ovarian tumor samples in the TCGA dataset by applying the 157-gene molecular classifier (FIG. 10a and Table 3). xCell deconvolution analysis of immune and stromal cell types across different tumor-immune phenotypes in the TCGA dataset generated highly concordant results with the ICON7 analysis (data not shown). Furthermore, genetic analysis revealed an overall absence of significant association between tumor-immune phenotypes and TMB, neo-antigen load, Mismatch Repair deficiency (dMMR) or homologous recombination deficiency (HRD) in ovarian cancer, with an exception that a slightly lower neoantigen load was observed in the desert compared to the infiltrated tumors (FIG. 8f). The statistical significance is displayed in FIG. 8f as *p<0.05, p<0.01, *p<0.001, ****p<0.0001 by Wilcoxon test corrected for multiplicity. Together, these results suggest that genetic alterations in ovarian cancer are not a major driver of the infiltration or exclusion of $CD8^+$ T cells.

TABLE 3

| Sample ID | Tumour-immune phenotype |
|---|---|
| TCGA-04-1331-01A-01R-1569-13 | Desert |
| TCGA-04-1332-01A-01R-1564-13 | Desert |
| TCGA-04-1341-01A-01R-1564-13 | Desert |
| TCGA-04-1350-01A-01R-1565-13 | Desert |
| TCGA-04-1356-01A-01R-1569-13 | Desert |
| TCGA-04-1361-01A-01R-1565-13 | Desert |
| TCGA-04-1362-01A-01R-1565-13 | Desert |
| TCGA-04-1364-01A-01R-1565-13 | Desert |
| TCGA-04-1514-01A-01R-1566-13 | Desert |
| TCGA-04-1517-01A-01R-1565-13 | Desert |
| TCGA-04-1519-01A-01R-1565-13 | Desert |
| TCGA-04-1542-01A-01R-1566-13 | Desert |
| TCGA-04-1648-01A-01R-1567-13 | Desert |
| TCGA-04-1651-01A-01R-1567-13 | Desert |
| TCGA-04-1655-01A-01R-1566-13 | Desert |
| TCGA-09-0364-01A-02R-1564-13 | Desert |
| TCGA-09-0367-01A-01R-1564-13 | Desert |
| TCGA-09-0369-01A-01R-1564-13 | Desert |
| TCGA-09-1659-01B-01R-1564-13 | Desert |
| TCGA-09-1661-01B-01R-1566-13 | Desert |
| TCGA-09-1665-01B-01R-1566-13 | Desert |
| TCGA-09-1673-01A-01R-1566-13 | Desert |
| TCGA-09-1674-01A-01R-1566-13 | Desert |
| TCGA-09-2045-01A-01R-1568-13 | Desert |
| TCGA-09-2048-01A-01R-1568-13 | Desert |
| TCGA-09-2054-01A-01R-1568-13 | Desert |
| TCGA-10-0926-01A-01R-1564-13 | Desert |
| TCGA-10-0927-01A-02R-1564-13 | Desert |
| TCGA-10-0928-01A-02R-1564-13 | Desert |
| TCGA-10-0931-01A-01R-1564-13 | Desert |
| TCGA-10-0933-01A-01R-1569-13 | Desert |
| TCGA-10-0934-01A-02R-1564-13 | Desert |
| TCGA-10-0936-01A-01R-1564-13 | Desert |
| TCGA-10-0938-01A-02R-1564-13 | Desert |
| TCGA-13-0720-01A-01R-1564-13 | Desert |
| TCGA-13-0724-01A-01R-1564-13 | Desert |
| TCGA-13-0726-01A-01R-1564-13 | Desert |
| TCGA-13-0727-01A-01R-1564-13 | Desert |
| TCGA-13-0730-01A-01R-1564-13 | Desert |
| TCGA-13-0762-01A-01R-1564-13 | Desert |
| TCGA-13-0765-01A-01R-1564-13 | Desert |
| TCGA-13-0766-01A-02R-1564-13 | Desert |
| TCGA-13-0799-01A-01R-1564-13 | Desert |
| TCGA-13-0800-01A-01R-1564-13 | Desert |
| TCGA-13-0887-01A-01R-1564-13 | Desert |
| TCGA-13-0888-01A-01R-1564-13 | Desert |
| TCGA-13-0891-01A-01R-1564-13 | Desert |
| TCGA-13-0899-01A-01R-1564-13 | Desert |
| TCGA-13-0901-01B-01R-1565-13 | Desert |
| TCGA-13-0905-01B-01R-1565-13 | Desert |
| TCGA-13-0906-01A-01R-1564-13 | Desert |
| TCGA-13-0913-01A-01R-1564-13 | Desert |
| TCGA-13-0913-02A-01R-1564-13 | Desert |
| TCGA-13-0920-01A-01R-1564-13 | Desert |
| TCGA-13-0923-01A-01R-1564-13 | Desert |
| TCGA-13-1403-01A-01R-1565-13 | Desert |
| TCGA-13-1407-01A-01R-1565-13 | Desert |
| TCGA-13-1409-01A-01R-1565-13 | Desert |
| TCGA-13-1477-01A-01R-1565-13 | Desert |
| TCGA-13-1481-01A-01R-1565-13 | Desert |
| TCGA-13-1482-01A-01R-1565-13 | Desert |
| TCGA-13-1483-01A-01R-1565-13 | Desert |
| TCGA-13-1485-01A-02R-1565-13 | Desert |
| TCGA-13-1487-01A-01R-1565-13 | Desert |
| TCGA-13-1488-01A-01R-1565-13 | Desert |
| TCGA-13-1489-01A-01R-1565-13 | Desert |
| TCGA-13-1489-02A-01R-1565-13 | Desert |
| TCGA-13-1492-01A-01R-1565-13 | Desert |
| TCGA-13-1495-01A-01R-1565-13 | Desert |
| TCGA-13-1497-01A-01R-1565-13 | Desert |
| TCGA-13-1501-01A-01R-1565-13 | Desert |
| TCGA-13-1506-01A-01R-1565-13 | Desert |
| TCGA-13-1510-01A-02R-1565-13 | Desert |
| TCGA-13-1511-01A-01R-1565-13 | Desert |
| TCGA-13-1512-01A-01R-1565-13 | Desert |
| TCGA-20-1683-01A-01R-1566-13 | Desert |
| TCGA-20-1684-01A-01R-1566-13 | Desert |
| TCGA-20-1686-01A-01R-1566-13 | Desert |
| TCGA-23-1021-01B-01R-1564-13 | Desert |
| TCGA-23-1022-01A-01R-1564-13 | Desert |
| TCGA-23-1023-01R-01R-1564-13 | Desert |
| TCGA-23-1024-01A-02R-1564-13 | Desert |
| TCGA-23-1028-01A-01R-1564-13 | Desert |
| TCGA-23-1029-01B-01R-1567-13 | Desert |
| TCGA-23-1030-01A-02R-1564-13 | Desert |
| TCGA-23-1032-01A-02R-1564-13 | Desert |
| TCGA-23-1107-01A-01R-1564-13 | Desert |
| TCGA-23-1110-01A-01R-1564-13 | Desert |
| TCGA-23-1111-01A-01R-1567-13 | Desert |
| TCGA-23-1113-01A-01R-1564-13 | Desert |
| TCGA-23-1114-01B-01R-1566-13 | Desert |
| TCGA-23-1118-01A-01R-1564-13 | Desert |
| TCGA-23-1122-01A-01R-1565-13 | Desert |
| TCGA-23-1809-01A-01R-1566-13 | Desert |
| TCGA-23-2081-01A-01R-1568-13 | Desert |
| TCGA-24-0966-01A-01R-1564-13 | Desert |
| TCGA-24-0970-01B-01R-1565-13 | Desert |
| TCGA-24-0975-01A-02R-1565-13 | Desert |
| TCGA-24-0979-01A-01R-1565-13 | Desert |
| TCGA-24-0982-01A-01R-1565-13 | Desert |
| TCGA-24-1103-01A-01R-1565-13 | Desert |
| TCGA-24-1105-01A-01R-1565-13 | Desert |
| TCGA-24-1413-01A-01R-1565-13 | Desert |
| TCGA-24-1416-01A-01R-1565-13 | Desert |
| TCGA-24-1418-01A-01R-1565-13 | Desert |
| TCGA-24-1419-01A-01R-1565-13 | Desert |
| TCGA-24-1423-01A-01R-1565-13 | Desert |
| TCGA-24-1424-01A-01R-1565-13 | Desert |
| TCGA-24-1426-01A-01R-1565-13 | Desert |
| TCGA-24-1430-01A-01R-1566-13 | Desert |
| TCGA-24-1467-01A-01R-1566-13 | Desert |
| TCGA-24-1469-01A-01R-1566-13 | Desert |
| TCGA-24-1544-01A-01R-1566-13 | Desert |
| TCGA-24-1548-01A-01R-1566-13 | Desert |
| TCGA-24-1552-01A-01R-1566-13 | Desert |
| TCGA-24-1555-01A-01R-1566-13 | Desert |
| TCGA-24-1557-01A-01R-1566-13 | Desert |
| TCGA-24-1558-01A-01R-1566-13 | Desert |

TABLE 3-continued

| Sample ID | Tumour-immune phenotype |
|---|---|
| TCGA-24-1560-01A-01R-1566-13 | Desert |
| TCGA-24-1567-01A-01R-1566-13 | Desert |
| TCGA-24-1603-01A-01R-1566-13 | Desert |
| TCGA-24-1604-01A-01R-1566-13 | Desert |
| TCGA-24-1616-01A-01R-1566-13 | Desert |
| TCGA-24-1844-01A-01R-1567-13 | Desert |
| TCGA-24-1923-01A-01R-1567-13 | Desert |
| TCGA-24-2024-01A-02R-1568-13 | Desert |
| TCGA-24-2027-01A-01R-1567-13 | Desert |
| TCGA-24-2033-01A-01R-1568-13 | Desert |
| TCGA-24-2036-01A-01R-1568-13 | Desert |
| TCGA-24-2038-01A-01R-1568-13 | Desert |
| TCGA-24-2254-01A-01R-1568-13 | Desert |
| TCGA-24-2297-01A-01R-1568-13 | Desert |
| TCGA-24-2298-01A-01R-1569-13 | Desert |
| TCGA-25-1312-01A-01R-1565-13 | Desert |
| TCGA-25-1315-01A-01R-1565-13 | Desert |
| TCGA-25-1316-01A-01R-1565-13 | Desert |
| TCGA-25-1317-01A-01R-1565-13 | Desert |
| TCGA-25-1321-01A-01R-1565-13 | Desert |
| TCGA-25-1323-01A-01R-1565-13 | Desert |
| TCGA-25-1324-01A-01R-1565-13 | Desert |
| TCGA-25-1627-01A-01R-1566-13 | Desert |
| TCGA-25-1631-01A-01R-1569-13 | Desert |
| TCGA-25-1632-01A-01R-1566-13 | Desert |
| TCGA-25-1634-01A-01R-1566-13 | Desert |
| TCGA-25-1870-01A-01R-1567-13 | Desert |
| TCGA-25-1871-01A-01R-1567-13 | Desert |
| TCGA-25-1877-01A-01R-1567-13 | Desert |
| TCGA-25-2393-01A-01R-1569-13 | Desert |
| TCGA-25-2397-01A-01R-1569-13 | Desert |
| TCGA-25-2400-01A-01R-1569-13 | Desert |
| TCGA-29-1691-01A-01R-1566-13 | Desert |
| TCGA-29-1693-01A-01R-1567-13 | Desert |
| TCGA-29-1696-01A-01R-1567-13 | Desert |
| TCGA-29-1697-01A-01R-1567-13 | Desert |
| TCGA-29-1702-01A-01R-1567-13 | Desert |
| TCGA-29-1703-01A-01R-1567-13 | Desert |
| TCGA-29-1762-01A-01R-1567-13 | Desert |
| TCGA-29-1770-01A-01R-1567-13 | Desert |
| TCGA-29-1770-02A-01R-1567-13 | Desert |
| TCGA-29-1774-01A-01R-1567-13 | Desert |
| TCGA-29-1776-01A-01R-1567-13 | Desert |
| TCGA-29-2414-01A-02R-1569-13 | Desert |
| TCGA-29-2425-01A-01R-1569-13 | Desert |
| TCGA-30-1714-01A-02R-1567-13 | Desert |
| TCGA-30-1853-01A-02R-1567-13 | Desert |
| TCGA-30-1861-01A-01R-1568-13 | Desert |
| TCGA-30-1866-01A-02R-1568-13 | Desert |
| TCGA-36-1570-01A-01R-1566-13 | Desert |
| TCGA-36-1571-01A-01R-1566-13 | Desert |
| TCGA-36-1575-01A-01R-1566-13 | Desert |
| TCGA-36-1577-01A-01R-1566-13 | Desert |
| TCGA-57-1582-01A-01R-1566-13 | Desert |
| TCGA-57-1583-01A-01R-1566-13 | Desert |
| TCGA-57-1584-01A-01R-1566-13 | Desert |
| TCGA-57-1586-01A-02R-1567-13 | Desert |
| TCGA-57-1993-01A-01R-1568-13 | Desert |
| TCGA-59-2350-01A-01R-1569-13 | Desert |
| TCGA-59-2355-01A-01R-1569-13 | Desert |
| TCGA-59-2363-01A-01R-1569-13 | Desert |
| TCGA-61-1728-01A-01R-1568-13 | Desert |
| TCGA-61-1733-01A-01R-1567-13 | Desert |
| TCGA-61-1743-01A-01R-1568-13 | Desert |
| TCGA-61-1900-01A-01R-1567-13 | Desert |
| TCGA-61-1910-01A-01R-1567-13 | Desert |
| TCGA-61-2008-01A-02R-1568-13 | Desert |
| TCGA-61-2092-01A-01R-1568-13 | Desert |
| TCGA-61-2098-01A-01R-1568-13 | Desert |
| TCGA-61-2102-01A-01R-1568-13 | Desert |
| TCGA-61-2110-01A-01R-1568-13 | Desert |
| TCGA-04-1337-01A-01R-1564-13 | Excluded |
| TCGA-04-1338-01A-01R-1564-13 | Excluded |
| TCGA-04-1343-01A-01R-1564-13 | Excluded |
| TCGA-04-1530-01A-02R-1569-13 | Excluded |
| TCGA-13-0714-01A-01R-1564-13 | Excluded |
| TCGA-13-0768-01A-01R-1569-13 | Excluded |
| TCGA-13-0883-01A-02R-1569-13 | Excluded |
| TCGA-13-0890-01A-01R-1564-13 | Excluded |
| TCGA-13-0919-01A-01R-1564-13 | Excluded |
| TCGA-13-1405-01A-01R-1565-13 | Excluded |
| TCGA-13-1408-01A-01R-1565-13 | Excluded |
| TCGA-13-1499-01A-01R-1565-13 | Excluded |
| TCGA-13-1505-01A-01R-1565-13 | Excluded |
| TCGA-13-1509-01A-01R-1565-13 | Excluded |
| TCGA-20-1682-01A-01R-1564-13 | Excluded |
| TCGA-23-1116-01A-01R-1564-13 | Excluded |
| TCGA-23-2078-01A-01R-1568-13 | Excluded |
| TCGA-24-1422-01A-01R-1565-13 | Excluded |
| TCGA-24-1425-01A-02R-1566-13 | Excluded |
| TCGA-24-1427-01A-01R-1565-13 | Excluded |
| TCGA-24-1434-01A-01R-1566-13 | Excluded |
| TCGA-24-1546-01A-01R-1566-13 | Excluded |
| TCGA-24-1550-01A-01R-1566-13 | Excluded |
| TCGA-24-1563-01A-01R-1566-13 | Excluded |
| TCGA-24-1849-01A-01R-1567-13 | Excluded |
| TCGA-24-1850-01A-01R-1567-13 | Excluded |
| TCGA-24-2035-01A-01R-1568-13 | Excluded |
| TCGA-24-2271-01A-01R-1568-13 | Excluded |
| TCGA-24-2280-01A-01R-1568-13 | Excluded |
| TCGA-24-2289-01A-01R-1568-13 | Excluded |
| TCGA-24-2293-01A-01R-1568-13 | Excluded |
| TCGA-25-1320-01A-01R-1565-13 | Excluded |
| TCGA-25-1328-01A-01R-1565-13 | Excluded |
| TCGA-25-1626-01A-01R-1566-13 | Excluded |
| TCGA-25-1633-01A-01R-1566-13 | Excluded |
| TCGA-25-2042-01A-01R-1568-13 | Excluded |
| TCGA-25-2398-01A-01R-1569-13 | Excluded |
| TCGA-29-1705-01A-01R-1567-13 | Excluded |
| TCGA-29-1766-01A-01R-1567-13 | Excluded |
| TCGA-30-1862-01A-02R-1568-13 | Excluded |
| TCGA-30-1891-01A-01R-1568-13 | Excluded |
| TCGA-36-1569-01A-01R-1566-13 | Excluded |
| TCGA-36-1576-01A-01R-1566-13 | Excluded |
| TCGA-36-1580-01A-01R-1566-13 | Excluded |
| TCGA-57-1585-01A-01R-1566-13 | Excluded |
| TCGA-61-1721-01A-01R-1569-13 | Excluded |
| TCGA-61-2009-01A-01R-1568-13 | Excluded |
| TCGA-04-1348-01A-01R-1565-13 | Infiltrated |
| TCGA-04-1357-01A-01R-1565-13 | Infiltrated |
| TCGA-04-1365-01A-01R-1565-13 | Infiltrated |
| TCGA-09-0366-01A-01R-1564-13 | Infiltrated |
| TCGA-09-1662-01A-01R-1566-13 | Infiltrated |
| TCGA-09-1666-01A-01R-1566-13 | Infiltrated |
| TCGA-09-1667-01C-01R-1566-13 | Infiltrated |
| TCGA-09-1668-01B-01R-1566-13 | Infiltrated |
| TCGA-09-1669-01A-01R-1566-13 | Infiltrated |
| TCGA-09-1670-01A-01R-1566-13 | Infiltrated |
| TCGA-09-2044-01B-01R-1568-13 | Infiltrated |
| TCGA-09-2051-01A-01R-1568-13 | Infiltrated |
| TCGA-09-2053-01C-01R-1568-13 | Infiltrated |
| TCGA-09-2056-01B-01R-1568-13 | Infiltrated |
| TCGA-10-0937-01A-02R-1564-13 | Infiltrated |
| TCGA-13-0725-01A-01R-1564-13 | Infiltrated |
| TCGA-13-0760-01A-01R-1564-13 | Infiltrated |
| TCGA-13-0795-01A-01R-1564-13 | Infiltrated |
| TCGA-13-0797-01A-01R-1564-13 | Infiltrated |
| TCGA-13-0801-01A-01R-1564-13 | Infiltrated |
| TCGA-13-0804-01A-01R-1564-13 | Infiltrated |
| TCGA-13-0884-01B-01R-1565-13 | Infiltrated |
| TCGA-13-0885-01A-02R-1569-13 | Infiltrated |
| TCGA-13-0893-01B-01R-1565-13 | Infiltrated |
| TCGA-13-0897-01A-01R-1564-13 | Infiltrated |
| TCGA-13-0916-01A-01R-1564-13 | Infiltrated |
| TCGA-13-0924-01A-01R-1564-13 | Infiltrated |
| TCGA-13-1496-01A-01R-1565-13 | Infiltrated |
| TCGA-13-1498-01A-01R-1565-13 | Infiltrated |
| TCGA-13-1507-01A-01R-1565-13 | Infiltrated |
| TCGA-13-2060-01A-01R-1568-13 | Infiltrated |
| TCGA-20-0987-01A-02R-1564-13 | Infiltrated |
| TCGA-20-0991-01A-01R-1564-13 | Infiltrated |
| TCGA-20-1685-01A-01R-1566-13 | Infiltrated |
| TCGA-20-1687-01A-01R-1566-13 | Infiltrated |
| TCGA-23-1023-01A-02R-1564-13 | Infiltrated |
| TCGA-23-1026-01B-01R-1569-13 | Infiltrated |
| TCGA-23-1027-01A-02R-1564-13 | Infiltrated |

TABLE 3-continued

| Sample ID | Tumour-immune phenotype |
|---|---|
| TCGA-23-1120-01A-02R-1565-13 | Infiltrated |
| TCGA-23-1123-01A-01R-1565-13 | Infiltrated |
| TCGA-23-2077-01A-01R-1568-13 | Infiltrated |
| TCGA-23-2084-01A-02R-1568-13 | Infiltrated |
| TCGA-24-0968-01A-01R-1569-13 | Infiltrated |
| TCGA-24-1104-01A-01R-1565-13 | Infiltrated |
| TCGA-24-1417-01A-01R-1565-13 | Infiltrated |
| TCGA-24-1428-01A-01R-1564-13 | Infiltrated |
| TCGA-24-1431-01A-01R-1566-13 | Infiltrated |
| TCGA-24-1435-01A-01R-1566-13 | Infiltrated |
| TCGA-24-1436-01A-01R-1566-13 | Infiltrated |
| TCGA-24-1464-01A-01R-1566-13 | Infiltrated |
| TCGA-24-1470-01A-01R-1566-13 | Infiltrated |
| TCGA-24-1471-01A-01R-1566-13 | Infiltrated |
| TCGA-24-1474-01A-01R-1566-13 | Infiltrated |
| TCGA-24-1549-01A-01R-1566-13 | Infiltrated |
| TCGA-24-1551-01A-01R-1566-13 | Infiltrated |
| TCGA-24-1553-01A-01R-1566-13 | Infiltrated |
| TCGA-24-1556-01A-01R-1566-13 | Infiltrated |
| TCGA-24-1564-01A-01R-1566-13 | Infiltrated |
| TCGA-24-1565-01A-01R-1566-13 | Infiltrated |
| TCGA-24-1842-01A-01R-1567-13 | Infiltrated |
| TCGA-24-1845-01A-01R-1567-13 | Infiltrated |
| TCGA-24-1846-01A-01R-1567-13 | Infiltrated |
| TCGA-24-1847-01A-01R-1566-13 | Infiltrated |
| TCGA-24-1924-01A-01R-1567-13 | Infiltrated |
| TCGA-24-1930-01A-01R-1567-13 | Infiltrated |
| TCGA-24-2019-01A-02R-1568-13 | Infiltrated |
| TCGA-24-2023-01A-01R-1567-13 | Infiltrated |
| TCGA-24-2026-01A-01R-1567-13 | Infiltrated |
| TCGA-24-2261-01A-01R-1568-13 | Infiltrated |
| TCGA-24-2262-01A-01R-1568-13 | Infiltrated |
| TCGA-24-2267-01A-01R-1568-13 | Infiltrated |
| TCGA-24-2281-01A-01R-1568-13 | Infiltrated |
| TCGA-24-2290-01A-01R-1568-13 | Infiltrated |
| TCGA-25-1313-01A-01R-1565-13 | Infiltrated |
| TCGA-25-1314-01A-01R-1565-13 | Infiltrated |
| TCGA-25-1318-01A-01R-1565-13 | Infiltrated |
| TCGA-25-1319-01A-01R-1565-13 | Infiltrated |
| TCGA-25-1322-01A-01R-1565-13 | Infiltrated |
| TCGA-25-1625-01A-01R-1566-13 | Infiltrated |
| TCGA-25-1630-01A-01R-1566-13 | Infiltrated |
| TCGA-25-1635-01A-01R-1566-13 | Infiltrated |
| TCGA-25-2391-01A-01R-1569-13 | Infiltrated |
| TCGA-25-2392-01A-01R-1569-13 | Infiltrated |
| TCGA-25-2396-01A-01R-1569-13 | Infiltrated |
| TCGA-25-2399-01A-01R-1569-13 | Infiltrated |
| TCGA-25-2401-01A-01R-1569-13 | Infiltrated |
| TCGA-25-2404-01A-01R-1569-13 | Infiltrated |
| TCGA-25-2409-01A-01R-1569-13 | Infiltrated |
| TCGA-29-1688-01A-01R-1566-13 | Infiltrated |
| TCGA-29-1690-01A-01R-1566-13 | Infiltrated |
| TCGA-29-1699-01A-01R-1567-13 | Infiltrated |
| TCGA-29-1707-02A-01R-1567-13 | Infiltrated |
| TCGA-29-1710-01A-02R-1567-13 | Infiltrated |
| TCGA-29-1711-01A-01R-1567-13 | Infiltrated |
| TCGA-29-1761-01A-01R-1567-13 | Infiltrated |
| TCGA-29-1763-01A-02R-1567-13 | Infiltrated |
| TCGA-29-1769-01A-01R-1567-13 | Infiltrated |
| TCGA-29-1778-01A-01R-1567-13 | Infiltrated |
| TCGA-29-1781-01A-01R-1567-13 | Infiltrated |
| TCGA-29-1783-01A-01R-1567-13 | Infiltrated |
| TCGA-29-1784-01A-02R-1567-13 | Infiltrated |
| TCGA-29-1785-01A-01R-1567-13 | Infiltrated |
| TCGA-29-2414-02A-01R-1569-13 | Infiltrated |
| TCGA-29-2427-01A-01R-1569-13 | Infiltrated |
| TCGA-29-2428-01A-01R-1569-13 | Infiltrated |
| TCGA-30-1855-01A-01R-1567-13 | Infiltrated |
| TCGA-30-1860-01A-01R-1568-13 | Infiltrated |
| TCGA-31-1944-01A-01R-1568-13 | Infiltrated |
| TCGA-31-1946-01A-01R-1568-13 | Infiltrated |
| TCGA-31-1950-01A-01R-1568-13 | Infiltrated |
| TCGA-31-1951-01A-01R-1568-13 | Infiltrated |
| TCGA-31-1953-01A-01R-1568-13 | Infiltrated |
| TCGA-31-1956-01A-01R-1568-13 | Infiltrated |
| TCGA-36-1568-01A-01R-1566-13 | Infiltrated |
| TCGA-36-1574-01A-01R-1566-13 | Infiltrated |
| TCGA-36-1578-01A-01R-1566-13 | Infiltrated |
| TCGA-36-1581-01A-01R-1566-13 | Infiltrated |
| TCGA-59-2348-01A-01R-1569-13 | Infiltrated |
| TCGA-59-2351-01A-01R-1569-13 | Infiltrated |
| TCGA-59-2352-01A-01R-1569-13 | Infiltrated |
| TCGA-61-1724-01A-01R-1568-13 | Infiltrated |
| TCGA-61-1725-01A-01R-1567-13 | Infiltrated |
| TCGA-61-1736-01B-01R-1568-13 | Infiltrated |
| TCGA-61-1740-01A-01R-1567-13 | Infiltrated |
| TCGA-61-1741-01A-02R-1567-13 | Infiltrated |
| TCGA-61-1907-01A-01R-1567-13 | Infiltrated |
| TCGA-61-1911-01A-01R-1567-13 | Infiltrated |
| TCGA-61-1914-01A-01R-1567-13 | Infiltrated |
| TCGA-61-1917-01A-01R-1568-13 | Infiltrated |
| TCGA-61-1918-01A-01R-1568-13 | Infiltrated |
| TCGA-61-1995-01A-01R-1568-13 | Infiltrated |
| TCGA-61-1998-01A-01R-1568-13 | Infiltrated |
| TCGA-61-2000-01A-01R-1568-13 | Infiltrated |
| TCGA-61-2002-01A-01R-1568-13 | Infiltrated |
| TCGA-61-2008-02A-01R-1568-13 | Infiltrated |
| TCGA-61-2012-01A-01R-1568-13 | Infiltrated |
| TCGA-61-2016-01A-01R-1568-13 | Infiltrated |
| TCGA-61-2094-01A-01R-1568-13 | Infiltrated |
| TCGA-61-2095-01A-01R-1568-13 | Infiltrated |
| TCGA-61-2097-01A-02R-1568-13 | Infiltrated |
| TCGA-61-2104-01A-01R-1568-13 | Infiltrated |
| TCGA-61-2111-01A-01R-1568-13 | Infiltrated |
| TCGA-13-0886-01A-01R-1569-13 | unclassified |
| TCGA-13-0900-01B-01R-1565-13 | unclassified |
| TCGA-13-0908-01B-01R-1565-13 | unclassified |
| TCGA-13-0911-01A-01R-1564-13 | unclassified |
| TCGA-13-1404-01A-01R-1565-13 | unclassified |
| TCGA-13-1410-01A-01R-1565-13 | unclassified |
| TCGA-13-1411-01A-01R-1565-13 | unclassified |
| TCGA-23-1109-01A-01R-1564-13 | unclassified |
| TCGA-23-1119-01A-02R-1565-13 | unclassified |
| TCGA-24-1463-01A-01R-1566-13 | unclassified |
| TCGA-24-1545-01A-01R-1566-13 | unclassified |
| TCGA-24-1562-01A-01R-1566-13 | unclassified |
| TCGA-24-2288-01A-01R-1568-13 | unclassified |
| TCGA-25-1326-01A-01R-1565-13 | unclassified |
| TCGA-25-1329-01A-01R-1565-13 | unclassified |
| TCGA-25-1623-01A-01R-1566-13 | unclassified |
| TCGA-25-1628-01A-01R-1566-13 | unclassified |
| TCGA-29-1694-01A-01R-1567-13 | unclassified |
| TCGA-29-1695-01A-01R-1567-13 | unclassified |
| TCGA-29-1698-01A-01R-1567-13 | unclassified |
| TCGA-29-1701-01A-01R-1567-13 | unclassified |
| TCGA-29-1705-02A-01R-1567-13 | unclassified |
| TCGA-29-1768-01A-01R-1567-13 | unclassified |
| TCGA-29-1777-01A-01R-1567-13 | unclassified |
| TCGA-30-1718-01A-01R-1567-13 | unclassified |
| TCGA-30-1892-01A-01R-1568-13 | unclassified |
| TCGA-31-1959-01A-01R-1568-13 | unclassified |
| TCGA-59-2354-01A-01R-1569-13 | unclassified |
| TCGA-61-1737-01A-01R-1567-13 | unclassified |
| TCGA-61-1738-01A-01R-1567-13 | unclassified |
| TCGA-61-1919-01A-01R-1568-13 | unclassified |
| TCGA-61-2003-01A-01R-1568-13 | unclassified |
| TCGA-61-2109-01A-01R-1568-13 | unclassified |
| TCGA-61-2113-01A-01R-1568-13 | unclassified |

Figure 10B:
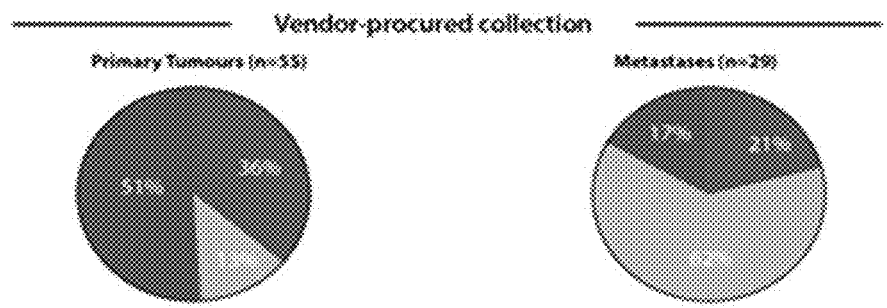
Figure 10C:
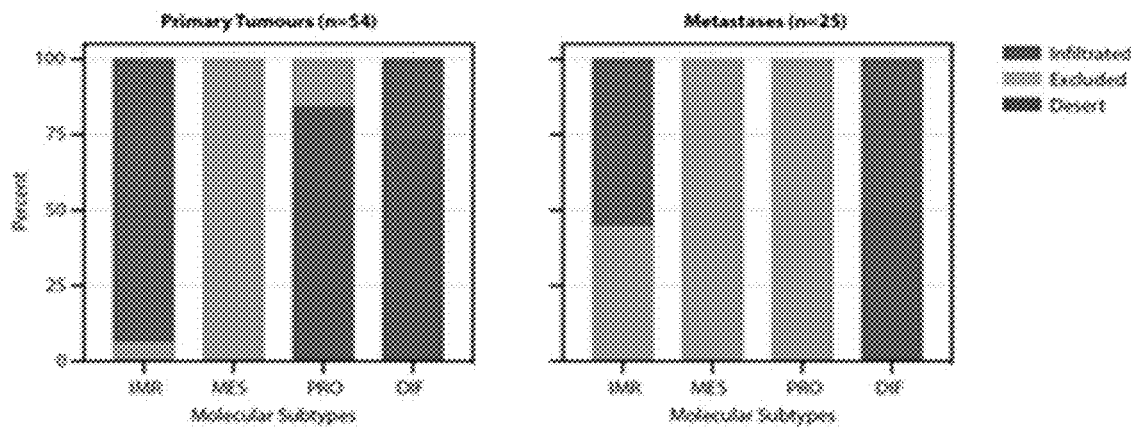
Figures 11A, 11B, 11C:
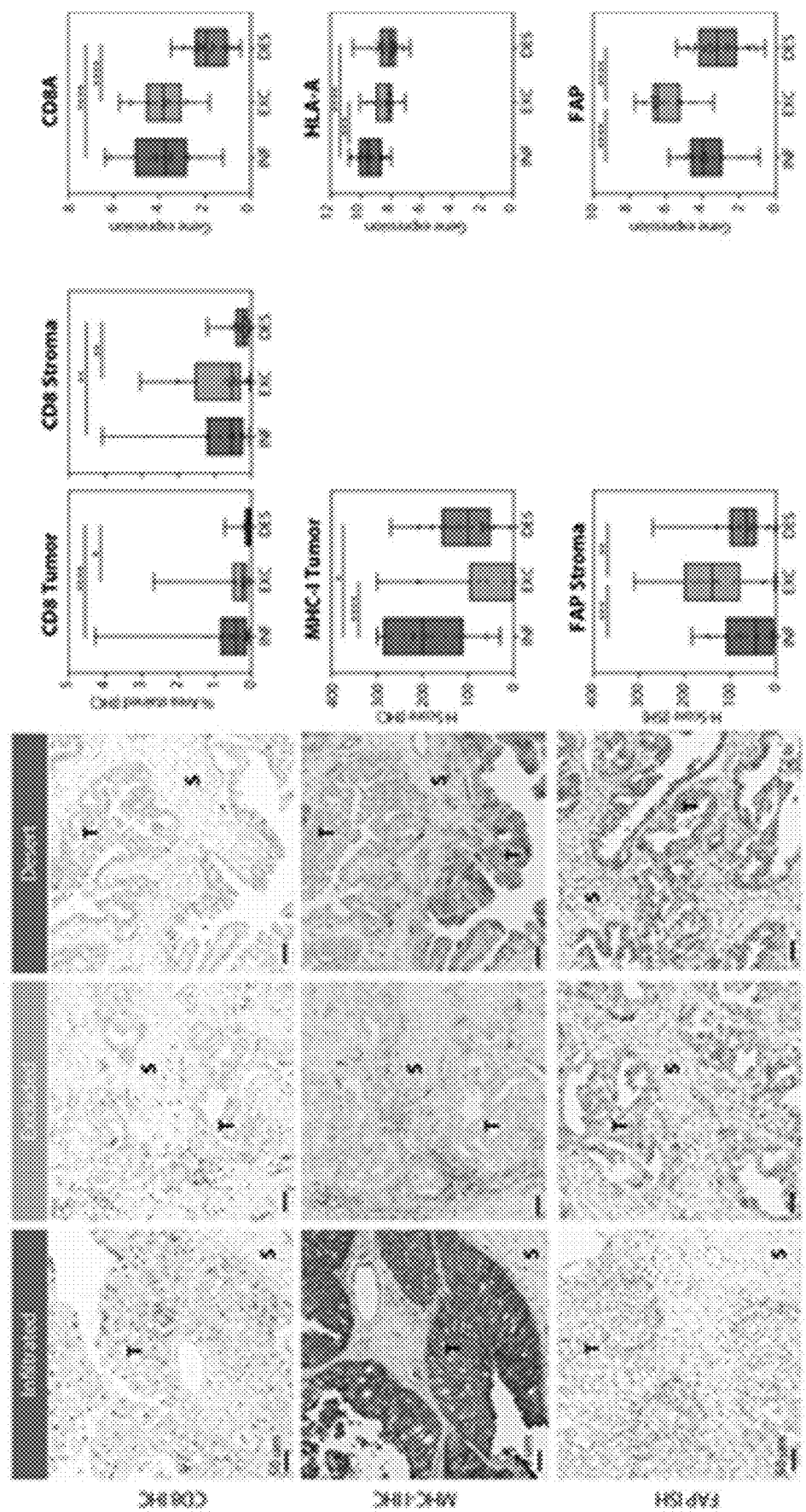
FIGS. 11a-11c show exemplary in situ validation of molecular features associated with the predicted tumor-immune phenotypes.

IV.D. Identifying Pathways and Cell Features of Phenotype Using Machine-Learning Approach Integrated digital pathology and transcriptional analysis can be used to uncover biological pathways and immune features underlying the T cell excluded phenotype, including the upregulation of FAP, a marker of activated stroma and downregulation of antigen presentation genes. To validate these findings and distinguish which cell compartment underwent these molecular changes, in situ analysis was performed on an independent ovarian tumor collection of 84 samples. RNAseq transcriptome analysis was performed on these samples and their tumour-immune phenotypes were predicted based on the 157-gene classifier developed in this study (FIG. 10b-c). FIG. 10c shows stacked bar graphs, where each bar displays the percentage of primary tumors (left, n=54) or metastases (right, n=25) classified as infiltrated, excluded or desert. Unclassified tumors (n=6, including 1 primary and 5 metastases) were excluded from the analysis. CD8 IHC, MHC class I (HLA-A) IHC and FAP ISH analyses were performed on whole slides of these tumor samples. The digital pathology algorithm developed in this study was applied to the CD8 IHC images to quantify the amount and spatial distribution of CD8$^+$ T cells. Representative staining images of these markers from each of the three tumor-immune phenotypes are shown in FIG. 11a. A summary of all IHC or ISH scores for all samples is shown in FIG. 11b. Specifically, FIG. 11b shows the percentage of CD8 staining over tumor/stroma area, H-scores for MHC-I, and FAP expression in the tumor or the stroma were presented by the three-class tumor-immune phenotypes.

Figure 10D:
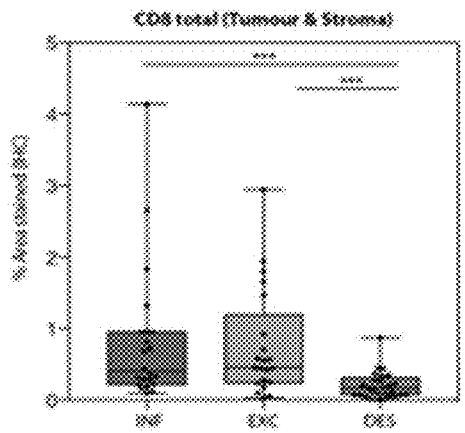

Consistent with the findings from the ICON7 dataset, infiltrated and excluded tumor-immune phenotypes have similar abundant quantities of CD8$^+$ T cells by in situ analysis (FIG. 10d), and similar CD8 mRNA expression levels by RNAseq (FIG. 11c, top). In FIGS. 10d and 11c, the statistical significance is displayed as *p<0.05, p<0.01, *p<0.001, ****p<0.0001 by ANOVA analysis. However, they differed in their distribution patterns in the tumor epithelium vs. stroma area with a lower frequency of CD8$^+$ cells found in the tumor epithelium of excluded tumors (FIG. 11a, top). Furthermore, HLA-A IHC analysis confirmed that the downregulation of HLA-A was associated with the excluded and a subset of desert tumors (FIG. 11b, middle row), while FAP ISH analyses showed a strong enrichment in the excluded tumors (FIG. 811b, bottom row). These findings were consistent with the results from the RNAseq transcriptome analysis (FIG. 11c). In FIG. 11c, RNAseq gene expression levels, represented as Log$_2$(RPKM+1) for CD8A, HLA-A and FAP, are presented across the three-class tumor-immune phenotypes. The box-whisker plots show the median with interquartile range. Each dot represents a tumor sample (primary tumors and metastases are pooled).

Further, these in situ analyses identified specific cell compartments contributing to these observed modulations. For example, the downregulation of MHC class I in the excluded tumors was restricted to the tumor compartment. In contrast, the infiltrated tumors exhibited strong and homogenous MHC class I staining on tumor cells. On the other hand, the desert tumors exhibited both intra-tumor and inter-tumor heterogeneity in MHC class I expression. This heterogeneity was reflected by an intermediate H-Scores for MHC class I in the tumor epithelium (FIG. 11b). Together, these findings provided additional insights into potential mechanisms mediating immune exclusion, which may involve extensive crosstalk between the tumor, stroma and immune compartments.

IV.E. MHC Class I Expression: Regulated via DNA Methylation and Downregulated by TGF in Ovarian Cancer Cells Assessments were performed to determine the mechanism of downregulation of MHC class I expression in the ovarian tumor cells. Defects of antigen presentation machinery in tumor cells by downregulation of MHC class I expression via genetic mutations or epigenetic suppression have been shown to represent an important mechanism of immune escape in multiple cancers ENREF 23. The detection of somatic mutations in the HLA genes has been previously studied in different TCGA cohorts including the ovarian cohort. Unlike colon and head and neck cancer, mutations in HLA genes are rare in ovarian cancer samples, indicating loss of MHC-I is not likely due to genetic mutations.

Figures 12A, 12B, 12C, 12D:
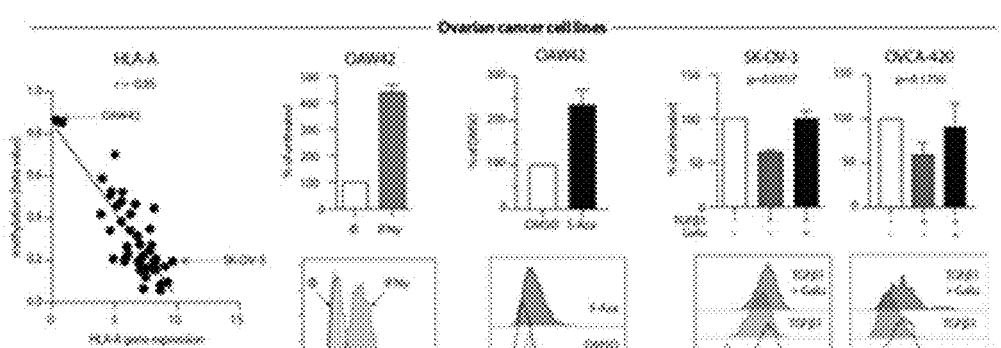
FIGS. 12a-12k show exemplary results and predictions relating MHC class I expression and epigenetic regulation and characterizing a multi-faceted role of TGFβ on ovarian cancer cells and fibroblasts.

Further assessments were performed to determine whether the loss of MHC class I expression is due to epigenetic regulation. To specifically detect the methylation on tumor cells, DNA methylation profiles were generated for a panel of 48 ovarian cancer cell lines using the Infinium Human Methylation 450K Chip. A strong anti-correlation was observed between the methylation level of the promoter region of the HLA-A gene (beta value) and its expression level (Log$_2$(RPKM+1)) (FIG. 12a), suggesting that down-regulation of HLA-A expression in ovarian cancer is likely mediated via an epigenetic mechanism. Indeed, this hypothesis is further supported by multiple additional lines of evidences. The observed MHC-I downregulation in ovarian cancer cells is reversible. Ovarian cancer cell lines with hypermethylation/MHC-I$^{low}$ (OAW42 and PA-1) or hypomethylation/MHC-I$^{high}$ (SK-OV-3 and OVCA-420) treated with IFNγ, a cytokine well established for inducing MHC-I expression[29,30], showed increased MHC class I protein expression on the tumor cell surface (FIGS. 12b and 13a), supporting a reversible epigenetic mechanism rather than a hard-wired irreversible genetic modulation for MHC class I expression. FIG. 12b shows expression of surface MHC-I (HLA-ABC antibodies) after IFNγ treatment as analyzed on the MHC-I$^{low}$-OAW42 ovarian cancer cell line by flow cytometry. The top plot of FIG. 12b and of FIG. 13a includes box plots that display the percentage of change compared to untreated cells for 2 experiments. The bottom plot of FIG. 12b and of 13a shows a flow cytometry image from one experiment, where the left shaded distribution corresponds to the isotype control, the black line corresponds to untreated cells, and the right shaded distribution corresponds to IFNγ-treated cells.

More specifically, in ovarian cancer cell lines with hyper-methylation of HLA-A promoter, treatment with demethylating agent 5-aza-2'-deoxycytidine, a DNA methyltransferase (DNMT) inhibitor, was shown to be able to significantly induce the expression of MHC class I protein at the tumor cell surface (FIG. 12c, FIG. 13b). The top graph of FIG. 12c and of FIG. 13b corresponds to a pool of three experiments, and the bottom graph of FIG. 12c and of FIG. 13b corresponds to a flow cytometry image from one representative experiment. Cells corresponding to FIG. 13b are from the MHC-I$^{low}$ PA-1 ovarian cancer cell line and were treated with the DNA methylation inhibitor 5-Aza-2'-Deoxycytidine (1 μM) or its DMSO control. Lastly, a previous study has shown that a subset of cancers harbouring mutations in the SWI/SNF ATPase, SMARCA4, is sensitive to EZH2 inhibition. Indeed, two ovarian cancer cell lines with SMARCA4 mutations, COV434 and TOV112D, showed increased HLA-A expression upon treatment with the EZH2-targeting histone methyltransferase inhibitor, 5 μM EZH2 inhibitor (EZH-6438) (FIG. 13c) relative to control DMSO. Collectively, these results indicated that epigenetic regulation may represent one of the important mechanisms of downregulating antigen presentation in ovarian cancer cells to promote immune escape.

Parallel to the downregulation of MHC-I in tumor cells, another primary feature of the excluded tumors is the upregulation of TGFβ/reactive stroma genes. TGFβ has been shown to downregulate MHC class I on uveal melanoma cells in vitro and TGFβ1 null mice exhibited an aberrant expression of MHC-I and MHC-II in tissues. To determine whether TGFβ might play a direct role in down-regulation of the expression of MHC class I on ovarian tumor cell, two MHC-I$^{high}$-expressing ovarian cancer cell lines were treated with TGFβ1. Flow cytometry analysis revealed that TGFβ1 decreased the surface expression of MHC-I by 37, 7±3.2% in SK-OV-3 and 40.45±14.2% in OVCA-420 compared to the untreated cells. Further, in the presence of Galunisertib, a small molecule TGFβ inhibitor targeting the TGFβRI, MHC class I expression was restored to the untreated level (FIG. 12d). The top graph of FIG. 12d shows the percentage of change compared to untreated cells, pooling over 3 experiments. The bottom graph of FIG. 12d shows the flow cytometry image of HLA-A,B,C of one representative experiment is shown. The bottom distribution in the bottom plot of FIG. 12d corresponds to the isotype control, the black line corresponds to a distribution for untreated cells, the second-to-top distribution in the bottom plot of FIG. 12d corresponds to TGFβ1-treated cells, and the top distribution in the bottom plot of FIG. 12d corresponds to TGFβ1+Galunisertib-treated cells. For each graph, mean with SD is shown. A Kruskal-Wallis was run and the p-values are shown.

Figures 12E, 12F, 12G, 12H, 12I:
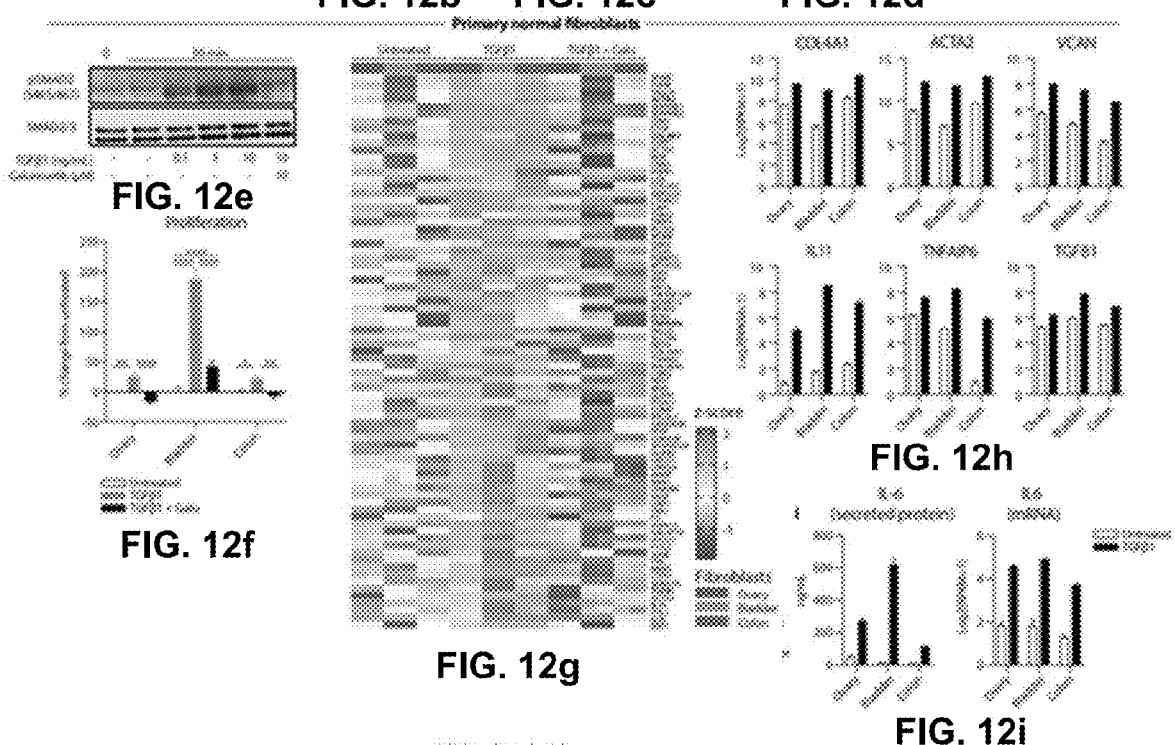

IV.F. TGF Induces ECM Production and an Immunosuppressive Milieu in Ovarian Tumor Stroma In addition to loss of MHC class I expression on tumor cells, other features associated with the T cell excluded tumors include enriched TGFβ expression and signaling (FIG. 8d), as well as enriched representations of fibroblasts and stroma components (FIG. 8e). To further evaluate if TGFβ has a specific role in modulating fibroblasts to promote T cell exclusion, transcriptional responses specifically induced by TGFβ treatment were analyzed in primary human fibroblasts from normal ovaries, bladder and colon. The TGFβ pathway was activated, as indicated by increased phosphorylation level of SMAD2/3 in a TGFβ dose-dependent manner and pathway inhibition by Galunisertib treatment (FIG. 12e). TGFβ treatment promoted proliferation of these primary human fibroblasts (FIG. 12f). FIG. 12f shows the percentage of change of induced proliferation compared to untreated cells. The graphs display three replicates, with mean and standard-deviation statistics indicate. Further, a common 77-gene transcriptional program specifically induced by TGFβ treatment in these human primary fibroblasts (FIGS. 12g and 13d). This transcriptional program consists of various ECM-related genes including collagens (COL4A4, COL4A2, COL16A1), ECM glycoproteins (CTGF, TGFBI, SPARC), proteoglycans (BGN, DCN, VCAN), as well as reactive stroma markers (ACTA2, TNC, LOX, TIMP3) (FIGS. 12g and 12h). FIG. 12g includes a heatmap summarizing the top 77 genes specifically induced by TGFβ treatment across three primary human fibroblasts cells from different tissues. FIG. 12h identifies examples of genes upregulated by TGFβ1 for the normal ovarian, bladder and colon fibroblasts. These findings suggest that TGFβ may mediate T cell exclusion, at least in part, by creating a physical barrier via activating fibroblasts and promoting dense ECM production.

In addition, the data also suggests that TGFβ may contribute to an overall immunosuppressive tumor microenvironment in the T cell excluded tumors. Supporting this notion, TGFβ specifically induced the expression of several immune-modulatory molecules in the fibroblast cells, including tumor promoting cytokines, IL11, and TNFAIP6, a potent anti-inflammatory molecule previously reported to inhibit the recruitment of neutrophils and shift pro-inflammatory vs. anti-inflammatory protein profiles in macrophages to elicit immune suppression (FIG. 12g). Furthermore, IL6, another cytokine with immunosuppressive activity, was also modulated directly by TGFβ. TGFβ treatment not only specifically induced the mRNA expression of IL6 in human fibroblasts, it also dramatically increased IL-6 protein secretion level in the supernatant (FIG. 12i). FIG. 12i displays duplicates and identifies mean and standard-deviation statistics.

Figure 12J:
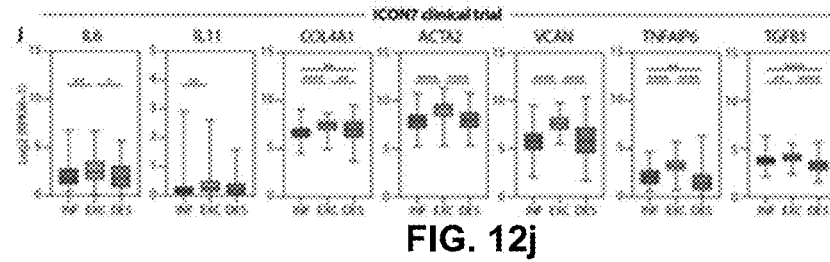
Figure 12K:
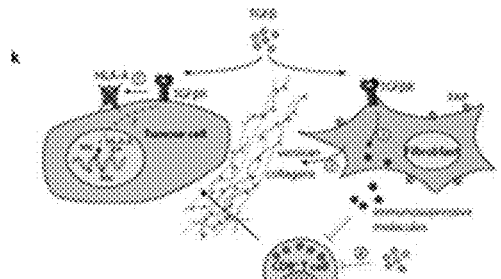

Finally, supporting the findings from the in vitro studies, the data indicates that many of the TGFβ induced ECM and immune-modulatory genes in vitro, were also specifically enriched in the T cell excluded tumors in the ICON7 dataset (FIG. 12j). In FIG. 12j, the box-whisker plots show the min to max. The statistical significance is displayed as *p<0.05, p<0.01, *p<0.001, ****p<0.0001 by one-way ordinary ANOVA with Tukey's multiple comparison test. Collectively, the data illuminated a multi-faceted role of TGFβ in mediating consequential crosstalk between tumor cells and cancer associated fibroblasts to shape the tumor-immune contexture in the tumor microenvironment as summarized by the model presented in FIG. 12k. More specifically, the data supports a hypothesis of TGF having multi-faceted roles, including: (1) downregulation MHC-1 expression in tumor cells; (2) inducing a dense matrix and physical barrier impeding T cells infiltration; (3) inducing immuno-suppressive milieu; and (4) inducing CD8 T cell exhaustion.

IV.G. Anti-TGFβ Enhances Anti-Tumor Activity in Combination with PD-L1 in Ovarian Cancer Mouser Model Thus, TGFβ may have a central role in mediating CD8$^+$ T cell exclusion and immune suppression in ovarian cancer. To determine whether blocking TGFβ signaling can provide synergy to checkpoint inhibitors in ovarian cancer mouse model, immunocompetent mice subcutaneously implanted with BrKrasX1.3 ovarian cancer cells were treated (approximately 13 days after tumor inoculation) with the isotype control, anti-PD-L1, anti-TGFβ or a combination of anti-PD-L1 and anti-TGFβ antibodies according to the schedule shown in FIG. 14a. Anti-TGFβ alone showed no anti-tumor activities. Anti-PD-L1 alone showed a modest efficacy in this model with 2.9% (1/34) of complete responses (CR) and 11.8% (4/34) of mice with a partial regression (PR) or a stable tumor (SD) that finally progressed. In contrast, the combination of anti-PD-L1 and anti-TGFβ significantly enhanced the anti-tumor activities to 20.5% (7/34) of complete responses and 23.5% (8/34) of mice with a partial regression or stable tumor before they progressed (FIG. 14b). FIG. 14b shows the tumor volume for each mouse over the time in each group: isotype control, anti-PD-L1, anti-TGFβ and anti-PD-L1+anti-TGFβ combination from left to right respectively. The x-axis represents the days on treatment with day 1 for the first dose. Each line represents a mouse. The graph displays a pool of four experiments with 7-10 mice per group for each experiment (n=34/group). The percentage of complete responses (CR) and Partial regression (PR) or Stable tumors (SD) are annotated on each graph and defined in the Methods section. The combination treatment also yielded a significantly improved survival in mice comparing to each single agent treatment alone (FIG. 14c). FIG. 14c depicts the survival of mice for the pool of 4 experiments. The statistical significance is tested by Log-rank Mantel-Cox test.

To further investigate the underlying mechanisms of action, pharmacodynamic changes of anti-TGFß, anti-PD-L1, alone or in combination were characterized in the BrKrasX1.3 ovarian cancer mouse model at day 8 post the initiation of the treatment, while no difference of tumor mass was noticeable between the groups (FIG. 14d). The inhibition of the TGFß signaling pathway upon treatment with anti-TGFß alone or in combination with anti-PD-L1 was confirmed by demonstrating significantly decreased levels of phospho-SMAD2 by IHC (FIG. 14e, left panel and FIG.

Figure 15A:
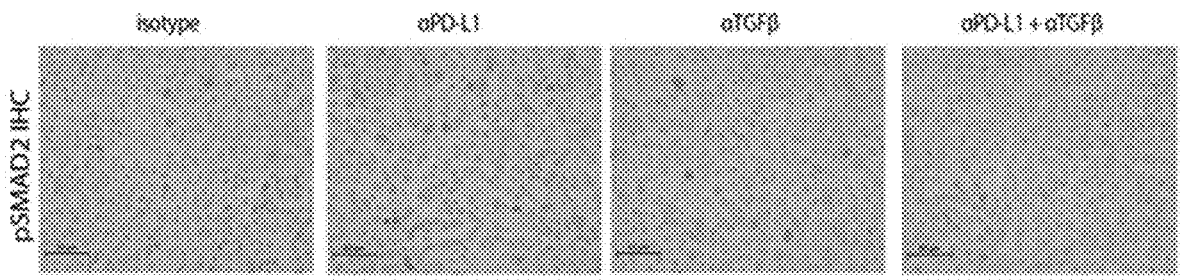
FIGS. 15a-15c show exemplary results of digital pathology analysis performed for pSMAD2 and CD8 IHC in mouse tumors.
Figure 16A:
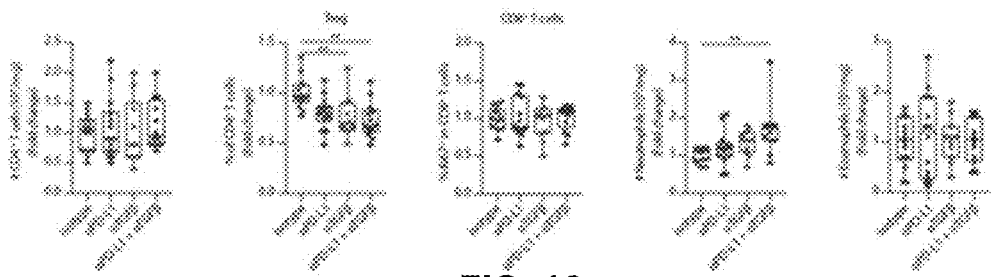
FIGS. 16a-16d show exemplary results of flow cytometry analyses performed to study the immune infiltrate in mouse tumors after treatment.
Figure 16B:
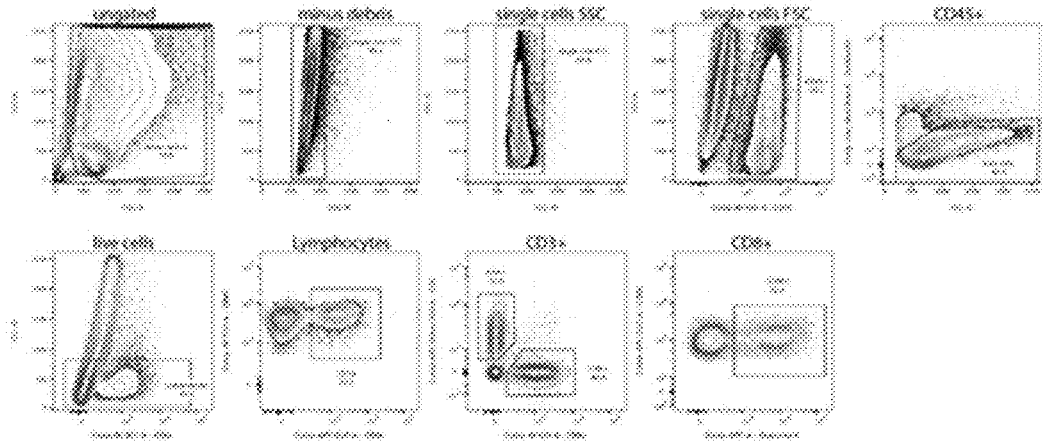
Figure 16C:
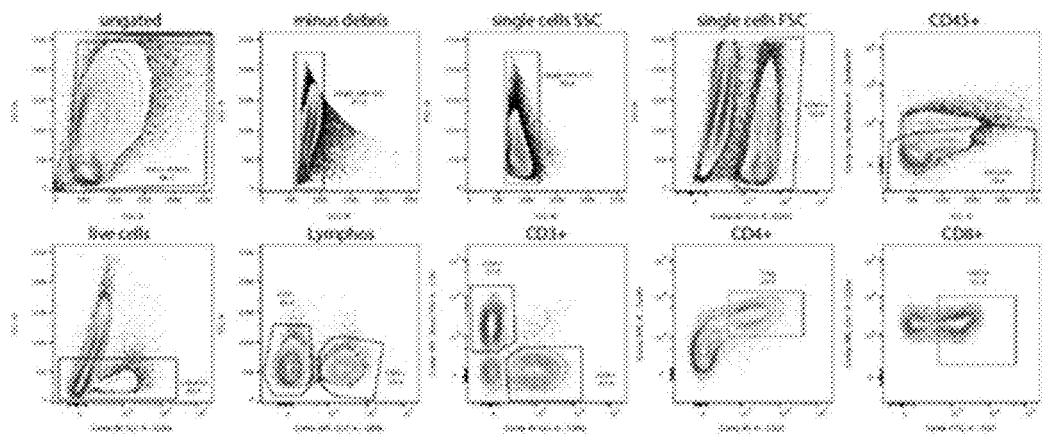
Figure 16D:
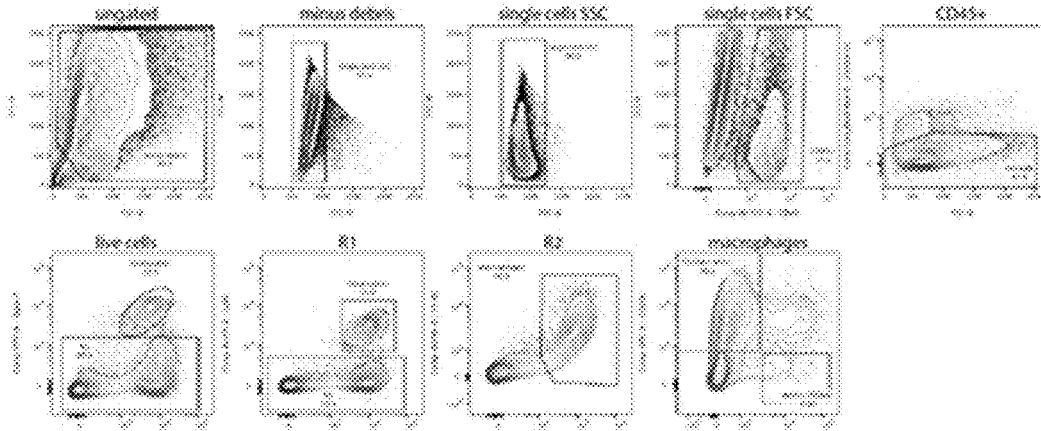

15a). Data shown in FIG. 14e was generated by pooling two experiments and identifying the fold change relative to the mean of the isotype group for each experiment depicted (n=15-16/group). FIG. 15a shows representative images for pSMAD2 IHC in all 4 treatment groups. A digital pathology algorithm was applied to quantify the changes in $CD8^+$ T cell density within the viable tumor tissues (excluding necrotic and stromal areas) based on CD8 IHC staining (FIG. 14f). FIG. 14f shows representative images of the digital analysis for CD8 IHC of one experiment with (left) digital mask, (middle) CD8 IHC on the whole slide and (right) high magnification of Field Of View (FOV) picked based on the mean density of the total slide. A trend of increased $CD8^+$ T cell density upon anti-TGFß/anti-PD-L1 combination treatment was observed (FIG. 14e, right panel). Consistent with the histological findings, flow cytometry analysis (conducted for another set of 3 experiments, with 10-14 mice per group) also demonstrated a trend of increased $CD8^+$ T cells density and T cell function (Granzyme B) in the mouse tumor tissues upon anti-TGFß/anti-PD-L1 combination treatment (FIG. 14g). Additional flow cytometry analyses further suggested a remodeling of the mouse tumor microenvironment to a more pro-inflammatory state upon anti-TGFß and anti-PD-L1 treatment. Indeed, the frequency of $iNOS^+$ macrophages (M1-like) was increased, accompanied by a significant decreased of $CD206^+$ macrophages (M2-like) in the mouse tumors treated with anti-TGFß/anti-PD-L1 combination, while the relative number of macrophages was unchanged (FIG. 14h-i). In addition, the levels of CXCL9 and CXCL10, both potent T cell chemoattractant, were significantly elevated in the serum of mice treated with anti-PD-L1/anti-TGFß combination, while CXCL9 was also elevated in the group treated with anti-PD-L1 alone (FIG. 14j). The statistical significance is displayed as *$p<0.05$, $p<0.01$, *$p<0.001$, ****$p<0.0001$ calculated with a Kruskal-Wallis test with Dunn's multiple comparison test. FIG. 16a-d show results of flow cytometry analyses to study the immune infiltrate in mouse tumors after treatment. FIG. 16a presents flow cytometry data for additional cell types/function from mouse tumors treated with isotype control, anti-PD-L1, anti-TGFβ alone or in combination. FIGS. 16b-d present a gating strategy to analyze flow cytometry experiments for the analysis of granzyme B among CD8+ T cells (FIG. 16b), the identification of regulatory T cells and Ki-67 expression (FIG. 16c), and the expression of CD206 and iNOS among macrophages (FIG. 16d).

Collectively, these results provided pre-clinical proof of concept and potential mechanisms of action for targeting the TGFβ pathway as a novel therapeutic strategy to overcome T cell exclusion and immune suppression, and ultimately improve the patient response to cancer immunotherapy.

IV.H. Interpretations

In the present embodiments, a novel digital image analysis algorithm was developed to quantify the quantity and spatial distribution of $CD8^+$ T cells in the tumor microenvironment. Coupling this digital pathology algorithm with transcriptome analysis in a large cohort of archival tumor tissues from the ICON7 Phase III clinical trial, a random forest machine learning algorithm was built to classify tumor-immune phenotypes in ovarian cancer. This approach yielded a set of high-dimensional quantitative metrics to define tumor-immune phenotypes. The described Example provides the first proof of concept of classifying tumor-immune phenotypes based on a gene expression classifier. The novel approach developed in this study may enable systematic characterization of tumor-immune phenotypes in large clinical trials and translational studies, in which availability of CD8 IHC image analysis are often limited. With additional validation and optimization, the molecular classifier developed in this study may be widely applicable to classify tumor-immune phenotypes in other solid tumor types.

Although a computational framework, Tumor Immune Dysfunction and Exclusion (TIDE), can be used to identify factors that predict cancer immunotherapy response. The study represents the first study to integrate digital pathology and machine learning and provide a systematic characterization of molecular features defining distinct tumor-immune phenotypes in human cancer. One conclusion is that tumor-immune phenotypes should be studied and interpreted in the context of disease biology. For example, the immune desert tumors in ovarian cancer are heterogeneous and comprise of two distinct molecular subtypes, the differentiated and the proliferative subtype, which are associated with different clinical outcomes in ICON7 study (FIG. 5f) as well as in previously published ovarian cancer studies. Thus, relying merely potential over-simplified classification of TIL+ and TIL− tumor would result in lumping tumors with distinct biology lumped together.

Using immunohistochemistry and sequence data also facilitated a discovery of two hallmark features characterizing the T cell excluded tumors, including 1) loss of antigen presentation on tumor cells and 2) upregulation of TGFβ and stromal activation. Further, this study further dissected the functional role of TGFβ in mediating T cell exclusion and immune suppression in ovarian cancers.

Figure 17:
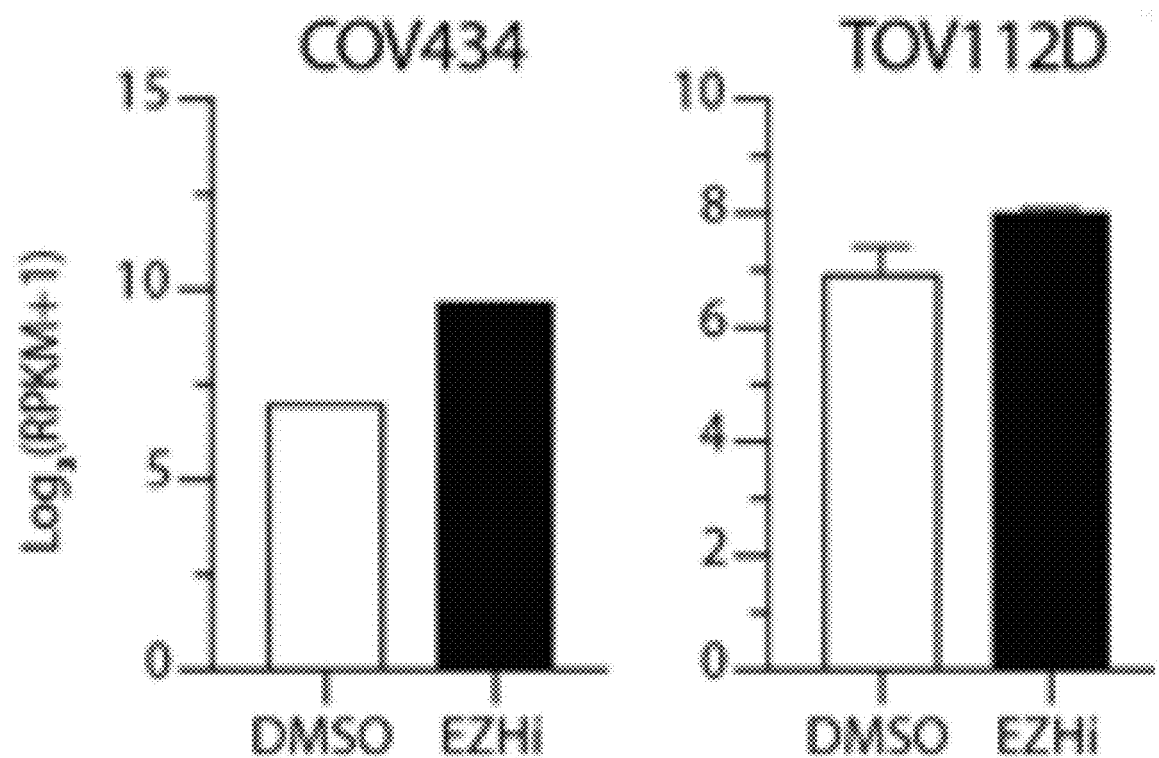
FIG. 17 shows the HLA-A expression for two ovarian cancer cell lines with SMARCA4 mutations following treatment with a DMSO control solvent or an EZH inhibitor.

The data revealed that the downregulation of MHC class I in ovarian cancer cells may be regulated by epigenetic mechanisms. Supporting this finding, there was a strong anti-correlation between the HLA-A gene expression and promoter methylation levels. Further, IFNγ treatment as well as EZH2 or DNMT inhibition may overcome such epigenetic regulation and increase HLA-A expression in selected ovarian cancer cells. For example, a previous study has shown that a subset of cancers harbouring mutations in the SWI/SNF ATPase, SMARCA4, is sensitive to EZH2 inhibition. Indeed, as shown in FIG. 17, for each of two ovarian cancer cell lines with SMARCA4 mutations, COV434 and TOV112D, increased HLA-A expression (as characterized by the log of the sum of Reads Per Kilobase of transcript, per Million mapped reads (RPKM) was observed following treatment with the EZH2-targeting histone methyltransferase inhibitor, EPZ-6438 relative to treatment with a control solvent DMSO.

Further, loss of MHC-I expression regulated by epigenetic mechanisms as a result of immune pressure associated with an absence of $CD8^+$ T cell infiltration in relapsing tumors has been previously reported in two patients with metastatic Merkel cell carcinoma treated with antigen-specific $CD8^+$ T cells and immune checkpoint inhibitors. In vitro treatment of the primary tumor cells with 5-Aza may be used to restore the expression of the MHC-I haplotype lost. In addition, TGFβ may play a specific role in the downregulation of tumor MHC class I expression. TGFβ1 treatment decreased the surface expression of MHC class I of hypomethylated ovarian cancer cells, while TGFβ inhibition restored its normal expression level.

Secondly, the study identified another important role of TGFβ in mediating crosstalk with cancer stromal cells to promote T cell exclusion and immunosuppression. Using human primary fibroblasts as model systems, TGFβ treatment specifically activated fibroblasts and promoted the production of ECM, which may serve as a physical barrier hindering T cell infiltration. Furthermore, the data also suggests that TGFβ may contribute to an overall immunosuppressive tumor microenvironment in the T cell excluded tumors. TGFβ1 treatment specifically induced immunemodulatory molecules, such as IL6, IL11 and TNFAIP6 in human primary fibroblasts. Secreted in inflammatory conditions, TNFAIP6 has been reported to inhibit neutrophil migration via binding hyaluronan molecules expressed in the tumor microenvironment. Moreover, TNFAIP6 promotes the anti-inflammatory phenotype of macrophages (M2-like) thereby contributing to the immunosuppression.

Finally, TGFβ is associated with lack of response to anti-PD-L1 therapy in bladder cancer, especially within the T cell excluded tumors. To further assess the therapeutic potential of targeting TGFβ in ovarian cancer, tumor-bearing mice were treated with anti-PD-L1 and anti-TGFβ. Synergistic anti-tumor responses were confirmed in an immunocompetent mouse model of ovarian cancer. (To obtain the ovarian cancer mouse model, the BrKras (Brca1–/–; p53–/–; myc; Kras-G12D; Akt-myr) ovarian cancer cell line was obtained, and a tumor cell line was derived by one passage into FVB syngeneic immunocompetent mice. The subsequent BrKrasX1.3 cell line was subcutaneously implanted in FVB mice as an ovarian cancer immunocompetent mouse model.) Mechanistic studies also supported the hypothesis that TGFβ played an important role in promoting T cell exclusion and immune suppression. Both histological and flow cytometry analysis demonstrated a consistent trend of increased CD8$^+$ T cell presence in the mouse tumor tissues upon anti-TGFβ and anti-PD-L1 combination treatment. Blocking TGFβ signaling synergized with anti-PD-L1 and significantly remodelled the mouse tumor microenvironment to a more pro-inflammatory state, including increased M1-like and decreased M2-like macrophages, increased levels of T cell chemoattractant, CXCL9 and CXCL10, and increased density of cytotoxic T cells (GZMB$^+$CD8$^+$). Blocking TGFβ and PD-L1 signaling pathways triggered a strong T cell infiltration in the tumor core and enhanced tumor regressions and survival.

Disclosures herein may have important clinical significance in the field of cancer immunotherapies. Checkpoint blockades have demonstrated impressive efficacy in only subsets of patients with a pre-existing T cell immunity, with the response rate is even lower in ovarian cancer even lower. Therefore, there is a strong unmet need to further broaden and deepen the clinical efficacy of the immune checkpoint inhibitors, and TGFβ is an attractive target to overcome the immune escape mechanisms involved in the T cell excluded tumors.

In summary, the present embodiments comprise and provide the first systematic and in-depth characterization of the molecular features and mechanisms underlying the tumor-immune phenotypes in human cancer. Integrating digital pathology with machine learning and transcriptome analysis can identify mechanisms by which tumor cells and cancer-associated fibroblasts interact to shape the tumor-immune contexture in the tumor microenvironment. Further, methods for targeting the TGFβ pathway can be used as a novel therapeutic strategy to overcome T cell exclusion and immune suppression, and ultimately improve the response to cancer immunotherapy.

IV.I. Methods for Example
IV.I.1. Specimens and Cohorts

Three hundred seventy treatment naïve patient samples with High Grade Serous Carcinoma (HGSC) were collected from the phase III ICON7 clinical trial. The tumor tissues were subjected to review by a pathologist to confirm diagnosis and tumor content. The cohort was divided into 2 sample sets for the present study: training set (n=155) and testing set (n=215). An independent validation collection (n=84 including 55 primary tumors and 29 paired metastases) was procured from Cureline, Inc (Brisbane, CA, US). All procured and clinical samples had an appropriate Institutional Review Board (IRB) approval. The ovarian cancer cell lines were obtained from the Genentech Cell Bank where they were authenticated by short tandem repeat profiling prior to banking and SNP fingerprinting after expansion. The human primary normal fibroblasts CCD-18-Co (colon, CRL-1459™; ATCC, Manassas, VA), HOF (ovary, #7336; ScienCell Research Laboratories, Carlsbad, CA) and Primary human bladder fibroblast (PHBF) (bladder, PCS-420-013™; ATCC) were procured from ATCC for in vitro TGFβ1 treatment.

IV.I.2. Immunohistochemistry and in Situ Hybridization Assays

Immunohistochemistry (IHC) and in situ hybridization (ISH) assays were performed on 4-μm FFPE tissue section. MHC-I IHC staining was performed as a single batch on the Ventana Discovery XT platform using the primary antibodies specific for HLA-A proteins (Abcam #ab52922, Clone EP1395Y, diluted at 0.05 μg/mL), the secondary anti-rabbit HRP antibodies and a haematoxylin counter-stain. CD8 IHC was performed at Histogenex on Ventana Benchmark using C8/clone 144B anti-CD8a monoclonal antibodies. Singleplex FAP RNAscope in situ hybridization (ISH) assay was performed. The RNAscope signal was scored on the basis of number of dots per cell as follow 0: 0 dot/cell, 1: 1-3 dots/cell, 2: 4-9 dots/cell, 3: 10-15 dots/cell, and 4: >15 dots/cell with >10% of dots in clusters. To evaluate heterogeneity in marker expression, H-score analysis was performed on FAP-ISH and MHC-I IHC. The H-score was calculated by adding up the percentage of cells in each scoring category multiplied by the corresponding score, resulting in scores are on a scale of 0-400.

IV.I.3. Digital Pathology

The CD8-DAB IHC slides with a haematoxylin counterstain were scanned at 20× magnification on a Panoramic 250 scanner (3DHistech) in MIRAX file format with 80% jpeg compression. Software was used to design an algorithm to distinguish cells of the tumor epithelium from those of the stroma, using cell nuclei shape and size based on the haematoxylin signal. Once the tumor cells were identified, the immediate region surrounding those cells was defined as 'tumor compartment' and the rest as 'stroma compartment'. Within those areas, DAB$^+$ CD8 cells were counted, and the number of CD8$^+$ cells per region classified as 'tumor compartment', or 'stromal compartment' was reported as 'tumor CD8 density', or 'stroma CD8 density' respectively.

Bulk RNA Sequencing

Macrodissection was performed on 370 formalin-fixed, paraffin-embedded (FFPE) tumor tissues from ICON7 as well as 84 FFPE tissues from Cureline, Inc. to enrich tumor percentage to greater than 70%. Total RNA was purified using High Pure FFPE RNA Micro Kit (Roche Diagnostics). RNA sequencing was performed using TruSeq RNA Access technology (Illumina®). RNA-seq reads were first aligned to ribosomal RNA sequences to remove ribosomal reads. The remaining reads were aligned to the human reference genome (NCBI Build 38) using GSNAP[43,44] version 2013-10-10. To quantify gene expression levels, the number of reads mapped to the exons of each RefSeq gene was calculated using the functionality provided by the R/Bioconductor package GenomicAlignments[45]. Raw counts were first converted to counts per million (cpm), filtered for lowly expressed genes (i.e. expressed in less than 10% of samples, and cpm <0.25), then normalized using TMM normalization in the edgeR package followed by voom transformation using the limma package. Principal component analysis (PCA) was used to assess and remove any sample outliers. These normalized log 2 counts were used for downstream analysis.

IV.I.4. Development of the Gene Expression-Based Molecular Classifier

Random Forest Regression. The scores for $CD8^+$ T cell density in tumor and stroma were found to strongly correlate (cor=0.74). To better capture and quantify the CD8 infiltration patterns, theses CD8 scores were converted into polar coordinates: $CD8^+$ T cell quantity=[squareroot ((CD8-tumor)^2+(CD8-stroma)^2)] and $CD8^+$ T cell spatial distribution=[atan(CD8-stroma/CD8-tumor)]. To identify the genes associated with these two metrics, a random forest regression model was built for each gene (gene~Quantity+Distribution, randomForest package), with standard resampling of patients but no sampling of the variables (Quantity and Distribution). This revealed the specificity of these two metrics in predicting gene expression, for 16944 genes in the dataset. We did not consider the bottom 25% of genes whose expression was not associated with the variables (i.e., average MSE (mean squared error) below 1st quartile). Genes with expression was selected based on the quantity metric (i.e. percent increase in MSE for >3rd quartile, referred to genes associated with CD8 quantity) and/or by CD8 spatial distribution (i.e., percent increase in MSE for spatial distribution >3rd quartile). This resulted in 103 genes associated with CD8 quantity, 56 associated with CD8 spatial distribution and 193 genes common for these two metrics. Correlation analysis of these genes highlighted very similar transcriptional profiles for the 103+193 genes associated with CD8 quantity. Subsequent analyses, were focused to the genes specific for these two metrics: 56+103=159 CD8-associated genes.

Consensus clustering. Based on the 157 CD8-associated genes (excluding two genes without gene symbol), a consensus clustering was performed on the ICON7 training set (n=155) using the ConsensusClusterPlus R package with pearson distance metric and k-means clustering with 80% patient selection and 100% feature selection. Transcriptional heterogeneity was captured well with 4 clusters, yet those clusters were mostly differentiated by CD8 quantity. To additionally capture CD8 distribution, we set the optimal number of clusters to 6, which differentiated tumors by both CD8 quantity and distribution. The expression profile of the 6 clusters revealed that some clusters only differed in their cytotoxic activity, i.e., level of CD8 quantity (FIG. 8a). The 6 clusters were reduced to 3 immune phenotypes that optimally reflected the distribution of $CD8^+$ T cells while capturing unique biological features. The immune phenotypes were labeled, "infiltrated", "excluded", and "desert", given their association with low vs. high CD8 quantity, and with $CD8^+$ T cell enrichment in stroma vs. tumor epithelial cells.

PAM classification. The PAMR package in R was used to derive a classifier for the prediction of the three immune phenotypes. This classifier was built on the 157 CD8-associated genes, the number of necessary classifier genes ranging from 157 to 1 was evaluated, and the optimal number of genes i.e. 157 was selected corresponding to a minimal cross-validation error rate at a threshold value of 0.23. A tumor was assigned to an immune phenotype when the probability for that phenotype exceeded 0.7 and was below 0.5 for the other two immune phenotypes. A tumor was otherwise considered unclassifiable.

IV.I.5. Gene Set Enrichment Analysis

The multiGSEA function with the Camera enrichment method in the multiGSEA R package was used for gene set enrichment analysis comparing different immune phenotypes in the full ICON7 collection (n=370), with use of the Hallmark and KEGG gene set collections from the Molecular Signature Database. Immune subset and stromal fraction enrichment analysis for ICON7 samples were done using the online xCell cell types enrichment score tool (http://xcell.ucsfedu/).

IV.I.6. Mutation Analysis in TCGA Dataset

Enrichment of deleterious mutations in 15 homologous recombinant deficiency (HRD) related genes and 4 dMMR genes were evaluated in TCGA-OV samples in different tumor-immune phenotypes. In addition, tumor mutation burden (TMB) and neoantigen loads were estimated in TCGA-OV samples. Enrichment analysis in each tumor-immune phenotype for above-mentioned genetic features in TCGA-OV was performed using Fisher's exact test corrected for multiplicity via Benjamini-Hochberg method in R.

IV.I.7. Molecular Subtyping of Ovarian Tumors

The 100 genes that were reported in the CLOVAR signature were extracted to examine the molecular subtype of a tumor. Four major clusters were identified in the ICON7 cohort based on hierarchical clustering with Euclidean distance and Ward's linkage method. By checking the testing results and up/down pattern in the original report for each gene, the identified clusters were assigned to various molecular subtypes (e.g., Immunoreactive, Mesenchymal, Proliferative and Differentiated).

IV.I.8. Methylation Analysis on Ovarian Cancer Cell Lines 250 ng of genomic DNA from 48 ovarian cancer cell lines were assayed using the Illumina Human Methylation 450 BeadChip platform. The raw methylation data (.idat files) were read into the R software using illuminaio. Quality control was performed using the methylation R package minfi; all samples passed quality control. The methylation levels were normalized using the "noob" background correction and dye bias equalization methods as implemented in minfi. Both procedures have been shown to perform well and to be appropriate for cancer samples. Beta values, defined as ratios of the methylated allele intensity over the total intensity, were calculated for probes targeting CpG sites located between −1000 bp and +1000 bp from the transcription start site of the HLA-A gene.

IV.I.9. In vitro Experiments on Ovarian Cancer Cell Lines and Normal Fibroblasts SK-OV-3 and OVCA-420 (MHC-$I^{high}$), and OAW42 and PA-1 (MHC-$I^{low}$) ovarian cancer lines were cultured in complete culture media (RPMI-1640+10% FBS). The cells were plated at 12,500-100,000 cells/well in 6-well tissue culture plate and complete culture media. After 24 hours, the cells were starved overnight in DMEM high glucose medium without FBS. Next, the starving media was replaced with culture media only (DMEM+2% FBS), 10 ng/mL rhTGFβ1 (Cat #PHG9204, Thermo Fisher, CA), 10 ng/mL rhTGFβ1+10 µM Galunisertib (Cat #S2230, SelleckChem, TX) or 5 ng/mL recombinant IFNγ (Cat #554617, BD Biosciences, CA) for 96 h at 37° C. Cells were then stained and analysed by flow cytometry. The "percentage of untreated" was calculated using this formula: [Geo Mean Fluorescence Intensity (IFNγ-treated cells)/Geo Mean Fluorescence Intensity (untreated cells)]×100. In order to see if MHC-I expression can be regulated by methylation, two MHC-I$^{low}$ lines OAW42 and PA-1 were plated at 250,000-500,000 cells/dish in 10-cm dish and serum starved as described above for TGFβ1 treatment. 10 μM and 1 μM 5-Aza-2'-deoxycytidine (5-Aza, Cat #A2385, Sigma-Aldrich) demethylating agent in culture media was used to treat OAW42 and PA-1, respectively, for 96 h prior to FACS analysis. Media was half-replenished with fresh 5-Aza 48 hours after treatment to keep concentration consistent.

The primary normal fibroblast PHBF (Bladder), CCD-18Co (Colon) and HOF (Ovary) were serum-starved overnight before treatment with media only (untreated), 10 ng/mL rhTGFβ1 or 10 ng/mL rhTGFβ1+10 μM Galunisertib for 24 hours and total RNA was extracted for RNA-seq analysis. To detect IL-6 protein in the supernatant, cells were treated for 48 hours with rhTGFβ1. After the 48 h, the supernatant was collected and analysed by Luminex using the Millipore kit. For the proliferation assay, PHBF, CCD-18Co, HOF were plated at 3,000 cells/well in a 96-well culture flat bottom plate for immunofluorescent assays (Corning, #3917) overnight. Cells were then cultured for 72 hours in DMEM high glucose+1% FBS with indicated concentration of TGFβ1 with or without Galunisertib. Next, CellTiter-Glo® reagents (Promega, G7570) were added to each well and luminescence signal was read with a microplate reader.

IV.I.10. p-SMAD2/3 Western Blot Assay

PHBF cells were plated at 100,000 cells/well in a 24-well cell culture plate overnight, serum starved for 24 h and then cultured in serum-free DMEM with indicated concentration of TGFβ31 with or without Galunisertib for 30 min. Cells were lysed in protein lysis buffer containing T-PER tissue protein extraction reagent (ThermoFisher, #78510), cOmplete™ Protease Inhibitor Cocktail (Sigma-Aldrich, #11697498001) and PhosSTOP™ phosphatase inhibitor cocktails (Sigma-Aldrich, #4906845001). Total protein was diluted and normalized to 0.5 μg/μL with 4×LDS Sample Buffer (ThermoFisher, #84788). 10 ug of total protein was loaded into each well of a NuPAGE 4-12% Bis-Tris Midi Gel (Invitrogen), followed by protein transfer from gel to the membrane using Trans-Blot Turbo (Bio-Rad). The Phospho-Smad2 was first revealed following the general protocol western blot from Bio-Rad. Briefly, the membrane was blocked for 1 h, incubated with Phospho-Smad2 antibodies overnight at 4° C. (Ser456/467, 1:200, Cell Signaling #3108, clone138D4), washed and incubated with secondary antibodies goat anti-rabbit. To analyse the total Smad2/3, the membrane was stripped and then incubated with Smad2/3 antibodies (1:1000, Cell Signaling #8685).

IV.I.11. Flow Cytometry Analysis

Before staining, Fc receptors were blocked for 10 min at room temperature using FcR blocking reagent human (Cat #130-059-901, Miltenyi Biotec, CA). Cells were stained during the blocking step with the LIVE/DEAD™ Fixable Near-IR Dead Cell (Cat #L10119, Invitrogen, CA). Then, cells were incubated at room temperature for 15 min with anti-human HLA-ABC-PE (Cat #560168, BD Biosciences, CA) or isotype control mouse IgG1κ-PE (Cat #556650, BD Biosciences) antibodies, washed and samples were acquired on BD LSRFortessa™ flow cytometer.

IV.I.12. Mouse Samples and Analyses

IV.I.12.a. In vivo Mouse Tumor Experiments

The Genentech Institutional Animal Care and Use Committee (IACUC) approved all animal studies and experiments were conducted according to National Institutes of Health (NIH) guidelines, the Animal Welfare Act, and U.S. Federal law. Female FVB mice were obtained from Jackson Laboratories (stock 001800). All mice were housed at Genentech under specific pathogen-free (SPF) conditions and used at 8-12 weeks of age. Investigators performing mouse experiments were not blinded. The BrKras (Brca1−/−; p53−/−; myc; Kras-G12D; Akt-myr) ovarian cancer cell line was obtained from Sandra Orsulic's lab. The tumor cell line was derived by one passage into FVB syngeneic immunocompetent mice. The subsequent BrKrasX1.3 cell line was selected for this study. Two million of BrKrasX1.3 ovarian cancer cells in 100 μL sterile HBSS were subcutaneously injected in the right flank of FVB mice. When tumors reached a volume of ~50-180 mm$^3$ (about 12 days after inoculation), animals were distributed into treatment groups based on tumor volume to form homogeneous groups at baseline and treated the next day with anti-GP120 isotype control antibodies (mouse IgG1 clone 10E7, 20 mg/kg first dose followed by 15 mg/kg), anti-PD-L1 (mouse IgG1 clone 6E11, 10 mg/kg first dose followed by 5 mg/kg thereafter)+anti-GP120 (10 mg/kg), anti-TGFβ (mouse IgG1 clone 1D11, 10 mg/kg)+anti-GP120 (10 mg/kg first dose followed by 5 mg/kg thereafter), or a combination of anti-PD-L1 (10 mg/kg first dose followed by 5 mg/kg thereafter) with anti-TGFβ (10 mg/kg), 3 times a week for 3 weeks (intravenously for the first dose and intraperitoneally thereafter). Tumors were measured 2-3 times per week by calliper, and tumor volumes were calculated using the modified ellipsoid formula, ½×(length×width$^2$). Complete response (CR) was defined as a complete regression (undetectable) of the tumor without any recurrence. Partial regression (PR) was defined as tumor regression after the last dose for at least two time points followed by uncontrolled tumor growth and stable disease (SD) was defined as at least two time points with stable tumor volumes after the last dose followed by uncontrolled tumor growth. Animals were euthanized immediately if tumor volume exceeded 2000 mm$^3$, or if tumors or body condition ever fell outside the IACUC Guidelines for Tumors in Rodents.

IV.I.12.b. Ex Vivo Analysis on Mouse Tumor Samples

Tumors were collected 7 days after treatment initiation (Day 8). Tumors were weighed, minced in small pieces with a razor blade and transferred into GentleMACS C tube (Miltenyi Biotec) containing 5 mL of digestion media (cocktail of dispase, collagenase P and DNAse I in RPMI+2% FBS). Tumors were first mechanically dissociated by running the program m_imp_tumor02 on the GentleMACS followed by 20 min of incubation at 37° C. on a rotator. Then, the cell suspension is filtered with a 70 μm mesh on a 50 mL falcon containing MACS buffer+2% FBS. Fresh digestion media is added to the undissociated tissue and samples were incubated for another 20 min at 37° C. Next, tissues were mechanically dissociated by running the program m_imp_tumor03 two times. The cell suspension is filtered on the 70 μm mesh. Red blood cells were lysed with ACK buffer. Washed cell suspension were then counted using a Vi-CELL XR (Beckman Coulter, Brea, CA).

For the staining, 4 million of live cells were transferred into FACS tube and washed with FACS stain buffer (1×PBS pH 7.4, 0.2% BSA, 0.09% NaAzide). Cells were then incubated for 10 min at room temperature with FcR blocking reagent mouse (2 μL/tube, Miltenyi Biotec, #130-092-575) and Zombie UV (1 μL/tube, BioLegend, #423108). The cells were then stained with the following antibodies: CD3-APC-Cy7 (2 μg/mL, BD Biosciences, clone 145-2C11, #557596), CD4-Alexa Fluor700 (0.5 μg/mL, BD Biosciences, clone RM4-5, #557956), CD25-PE (1 μg/mL, BD Biosciences, clone PC61, #553866), CD45-BV510 (0.5 μg/mL, BD Biosciences, clone 30F11, #563891), CD8-BV421 (1 μg/mL, BioLegend, clone 53-6.7, #100738), Ly6G-PercP-Cy5,5 (1 µg/mL, BD Biosciences, clone 1A8, #560602), SiglecF-BB515 (1 µg/mL, BD Biosciences, clone E50-2440, #564514), CD11b-BV421 (0.5 µg/mL, BioLegend, clone M1/70, #101236) for 30 min at 4° C. Cells were fixed and permeabilized with BD Cytofix/Cytoperm™ (BD Biosciences, #554714) for 20 min at 4° C. to stain CD206-AlexaFluor647 (2.5 µg/mL, BioLegend, clone C068C2, #141712), iNOS-PE (0.3 µg/mL, Thermo Fisher Scientific, clone CXNFT, #12-5920-82) and GranzymeB-AlexaFluor647 (1 µg/mL, BD Biosciences, clone GB11, #560212). To stain Ki67-FITC (10 µL/test, BD Biosciences, clone B56, #556026) and FOXP3-APC (2 µg/mL, Thermo Fisher Scientific, clone FJK-16s, #17-5773-82), cells were fixed and permeabilized with eBioscience™ Foxp3/Transcription (Thermo Fisher Scientific, #00-5523-00) for 45 min at 4° C.

Flow Cytometry data were collected with a BD LSR-Fortessa X-20 cell analyser and analysed using FlowJo Software (Version 10.4.2, FlowJo, LLC, Ashland, OR).

IV.I.13. Cytokine/Chemokine Profiling

Blood was harvested by terminal heart bleed 7 days after treatment initiation and collected on BD microtainer tubes with serum separator additive (BD biosciences). Tubes were centrifuged for 10 min at 1,000 g at 4° C. and the serum collected and stored at −80° C. until analysis. To profile the cytokines/chemokines present in the serum, the samples were diluted 1:2 in assay diluent (Millipore) and the Mouse Cytokine/Chemokine Immunology Multiplex Assay 32-plex (Millipore) was performed.

IV.I.14. Immunohistochemistry on Mouse Samples

Immunohistochemistry (IHC) was performed on 4 µm thick formalin-fixed, paraffin-embedded tissue sections mounted on glass slides. Staining was performed on the Lab Vision Autostainer (ThermoFisher Scientific, Kalamazoo, Michigan). Sections were de-paraffinized and rehydrated to deionized water. Antigen Retrieval was performed with 1× DAKO Target Retrieval Solution (Agilent Technologies, Carpinteria, CA) for 20 min at 99° C. and cooled to 74° C. Subsequently, endogenous peroxidase was quenched by incubating in sections in 3% H2O2 for 4 minutes at room temperature. Phospho-SMAD2 was detected using a rabbit monoclonal anti-pSMAD2 (clone 138D4, Cell Signal Technologies, Danvers, MA), and a rabbit monoclonal anti-CD8a (clone 1.21E3.1.3, Genentech, Inc, South San Francisco, CA) incubated for 60 min at RT. The primary antibody was detected with PowerVision Poly-HRP anti-Rabbit (LeicaBioSystems, Buffalo Grove, IL) and visualized with a Metal Enhanced DAB chromogen (Thermo Scientific, Kalamazoo, Michigan). Sections were counterstained with Mayer's haematoxylin, dehydrated, mounted with permanent mounting medium, and cover slipped.

IV.I.15. Digital Pathology

Figure 15B:
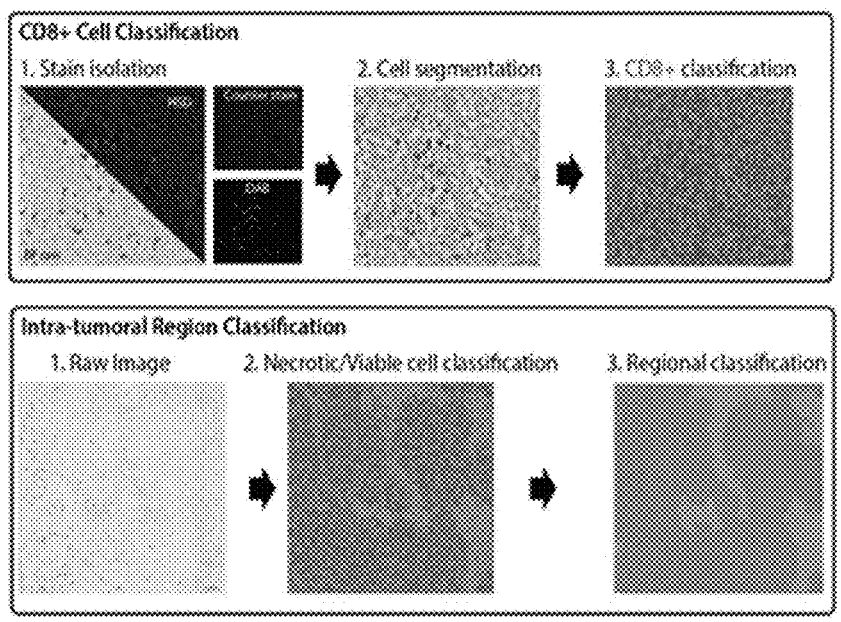
Figure 15C:
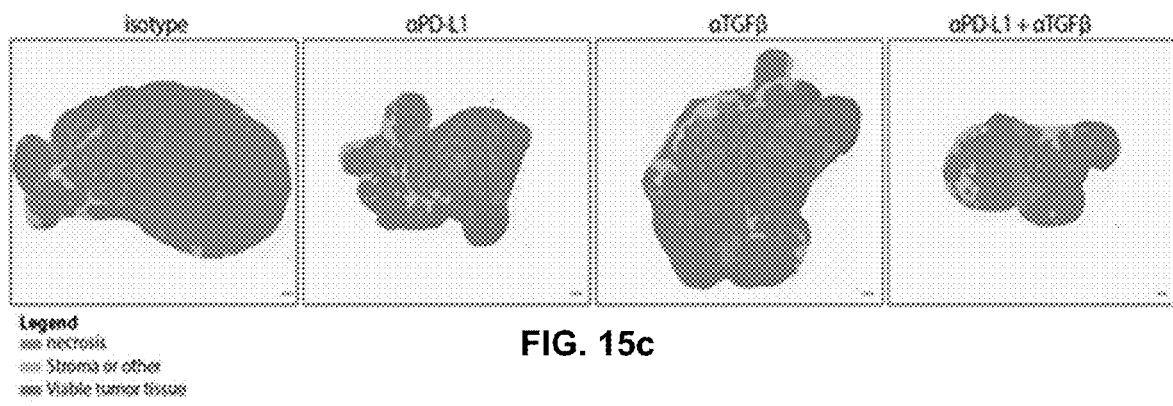

CD8 digital pathology analysis: Brightfield CD8-IHC slides were scanned at 20× magnification using the Nanozoomer slide scanner (Hamamatsu). Image analysis was performed on native .ndpi files using custom algorithms developed in Definiens Developer XD software (Munich, Germany). DAB (CD8) and Haematoxylin (nuclear counterstain) were isolated by HSD colour transformation (van Der Laak et al, 2000). Cells were segmented by thresholding on isolated haematoxylin stain then split using a watershed segmentation algorithm. DAB positivity was evaluated within individual cell boundaries to classify CD8+ cells. An automated region classification algorithm was applied within pathologist-annotated tumor borders to classify viable, necrotic, and stromal regions. Very small, punctate nuclei with dark haematoxylin counter stain were defined as necrotic. Sparse regions with small or elongated nuclei were classified as stroma or surrounding tissue (FIG. 15b-c). FIG. 15b shows a representation of a digital pathology analysis workflow for the CD8 IHC assay. FIG. 15c shows representative images of the digital analysis for CD8 IHC of one experiment with the digital mask of the regional classification. Only viable tumor tissue region was retained for the CD8 infiltration analysis.

Whole slide digital images of each immunolabeled tissue section were obtained using a Nanozoomer digital slide scanner (Hamamatsu). Tumor areas were manually annotated by a pathologist to include tumor using the MATLAB (MathWorks) software package. MATLAB was subsequently used to identify all viable cell nuclei based on size, shape, and labelling characteristics and to calculate mean DAB intensity for each nucleus. Four immunoreactivity levels (negative, weak, moderate, and strong) in a training set of the control and tumor tissue images. Nuclei were binned as weak positive, moderate positive, or strong positive and images were reviewed for algorithm accuracy. Final quantification results were reported as the digital histoscore (1*percent of weak nuclei+2*percent of moderate nuclei+3*percent of strong nuclei, range 0-300).

V. Additional Considerations

Some embodiments of the present disclosure include a system including one or more data processors. In some embodiments, the system includes a non-transitory computer readable storage medium containing instructions which, when executed on the one or more data processors, cause the one or more data processors to perform part or all of one or more methods and/or part or all of one or more processes disclosed herein. Some embodiments of the present disclosure include a computer-program product tangibly embodied in a non-transitory machine-readable storage medium, including instructions configured to cause one or more data processors to perform part or all of one or more methods and/or part or all of one or more processes disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention as claimed has been specifically disclosed by embodiments and optional features, modification and variation of the concepts herein disclosed may be resorted to by those skilled in the art, and that such modifications and variations are considered to be within the scope of this invention as defined by the appended claims.

The present description provides preferred exemplary embodiments only, and is not intended to limit the scope, applicability or configuration of the disclosure. Rather, the present description of the preferred exemplary embodiments will provide those skilled in the art with an enabling description for implementing various embodiments. It is understood that various changes may be made in the function and arrangement of elements without departing from the spirit and scope as set forth in the appended claims.

Specific details are given in the present description to provide a thorough understanding of the embodiments. However, it will be understood that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

What is claimed:

1. A method comprising:
   processing a sample from a subject to characterize immunoactivity, wherein processing the sample comprises:
   (i) generating gene expression level data corresponding to the subject for a predefined set of genes, wherein the generating comprises measuring nucleic acid levels or protein levels in the sample, and wherein for each gene in the predefined set of genes, an expression level of the gene had been identified as being informative of a quantity or a spatial distribution of CD8+ T cells; and
   (ii) based on the gene expression level data, (a) determining the quantity of CD8+ T cells in the sample or a portion thereof, or (b) characterizing the spatial distribution of the CD8+ T cells in the sample or a portion thereof;
   detecting, based on the gene expression level data and either the quantity or the spatial distribution of the CD8+ T cells, an immunosuppressive tumor microenvironment within the sample or the portion thereof; and
   prompting treatment of the subject with an inhibitor of TGFβ.

2. The method of claim 1, wherein the predefined set of genes includes at least one of GZMA, GZMB, GMZH, CD40LG, TAPBP, PSMB10, HLA-DOB, FAP, TDO2, and LRRTM3.

3. The method of claim 1, wherein the inhibitor of TGFβ includes Galunisertib.

4. The method of claim 1, wherein detecting the immunosuppressive tumor microenvironment includes determining that the sample includes T cell excluded tumor cells.

5. The method of claim 1, wherein processing the sample includes quantifying antigen presentation on tumor cells in at least part of the sample.

6. The method of claim 1, wherein prompting treatment of the subject with the inhibitor of TGFβ includes outputting a recommendation that the subject be treated with the inhibitor of TGFβ.

7. The method of claim 1, wherein detecting the immunosuppressive tumor microenvironment includes detecting a downregulation of MHC-1 expression in tumor cells.

8. The method of claim 1, wherein characterizing the spatial distribution of CD8+ T cells in the portion of the sample includes computing, based on one or more digital pathology images, a first quantity of CD8+ cells located in a tumor epithelium in the subject and a second quantity of CD8+ cells located in a tumor stroma in the subject.

9. The method of claim 1, herein processing the sample includes determining a quantity of CD8+ T cells in a portion of the sample and characterizing a spatial distribution of the CD8+ T cells in the portion of the sample, and wherein the immunosuppressive tumor microenvironment corresponds to the portion.

10. The method of claim 1, wherein the treatment further includes an inhibitor of PD-L1.

11. The method of claim 1, wherein the treatment further includes a checkpoint inhibitor.

12. The method of claim 1, wherein processing the sample includes measuring mRNA that corresponds to a precursor for a protein.

13. The method of claim 1, wherein processing the sample includes:
   fixing or embedding the sample;
   slicing the fixed or embedded sample to produce multiple sample slices;
   applying one or more stains to each of at least one of the multiple sample slices to produce one or more stained slices; and
   capturing a digital image of each of the one or more stained slices.

14. A method comprising:
   receiving a result of processing of a sample from a subject to characterize immunoactivity, wherein the result comprises gene expression level data corresponding to the subject for a predefined set of genes, wherein for each gene in the predefined set of genes, an expression level of the gene had been identified as being informative of a quantity or a spatial distribution of CD8+ T cells, and wherein the result further comprises either the quantity of CD8+ T cells in the sample or a portion thereof determined based on the gene expression level data or the spatial distribution of CD8+ T cells in the sample of a portion thereof characterized based on the gene expression level data;
   detecting, based on the result, an immunosuppressive tumor microenvironment within the sample or the portion thereof; and
   prompting treatment of the subject with an inhibitor of TGFβ.

* * * * *